United States Patent
Okano et al.

(10) Patent No.: US 9,273,128 B2
(45) Date of Patent: *Mar. 1, 2016

(54) PHARMACEUTICAL COMPOSITION FOR TREATMENT AND/OR PROPHYLAXIS OF CANCER

(75) Inventors: Fumiyoshi Okano, Kamakura (JP); Shinichi Kobayashi, Kamakura (JP); Yoshitaka Minamida, Kamakura (JP); Takanori Saito, Kamakura (JP)

(73) Assignee: TORAY INDUSTRIES, INC, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/236,793

(22) PCT Filed: Aug. 3, 2012

(86) PCT No.: PCT/JP2012/069862
§ 371 (c)(1),
(2), (4) Date: Feb. 3, 2014

(87) PCT Pub. No.: WO2013/018894
PCT Pub. Date: Feb. 7, 2013

(65) Prior Publication Data
US 2014/0186359 A1    Jul. 3, 2014

(30) Foreign Application Priority Data

Aug. 4, 2011 (JP) .................................. 2011-171300

(51) Int. Cl.
*C07K 16/30* (2006.01)
*A61K 39/395* (2006.01)
*C07K 16/18* (2006.01)
*A61K 45/06* (2006.01)
*C07K 16/28* (2006.01)

(52) U.S. Cl.
CPC ............ *C07K 16/18* (2013.01); *A61K 39/39558* (2013.01); *A61K 45/06* (2013.01); *C07K 16/28* (2013.01); *C07K 16/30* (2013.01); *C07K 2317/24* (2013.01); *C07K 2317/34* (2013.01); *C07K 2317/73* (2013.01); *C07K 2317/732* (2013.01)

(58) Field of Classification Search
CPC .............. C07K 16/30; C07K 16/315–16/3069; C07K 16/461–16/467; A61K 39/395; A61K 39/39558
See application file for complete search history.

(56) References Cited

U.S. PATENT DOCUMENTS

| | | | |
|---|---|---|---|
| 5,698,396 A | 12/1997 | Pfreundschuh | |
| 6,335,170 B1 | 1/2002 | Orntoft | |
| 6,444,425 B1 | 9/2002 | Reed et al. | |
| 7,449,184 B2 | 11/2008 | Allison et al. | |
| 7,485,302 B2 | 2/2009 | Adams et al. | |
| 7,745,391 B2 | 6/2010 | Mintz et al. | |
| 8,211,634 B2 | 7/2012 | Depinho et al. | |
| 8,709,418 B2 | 4/2014 | Okano et al. | |
| 8,828,398 B2 | 9/2014 | Kobayashi et al. | |
| 8,911,740 B2 * | 12/2014 | Saito et al. | 424/155.1 |
| 2002/0006404 A1 | 1/2002 | Hanna et al. | |
| 2003/0118599 A1 | 6/2003 | Algate et al. | |
| 2003/0190640 A1 | 10/2003 | Faris et al. | |
| 2004/0029114 A1 | 2/2004 | Mack et al. | |
| 2004/0236091 A1 | 11/2004 | Chicz et al. | |
| 2004/0258678 A1 | 12/2004 | Bodary et al. | |
| 2005/0003390 A1 | 1/2005 | Axenovich et al. | |
| 2005/0032113 A1 | 2/2005 | Tanaka et al. | |
| 2005/0244413 A1 | 11/2005 | Adolf et al. | |
| 2006/0019256 A1 | 1/2006 | Clarke et al. | |
| 2006/0069054 A1 | 3/2006 | Houghton et al. | |
| 2006/0275305 A1 | 12/2006 | Bryant | |
| 2007/0048301 A1 | 3/2007 | Bodary-Winter et al. | |
| 2007/0154931 A1 | 7/2007 | Radich et al. | |
| 2007/0264253 A1 | 11/2007 | Liu et al. | |
| 2008/0075722 A1 | 3/2008 | DePinho et al. | |
| 2008/0107668 A1 | 5/2008 | Philip et al. | |
| 2010/0068724 A1 | 3/2010 | Fung et al. | |
| 2011/0123492 A1 | 5/2011 | Okano et al. | |
| 2011/0136121 A1 | 6/2011 | Okano et al. | |
| 2011/0189700 A1 | 8/2011 | Moses et al. | |

(Continued)

FOREIGN PATENT DOCUMENTS

CN    1705676 A    12/2005
CN    101120252 A    2/2008

(Continued)

OTHER PUBLICATIONS

Bodey et al., "MAGE-1, a Cancer/Testis-Antigen, Expression in Childhood Astrocytomas as an Indicator of Tumor Progression," in vivo (2002) vol. 16, pp. 583-588.

(Continued)

*Primary Examiner* — Sheela J Huff
*Assistant Examiner* — Jessica H Roark
(74) *Attorney, Agent, or Firm* — Birch, Stewart, Kolasch & Birch, LLP

(57) ABSTRACT

This invention provides an antibody targeting a cancer antigenic protein specifically expressed on the surface of cancer cells and use thereof as a therapeutic and/or preventive agent for cancer. More specifically, the present invention provides an antibody, or a fragment thereof which has immunological reactivity with a partial CAPRIN-1 polypeptide consisting of the amino acid sequence shown by SEQ ID NO: 5 or an amino acid sequence having 80% or higher sequence identity to the amino acid sequence, and a pharmaceutical composition for treatment and/or prevention of cancer comprising the same as an active ingredient.

20 Claims, No Drawings

(56) References Cited

U.S. PATENT DOCUMENTS

| | | |
|---|---|---|
| 2011/0256144 A1 | 10/2011 | Okano et al. |
| 2012/0171699 A1 | 7/2012 | Goodman et al. |
| 2012/0214975 A1 | 8/2012 | Sandig et al. |
| 2012/0294860 A1 | 11/2012 | Ido et al. |
| 2012/0301471 A1 | 11/2012 | Kobayashi et al. |
| 2012/0301476 A1 | 11/2012 | Okano et al. |
| 2012/0321641 A1 | 12/2012 | Okano et al. |
| 2013/0045210 A1 | 2/2013 | Kobayashi et al. |
| 2013/0071398 A1 | 3/2013 | Saito et al. |
| 2014/0186359 A1 | 7/2014 | Okano et al. |
| 2014/0308283 A1 | 10/2014 | Minamida et al. |
| 2015/0218285 A1 | 8/2015 | Saito et al. |

FOREIGN PATENT DOCUMENTS

| | | |
|---|---|---|
| CN | 101189516 A | 5/2008 |
| CN | 101836116 A | 9/2010 |
| CN | 102170907 A | 8/2011 |
| CN | 102171570 A | 8/2011 |
| EP | 2 207 037 A1 | 7/2010 |
| EP | 2 325 648 A1 | 5/2011 |
| EP | 2322221 A | 5/2011 |
| EP | 2 532 367 A1 | 12/2012 |
| EP | 2 532 743 A1 | 12/2012 |
| EP | 2 832 365 A1 | 2/2015 |
| EP | 2 832 366 A1 | 2/2015 |
| JP | 2003-528587 A | 9/2003 |
| JP | 2006-316040 A | 11/2006 |
| JP | 2013-502205 A | 1/2013 |
| JP | 2013-505028 A | 2/2013 |
| RU | 2234942 C2 | 2/2003 |
| RU | 2306952 C2 | 2/2003 |
| RU | 2006137060 A | 4/2008 |
| WO | WO 00/04149 A2 | 1/2000 |
| WO | WO 00/60077 A2 | 10/2000 |
| WO | WO 01/32910 A2 | 5/2001 |
| WO | WO 01/72295 A2 | 10/2001 |
| WO | WO 02/078524 A2 | 10/2002 |
| WO | WO 02/083070 A2 | 10/2002 |
| WO | WO 02/092001 A2 | 11/2002 |
| WO | 2002-540790 A | 12/2002 |
| WO | WO 2004/076682 A2 | 9/2004 |
| WO | WO 2004/097051 A2 | 11/2004 |
| WO | WO 2005/007830 A2 | 1/2005 |
| WO | WO 2005/100998 A2 | 10/2005 |
| WO | WO 2005/116076 A2 | 12/2005 |
| WO | WO 2006/002378 A2 | 1/2006 |
| WO | WO 2007/150077 A2 | 12/2007 |
| WO | WO 2008/031041 A2 | 3/2008 |
| WO | WO 2008/059252 A2 | 5/2008 |
| WO | WO 2008/073162 A2 | 6/2008 |
| WO | WO 2008/088583 A2 | 7/2008 |
| WO | WO 2009/113742 A | 9/2009 |
| WO | WO 2009/117277 A2 | 9/2009 |
| WO | WO 2010/016525 A1 | 2/2010 |
| WO | WO 2010/016526 A1 | 2/2010 |
| WO | WO 2010/016527 A1 | 2/2010 |
| WO | WO2011/096517 * | 8/2011 |
| WO | WO 2011/096517 A1 | 8/2011 |
| WO | WO 2011/096528 A1 | 8/2011 |
| WO | WO 2011/096533 A1 | 8/2011 |
| WO | WO 2011/096534 A1 | 8/2011 |
| WO | WO 2011/096535 A1 | 8/2011 |
| WO | WO 2012/005550 A2 | 1/2012 |
| WO | WO 2012/013609 A1 | 2/2012 |
| WO | WO 2013/018885 A1 | 2/2013 |
| WO | WO 2013/018886 A1 | 2/2013 |
| WO | WO 2013/018894 A1 | 2/2013 |
| WO | WO 2013/147169 A1 | 10/2013 |
| WO | WO 2013/147176 A1 | 10/2013 |

OTHER PUBLICATIONS

Comtesse et al., "Probing the human natural autoantibody repertoire using an immunoscreening approach," Clin. Exp. Immunol. (2000), vol. 121, pp. 430-436.

Jager et al., "Identification of a Tissue-specific Putative Transcription Factor in Breast Tissue by Serological Screening of a Breast Cancer Library," Cancer Research (Mar. 1, 2001), vol. 61, pp. 2055-2061.

Jungbluth et al., "Immunohistochemical Analysis of NY-ESO-1 Antigen Expression in Normal and Malignant Human Tissues," Int. J. Cancer (2001), vol. 92, pp. 856-860.

Kohler et al., "Tumor antigen analysis in neuroblastoma by serological interrogation of bioinformatic data," Cancer Science (Nov. 2010), vol. 101, No. 11, pp. 2316-2324.

Nakamura et al. "Gene Expression Profile of Metastatic Human Pancreatic Cancer Cells Depends on the Organ Microenvironment," Cancer Research (Jan. 1, 2007), vol. 67, No. 1, pp. 139-148.

Non-Final Office Action issued Nov. 6, 2014, in U.S. Appl. No. 13/576,950.

Pegram et al., "Rational Combinations of Trastuzumab with Chemotherapeutic Drugs Used in the Treatment of Breast Cancer," Journal of the National Cancer Institute (May 19, 2004), vol. 96, No. 10, pp. 739-749.

Punt et al., "Edrecolomab alone or in combination with fluorouracil and folinic acid in the adjuvant treatment of stage III colon cancer: a randomised study," Lancet (Aug. 31, 2002), vol. 360, No. 9334, pp. 671-677.

Buchsbaum et al., "Treatment of Pancreatic Cancer Xenografts with Erbitux (IMC-C225) Anti-EGFR Antibody, Gemcitabine, and Radiation," Int. J. Radiation Oncology Biol. Phys. (2002), vol. 54, No. 4, pp. 1180-1193.

Chames et al., "Therapeutic Antibodies for the Treatment of Pancreatic Cancer," The Scientific World Journal (Jan. 1, 2010), vol. 10, pp. 1107-1120.

Eccleston et al., "Pancreatic Tumor Marker Anti-Mucin Antibody CAM 17.1 Reacts with a Sialyl Blood Group Antigen, Probably I, Which is Expressed throughout the Human Gastrointestinal Tract," Digestion (1998), vol. 59, pp. 665-670.

Esteva et al., "Chemotheraphy of Metastatic Breast Cancer: What to Expect in 2001 and Beyond," The Oncologist (2001), vol. 6, pp. 133-146.

Extended European Search Report issued Feb. 2, 2015, in European Patent Application No. 12819473.5.

Extended European Search Report issued Jan. 29, 2015, in European Patent Application No. 12819899.1.

Houghton, P. J. and J. A. Houghton, "Evaluation of Single-Agent Therapy in Human Colorectal Tumour Xenografts," Br. J. Cancer (1978), vol. 37, pp. 833-840.

Akiyoshi, "Cancer Vaccine Therapy Using Peptides Derived from Tumor-Rejection Antigens," Jpn J Cancer Chemother., vol. 24, No. 5, Mar. 1997, pp. 511-519, with English Abstract (p. 519).

Balmana et al., "BRCA in breast cancer: ESMO Clinical Recommendations," Annals of Oncology, vol. 20, Supplemental 4, 2009, pp. iv19-iv20.

Bodey et al., "Failure of Cancer Vaccines: The Significant Limitations of this Approach to Immunotherapy," Anticancer Research, vol. 20, 2000, pp. 2665-2676.

Brand et al., "Prospect for Anti-HER2 Receptor Therapy in Breast Cancer," Anticancer Research, vol. 26, 2006, pp. 463-470.

Brass et al., "Translation initiation factor eIF-4gamma is encoded by an amplified gene and induces an immune response in squamous cell lung carcinoma," Human Molecular Genetics, vol. 6, No. 1, 1997, pp. 33-39.

Chamberlain et al., "Innovations and strategies for the development of anticancer vaccines," Expert Opinion on Pharmacotherapy, vol. 1, No. 4, 2000, pp. 603-614.

Ellis, et al., "Identification and Characterization of a Novel Protein (p137) Which Transcytoses Bidirectionally in Caco-2 Cells", The Journal of Biological Chemistry, Sep. 1, 1995, vol. 270, No. 35, pp. 20717-20723.

European Search Report, dated Aug. 13, 2013, for European Application No. 11739882.6.

European Search Report, dated Aug. 26, 2011, for European Application No. No. 09805010.7.

European Search Report, dated Jan. 30, 2013, for European Application 09805009.9.

European Search Report, dated Nov. 6, 2013, for European Application No. 11739876.8.

(56) References Cited

OTHER PUBLICATIONS

Evans et al., "Vaccine therapy for cancer-fact or fiction?", Q J Med, vol. 92, 1999, pp. 299-307.
GeneCards, "Cell Cycle Associated Protein 1—Biological research products for CAPRIN 1," updated Mar. 19, 2013, 10 pages.
Grill et al., "Activation/Division of Lymphocytes Results in Increased Levels of Cytoplasmic Activation/Proliferation-Associated Protein-1: Prototype of a New Family of Proteins," The Journal of Immunology, vol. 172, 2004, pp. 2389-2400.
Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.
Gure et al., "SSX: A Multigene Family with Several Members Transcribed in Normal Testis and Human Cancer," Int. J. Cancer, vol. 72, 1997, pp. 965-971.
Harlow et al., "Antibodies a Laboratory Manual", Cold Spring Harbor Laboratory, Chapter 3, 1988, pp. 23-34.
Hugo Gene Nomenclature Committee, Gene Symbol Report, CAPRIN1, Approved Name: Cell Cycle Associated Protein 1, HGNC ID: HGNC:6743, Nov. 3, 2012, 2 pages.
International Search Report and Written Opinion of the International Searching Authority, dated Mar. 1, 2011, for International Application No. PCT/JP2011/052413.
International Search Report, dated Mar. 15, 2011, for International Application No. PCT/JP2011/052384.
International Search Report, dated Mar. 8, 2011, for International Application No. PCT/JP2011/052403.
International Search Report, dated Mar. 8, 2011, for International Application No. PCT/JP2011/052414.
International Search Report, dated Oct. 6, 2009, for International Application No. PCT/JP2009/063882.
International Search Report, dated Sep. 8, 2009, for International Application No. PCT/JP2009/063883.
Itoh et al., "HUB1 is an autoantigen frequently eliciting humoral immune response in patients with adult T cell leukemia," Int. J. Oncol., vol. 14, No. 4, Apr. 1999, pp. 703-708 (Abstract only provided).
Jang et al., "Antihypertensive Angiotensin I-Converting Enzyme Inhibitory Activity and Antioxidant Activity of Vitis hybrid-Vitis coignetiae Red Wine Made with *Saccharomyces cerevisiae*," Mycobiology, vol. 39, No. 2, 2011, pp. 137-139.
Kaddar et al., "Two new miR-16 targets: caprin-1 and HMGA1, proteins implicated in cell proliferation," Biology of the Cell, vol. 101, No. 9, 2009, pp. 511-524.
Kajiji et al., "Six Monoclonal Antibodies to Human Pancreatic Cancer Antigens," Cancer Research, vol. 47, Mar. 1, 1987, pp. 1367-1376.
Karauzum et al., "Caprin 1 is Frequently Overexpressed in Human Lymphomas," American Society of Human Genetics, Cancer Genetics, Program No. 1190W, Oct. 12, 2011, One page (Abstract only).
Kataja et al., "Primary breast cancer: ESMO Clinical Recommendations for diagnosis, treatment and follow-up," Annals of Oncology, vol. 20, Supplement 4, 2009, pp. iv10-iv14.
Katsafanas et al., "Colocalization of Transcription and Translation within Cytoplasmic Poxvirus Factories Coordinates Viral Expression and Subjugates Host Functions," Cell Host & Microbe, vol. 2, Oct. 2007, pp. 221-228.
Katsafanas et al., "Vaccinia Virus Intermediate Stage Transcription Is Complemented by Ras-GTPase-activating Protein SH3 Domain-binding Protein (G3BP) . . . ," Jour. of Biol. Chem., vol. 279, No. 50, Dec. 10, 2004, pp. 52210-52217.
Kolobova et al., "Microtubule-dependent association of AKAP350A and CCAR1 with RNA stress granules," Experimental Cell Research, vol. 315, 2009 (Available online Dec. 3, 2008), pp. 542-555.
Lu et al., "Identification of an immunological signature of tumor rejection in the neu transgenic mouse," 2007 AACR Annual Meeting, Apr. 14-18, 2007 (Presentation conducted on Apr. 17, 2007), One page (Abstract only provided).
Lu et al., "Targeting serum antibody for cancer diagnosis: a focus on colorectal cancer," Expert Opin. Ther. Targets, vol. 11, No. 2, 2007, pp. 235-244.
Müller-Pillasch et al., "Identification of a new tumour-associated antigen TM4SF5 and its expression in human cancer," Gene, vol. 208, 1998, pp. 25-30.
Munodzana et al., "Conformational Dependence of Anaplasma marginale Major Surface Protein 5 Surface-Exposed B-Cell Epitopes", Infection and Immunity, vol. 66, No. 6, Jun. 1998, pp. 2619-2624.
NCBI Reference Sequence, caprin-1 [Bos taurus], 2009, Accession No. NP_001069530, XP_615677, 1 page.
NCBI Reference Sequence, caprin-1 [Gallus genus], 2005, Accession No. NP_001026536, XP_423820, 1 page.
NCBI Reference Sequence, caprin-1 isoform 1 [*Homo sapiens*], 1995, Accession No. NP_005889, 3 pages.
NCBI Reference Sequence, caprin-1 isoform 2 [*Homo sapiens*], 1995, Accession No. NP_976240, 3 pages.
NCBI Reference Sequence, caprin-1 isoform a [Mus musculus], 1996, Accession No. NP_058019, 3 pages.
NCBI Reference Sequence, caprin-1 isoform b [Mus musculus], 1996, Accession No. NP_001104760, 3 pages.
NCBI Reference Sequence, caprin-1 isoform c [Mus musculus], 1996, Accession No. NP_001104761, 4 pages.
NCBI Reference Sequence, Predicted: caprin-1 [Equus caballus], 2008, Accession No. XP_001492799, 1 page.
NCBI Reference Sequence, Predicted: caprin-1 isoform 2 [Canis lupus familiaris], Dec. 2, 2011, Accession No. XP_858109, 1 page.
Nelson et al., "Screening for Breast Cancer: An Update for the U.S. Preventive Services Task Force," Ann. Intern. Med., vol. 151, No. 10, Nov. 17, 2009, pp. 727-737.
Okano et al., "Abstract 519: Identification of a novel target for antibody therapy of breast cancer", Cancer Research, vol. 72, Issue 8, Supplement 1, Apr. 15, 2012, XP-002700046, 2 pages.
Polyak et al., "Alanine-170 and proline-172 are critical determinants for extracellular CD20 epitopes; heterogeneity in the fine specificity of CD20 monoclonal antibodies is defined by additional requirements imposed by both amino acid sequence . . . ", Blood, vol. 99, No. 9, May 1, 2002, pp. 3256-3262.
R & D Systems, "IHC Products & Protocol Guide," printed Jan. 9, 2014, pp. 1-112.
Sahin et al., "Human neoplasms elicit multiple specific immune responses in the autologous host," Proc. Natl. Acad. Sci. USA, vol. 92, Dec. 1995, pp. 11810-11813.
Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.
Scanlan et al., "Characterization of Human Colon Cancer Antigens Recognized by Autologous Antibodies," Int. J. Cancer, vol. 76, 1998, pp. 652-658.
Solomon et al., "Distinct Structural Features of Caprin-1 Mediate Its Interaction with G3BP-1 and Its Induction of Phosphorylation of Eukaryotic Translation Initiation Factor 2α, Entry to Cytoplasmic Stress . . . ," Molecular and Cellular Biology, vol. 27, No. 6, Mar. 2007, XP_002690351, pp. 2324-2342.
Strome et al., "A Mechanistic Perspective of Monoclonal Antibodies in Cancer Therapy Beyond Target-Related Effects," The Oncologist, vol. 12, 2007, pp. 1084-1095.
Türeci et al., "The SSX-2 Gene, Which Is Involved in the t(X; 18) Translocation of Synovial Sarcomas, Codes for the Human Tumor Antigen HOM-MEL-40," Cancer Research, vol. 56, Oct. 15, 1996, pp. 4766-4772.
United States Notice of Allowance, dated Dec. 2, 2013, for U.S. Appl. No. 13/576,955.
United States Office Action, dated Aug. 19, 2013, for U.S. Appl. No. 13/576,955.
United States Office Action, dated Aug. 26, 2013, for U.S. Appl. No. 13/576,950.
United States Office Action, dated Dec. 21, 2012, for U.S. Appl. No. 13/057,515.
United States Office Action, dated Dec. 21, 2012, for U.S. Appl. No. 13/057,709.

(56) References Cited

OTHER PUBLICATIONS

United States Office Action, dated Jan. 16, 2014, for U.S. Appl. No. 13/057,515.
United States Office Action, dated Jul. 1, 2013, for U.S. Appl. No. 13/057,515.
United States Office Action, dated Jul. 1, 2013, for U.S. Appl. No. 13/577,212.
United States Office Action, dated Jul. 16, 2013, for U.S. Appl. No. 13/057,709.
United States Office Action, dated Jun. 14, 2013, for U.S. Appl. No. 13/576,969.
United States Office Action, dated Mar. 13, 2013, for U.S. Appl. No. 13/576,955.
United States Office Action, dated Nov. 15, 2013, for U.S. Appl. No. 13/576,953.
United States Office Action, dated Nov. 15, 2013, for U.S. Appl. No. 13/577,028.
United States Office Action, dated Nov. 15, 2013, in U.S. Appl. No. 13/576,950.
United States Office Action, dated Nov. 2, 2012, for U.S. Appl. No. 13/057,709.
United States Office Action, dated Nov. 9, 2012, for U.S. Appl. No. 13/057,515.
United States Office Action, dated Oct. 15, 2013, for U.S. Appl. No. 13/576,969.
United States Office Action, dated Oct. 21, 2013, for U.S. Appl. No. 13/577,212.
United States Office Action, dated Sep. 19, 2013, for U.S. Appl. No. 13/577,028.
United States Office Action, dated Sep. 6, 2013, for U.S. Appl. No. 13/576,953.
Van Der Bruggen et al., "A Gene Encoding an Antigen Recognized by Cytolytic T Lymphocytes on a Human Melanoma," Science, vol. 254, Dec. 13, 1991, pp. 1643-1647 (Also published in J. Immunol., vol. 178, 2007, pp. 2617-2621).
Wang et al., "Absence of Caprin-1 Results in Defects in Cellular Proliferation", The Journal of Immunology, 2005, vol. 175, pp. 4274-4282.
Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Publ. online Mar. 30, 2010), pp. 85-92.
De Pascalis et al., "Grafting of "Abbreviated" Complementary-Determining Regions Containing Specificity-Determining Residues Essential for Ligand Contact to Engineer a Less Immunogenic Humanized Monoclonal Antibody," J. Immunol. (2002), vol. 169, pp. 3076-3084.
Extended European Search Report issued Mar. 2, 2015, in European Patent Application No. 12819759.7.
Riechmann et al., "Reshaping Human Antibodies for Therapy," Nature (Mar. 24, 1988), vol. 332, pp. 323-327.
Russian Office Action issued Jan. 28, 2015 in Russian Patent Application No. 2012137502, with partial English translation.

Vajdos et al., "Comprehensive Functional Maps of the Antigen-binding Site of an Anti-ErbB2 Antibody Obtained with Shotgun Scanning Mutagenesis," J. Mol. Biol. (2002), vol. 320, pp. 415-428.
Gong et al., "Caprin-1 is a novel microRNA-223 target for regulating the proliferation and invasion of human breast cancer cells", Biomedicine & Pharmacotherapy, vol. 67, 2013, pp. 629-636.
Qiu et al., "Targeting a ribonucleoprotein complex containing the caprin-1 protein and the c-Myc mRNA suppresses tumor growth in mice: an identification of a novel oncotarget", Oncotarget, vol. 6, No. 4, Dec. 10, 2014, pp. 2148-2163.
Sabile et al., "Caprin-1, a novel Cyr61-interacting protein, promotes osteosarcoma tumor growth and lung metastasis in mice", Biochimica et Biophysica Acta, vol. 1832, 2013 (available online Mar. 23, 2013), pp. 1173-1182.
U.S. Office Action for U.S. Appl. No. 13/576,950, dated Mar. 30, 2015.
Extended European Search Report issued Mar. 18, 2015, in European Patent Application No. 12820225.6.
Extended European Search Report issued Mar. 23, 2015, in European Patent Application No. 12820596.0.
GenBank Accession No. AAU93399, Sep. 22, 2005.
GenBank Accession No. BAF96513, Jan. 5, 2008.
GenBank Accession No. NM_001031365, Sep. 25, 2007.
GenBank Accession No. NM_001076062, Feb. 9, 2008.
GenBank Accession No. NM_001111289, Feb. 11, 2008.
GenBank Accession No. NM_001111290, Feb. 11, 2008.
GenBank Accession No. NM_001111291, Feb. 10, 2008.
GenBank Accession No. NM_001111292, Feb. 11, 2008.
GenBank Accession No. NM_016739, Feb. 10, 2008.
GenBank Accession No. NM_05898, Feb. 11, 2008.
GenBank Accession No. NM_203364, Feb. 10, 2008.
GenBank Accession No. Q14444, Jun. 10, 2008.
GenBank Accession No. Q1LZB6, Jun. 10, 2008.
GenBank Accession No. XM_853016, Aug. 30, 2005.
Patent Examination Report No. 1 issued Oct. 14, 2014, in Australian Patent Application No. 2009278387.
Corada et al., "Monoclonal antibodies directed to different regions of vascular endothelial cadherin extracellular domain affect adhesion and clustering of the protein and modulate endothelial permeability," Blood (Mar. 15, 2001), vol. 97, No. 6, pp. 1679-1684.
Office Action issued Aug. 14, 2015, in U.S. Appl. No. 14/236,818.
Office Action issued Aug. 20, 2015, in U.S. Appl. No. 14/452,746.
Office Action issued Jul. 3, 2015, in Russian Patent Application No. 2012137503.
Office Action issued Sep. 15, 2015, in U.S. Appl. No. 14/389,266.
Padlan, E. A., "X-Ray Crystallography of Antibodies," Adv. Prot. Chem. (1996), vol. 49, pp. 57-133.
Saffari et al., "Identification of novel p53 target genes by cDNA AFLP in glioblastoma cells", Cancer Letters, 2009, No. 273, pp. 316-322.
GenBank Accession No. NM_005898, Feb. 11, 2008.
U.S. Office Action for U.S. Appl. No. 14/379,867, dated Jun. 24, 2015.
Extended European Search Report for European Application No. 13767612.8, dated Sep. 22, 2015.
Extended European Search Report for European Application No. 13769665.4, dated Sep. 22, 2015.

* cited by examiner

PHARMACEUTICAL COMPOSITION FOR TREATMENT AND/OR PROPHYLAXIS OF CANCER

TECHNICAL FIELD

The present invention relates to novel use of an antibody against CAPRIN-1 or a fragment thereof in a drug such as a therapeutic and/or preventive agent for cancer.

BACKGROUND ART

Cancer is the leading cause of death. This disease is currently treated principally by surgical therapy, in combination with radiation therapy and/or chemotherapy. In spite of recent development of novel surgical techniques or discovery of novel anticancer agents, the existing treatment of cancer has an insufficiently improved outcome, except for some cancer types. With recent advances of molecular biology or cancer immunology, antibodies that specifically react with cancer, cancer antigens that are recognized by cytotoxic T cells, genes encoding such cancer antigens, and the like have been identified, raising expectations on specific cancer therapy targeting the cancer antigens (Non Patent Literature 1).

For reducing the adverse reaction of cancer therapy, it is desired that peptides, polypeptides, or proteins recognized as antigens of the cancer should rarely exist in normal cells and specifically exist in cancer cells. In 1991, Boon et al. (Ludwig Institute for Cancer Research, Belgium) isolated a human melanoma antigen MAGE1 recognized by CD8-positive T cells by a cDNA expression cloning method using autologous cancer cell lines and cancer-reactive T cells (Non Patent Literature 2). Then, a SEREX (serological identification of antigens by recombinant expression cloning) method has been reported, which adopts a gene expression cloning approach to identify tumor antigens recognized by antibodies produced in response to autologous cancer in vivo in a cancer patient (Non Patent Literature 3 and Patent Literature 1). According to this method, some cancer antigens that are rarely expressed in normal cells and are specifically expressed in cancer have been isolated (Non Patent Literatures 4 to 9). In addition, cell therapy using immunocytes that specifically react with cancer antigens or cancer-specific immunotherapy using vaccines or the like comprising cancer antigens is under clinical trial targeting some of the isolated cancer antigens.

In recent years, various antibody drugs for cancer treatment targeting antigenic proteins on cancer cells have emerged in the world. These drugs have received attention because of their certain efficacy as cancer-specific therapeutic agents. A large majority of antigenic proteins targeted by the drugs, however, are also expressed in normal cells. As a result of administering the antibodies, cancer cells as well as normal cells expressing the antigens are damaged, disadvantageously resulting in adverse reaction. Thus, if cancer antigens specifically expressed on the surface of cancer cells can be identified and antibodies targeting the antigens can be used as drugs, these antibody drugs can be expected to achieve treatment with less adverse reaction.

Cytoplasmic- and proliferation-associated protein 1 (CAPRIN-1) has been known as an intracellular protein that is expressed upon activation or cell division of resting normal cells and forms cytoplasmic stress granules with RNAs in cells to participate in the regulation of transport and translation of mRNAs. This protein has been found to be specifically expressed on the surface of cancer cells and is therefore under study as a target of antibody drugs for cancer treatment (Patent Literature 2).

CITATION LIST

Patent Literature

Patent Literature 1: U.S. Pat. No. 5,698,396
Patent Literature 2: WO2010/016526

Non Patent Literature

Non Patent Literature 1: Tsuyoshi Akiyoshi, "Japanese Journal of Cancer and Chemotherapy", 1997, Vol. 24, p. 55-519 (Japanese Journal of Cancer and Chemotherapy Publishers Inc., Japan)
Non Patent Literature 2: Bruggen P. et al., Science, 254: 1643-1647 (1991)
Non Patent Literature 3: Proc. Natl. Acad. Sci. USA, 92: 11810-11813 (1995)
Non Patent Literature 4: Int. J. Cancer, 72: 965-971 (1997)
Non Patent Literature 5: Cancer Res., 58: 1034-1041 (1998)
Non Patent Literature 6: Int. J. Cancer, 29: 652-658 (1998)
Non Patent Literature 7: Int. J. Oncol., 14: 703-708 (1999)
Non Patent Literature 8: Cancer Res., 56: 4766-4772 (1996)
Non Patent Literature 9: Hum. Mol. Genet. 6: 33-39, 1997

SUMMARY OF INVENTION

Technical Problem

An object of the present invention is to produce an antibody which targets CAPRIN-1 specifically expressed on the surface of cancer cells and has better antitumor activity than conventional antibodies, and provide use of the antibody as a therapeutic and/or preventive agent for cancer.

Solution to Problem

The present invention has the following aspects:

The present invention provides an antibody or a fragment thereof which has immunological reactivity with a partial CAPRIN-1 polypeptide having the amino acid sequence shown by SEQ ID NO: 5 or an amino acid sequence having 80% or higher sequence identity to the amino acid sequence, and a pharmaceutical composition for treatment and/or prevention of cancer, comprising the same as an active ingredient.

In one embodiment of the present invention, the cancer is breast cancer, kidney cancer, pancreatic cancer, colorectal cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma.

In another embodiment, the antibody is a monoclonal antibody or a polyclonal antibody.

In an alternative embodiment, the antibody is a human antibody, a humanized antibody, a chimeric antibody, a single-chain antibody, or a multispecific antibody (e.g. bispecific antibody).

The present specification includes the contents disclosed in Japanese Patent Application No. 2011-171300 to which the present application claims priority.

Advantageous Effects of Invention

The antibody against CAPRIN-1 according to the present invention damages cancer cells. Thus, the antibody against CAPRIN-1 is useful in the treatment and/or prevention of cancer.

DESCRIPTION OF EMBODIMENTS

The antibody according to the present invention is an antibody that recognizes and binds to a predetermined partial polypeptide of CAPRIN-1 and has antitumor activity. The antibody according to the present invention is more specifically an antibody that recognizes (i.e., has immunological reactivity with) a partial polypeptide of a CAPRIN-1 protein (partial CAPRIN-1 polypeptide) consisting of the amino acid sequence shown by SEQ ID NO: 5 or an amino acid sequence having 80% or higher, preferably 85% or higher, more preferably 90% or higher, further preferably 95% or higher sequence identity to the amino acid sequence. The present invention has revealed that this antibody exhibits antitumor activity. The present invention relates to all antibodies that bind to the fragments of CAPRIN-1 proteins as described above and exhibit antitumor activity.

The antibody against CAPRIN-1 according to the present invention may be any type of antibody that can exert antitumor activity and includes, for example, recombinant antibodies, for example, synthetic antibodies, multispecific antibodies (e.g., bispecific antibodies), humanized antibodies, chimeric antibodies, and single-chain antibodies (scFv), human antibodies, and their antibody fragments, for example, Fab, F(ab')$_2$, and Fv. These antibodies and fragments thereof can be prepared by methods known to those skilled in the art. Desirably, the antibody according to the present invention has immunological reactivity with a CAPRIN-1 protein or a partial polypeptide thereof, i.e., binds to the CAPRIN-1 protein through antigen-antibody reaction, preferably, specifically binds to the CAPRIN-1 protein. In this context, the phrase "specifically binding to the CAPRIN-1 protein" means that the antibody specifically binds to the CAPRIN-1 protein without substantially binding to other proteins. The antibody according to the present invention is preferably a monoclonal antibody. Alternatively, the antibody according to the present invention may be a polyclonal antibody as long as homogeneous antibodies can be stably produced. In the case of a human subject, a human antibody or a humanized antibody is desirable for avoiding or suppressing rejection.

The antibody against CAPRIN-1 polypeptide according to the present invention can be examined for its antitumor activity, as described later, by examining in vivo the inhibition of tumor growth in a cancer-bearing animal or by examining ex vivo the presence or absence of immunocyte- or complement-mediated cytotoxic activity exhibited by the antibody against tumor cells expressing the polypeptide.

The subject to receive the treatment and/or prevention of cancer according to the present invention is a mammal such as a human, a pet animal, livestock, or a sport animal, preferably a human.

Hereinafter, the present invention will be described in more detail.

<Preparation of Antigen for Antibody Preparation>

Proteins or fragments thereof used as sensitizing antigens for obtaining the antibody against CAPRIN-1 according to the present invention are not limited by animal species serving as their origins, including humans, dogs, cattle, horses, mice, rats, and chickens. The proteins or the fragments thereof, however, are preferably selected in view of compatibility with parent cells for use in cell fusion. In general, mammal-derived proteins are preferred. Particularly, human-derived proteins are preferred. For example, when CAPRIN-1 is human CAPRIN-1, human CAPRIN-1 proteins, partial peptides thereof, or cells expressing human CAPRIN-1 can be used.

The nucleotide sequences and amino acid sequences of human CAPRIN-1 and homologs thereof are available, for example, by accessing GenBank (NCBI, USA) and using BLAST or FASTA algorithm (Karlin and Altschul, Proc. Natl. Acad. Sci. USA, 90: 5873-5877, 1993; and Altschul et al., Nucleic Acids Res. 25: 3389-3402, 1997).

In the present invention, with reference to the nucleotide sequence (SEQ ID NO: 1 or 3) or amino acid sequence (SEQ ID NO: 2 or 4) of human CAPRIN-1, the target CAPRIN-1 is nucleic acids or proteins consisting of sequences having 70% to 100%, preferably 80% to 100%, more preferably 90% to 100%, further preferably 95% to 100%, for example, 97% to 100%, 98% to 100%, 99% to 100%, or 99.5% to 100% sequence identity to the nucleotide sequence or amino acid sequence of the ORF or mature portion of the reference sequence. In this context, the term "% sequence identity" means a percentage (%) of the number of identical amino acids (or nucleotide bases) to the total number of amino acids (or nucleotide bases) when two sequences are aligned such that the maximum degree of similarity (or identity) can be achieved with or without introduced gaps.

As the fragments of each CAPRIN-1 protein, those comprising an epitope (or an antigenic determinant), which is the smallest unit recognized by an antibody, and having lengths ranging from the amino acid length of the epitope to less than the full-length of the protein can be used. The epitope refers to a polypeptide fragment having antigenicity or immunogenicity in mammals, preferably humans. Its smallest unit consists of approximately 7 to 12 amino acids, for example, 8 to 11 amino acids. The fragments of CAPRIN-1 protein to be used in the preparation of the antibody according to the present invention are preferably fragments each comprising the amino acid sequence shown by SEQ ID NO: 5 or an amino acid sequence having 80% or higher, preferably 85% or higher, more preferably 90% or higher, further preferably 95% or higher sequence identity to the amino acid sequence, recognized by the antibody of the present invention, or comprising at least an epitope consisting of approximately 7 to 12 consecutive amino acids, for example, 8 to 11 consecutive amino acids, in any of these amino acid sequences.

Polypeptide fragments comprising the above human CAPRIN-1 proteins and partial peptides thereof can be synthesized according to chemical synthesis methods, for example, Fmoc (fluorenylmethyloxycarbonyl) and tBoc (t-butyloxycarbonyl) methods (Seikagaku Jikken Koza (Biochemical Experimentation Course in English) 1, the Japanese Biochemical Society ed., Protein Chemistry IV, Chemical Modification and Peptide Synthesis, Tokyo Kagaku Dojin Co., Ltd. (Japan), 1981). Also, these polypeptides can be synthesized by conventional methods using various commercially available peptide synthesizers.

Alternatively, polynucleotides encoding the polypeptides may be prepared using genetic engineering approaches known in the art (Sambrook et al., Molecular Cloning, the 2nd edition, Current Protocols in Molecular Biology (1989), Cold Spring Harbor Laboratory Press; Ausubel et al., Short Protocols in Molecular Biology, the 3rd edition, A compendium of Methods from Current Protocols in Molecular Biology (1995), John Wiley & Sons; etc.) and incorporated into expression vectors, which are then introduced into host cells to produce the polypeptides in the host cells. In this way, the human CAPRIN-1 proteins or polypeptide fragments thereof of interest can be obtained.

The polynucleotides encoding the polypeptides can be readily prepared by genetic engineering approaches known in the art or conventional methods using commercially available nucleic acid synthesizers. For example, a DNA comprising the nucleotide sequence of human CAPRIN-1 gene can be prepared by PCR using a human chromosomal DNA or cDNA library as a template and a pair of primers designed so as to be capable of amplifying the nucleotide sequence. Reaction conditions for this PCR can be appropriately determined. Examples of the conditions can include, but not limited to, 30 cycles each involving reaction steps consisting of 94° C. for 30 seconds (denaturation), 55° C. for 30 seconds to 1 minute (annealing), and 72° C. for 2 minutes (elongation) using thermostable DNA polymerase (e.g., Taq polymerase, Pfu polymerase or the like) and a $Mg^{2+}$-containing PCR buffer, followed by reaction at 72° C. for 7 minutes. The PCR approach, conditions, etc. are described in, for example, Ausubel et al., Short Protocols in Molecular Biology, the 3rd edition, A Compendium of Methods from Current Protocols in Molecular Biology (1995), John Wiley & Sons (particularly, Chapter 15).

Also, appropriate probes or primers can be prepared on the basis of information about the nucleotide sequences of CAPRIN-1 gene and the amino acid sequences of CAPRIN-1 proteins, and used in the screening of, for example, a human cDNA library, to isolate the desired DNA. Preferably, such a cDNA library is produced from cells, organs, or tissues expressing proteins of CAPRIN-1. Examples of such cells or tissues include cells or tissues derived from the testis or from cancers or tumors such as leukemia, breast cancer, lymphoma, brain tumor, lung cancer, pancreatic cancer, and colorectal cancer. These operations, including the preparation of probes or primers, the construction of a cDNA library, the screening of the cDNA library, and the cloning of the gene of interest, are known to those skilled in the art and can be performed according to methods described in, for example, Sambrook et al., Molecular Cloning, the 2nd edition, Current Protocols in Molecular Biology (1989), and Ausubel et al. (ibid.). DNAs encoding the human CAPRIN-1 proteins and the partial peptides thereof can be obtained from the DNA thus obtained.

The host cells into which the expression vectors are introduced may be any cell capable of expressing the above polypeptides. Examples of prokaryotic cells include, but not limited to, E. coli. Examples of eukaryotic cells include, but not limited to: mammalian cells such as monkey kidney cells COS1 and Chinese hamster ovary cells CHO; a human embryonic kidney cell line HEK293; mouse embryonic skin cell line NIH3T3; yeast cells such as budding yeast and fission yeast cells; silkworm cells; and Xenopus egg cells.

In the case of using prokaryotic cells as the host cells, the expression vectors used may have an origin that permits replication in the prokaryotic cells, a promoter, a ribosomal binding site, a multicloning site, a terminator, a drug resistance gene, an auxotrophic complementary gene, etc. Examples of expression vectors for E. coli can include pUC series, pBluescript II, pET expression systems, and pGEX expression systems. The DNAs encoding the above polypeptides can be incorporated into such expression vectors, with which prokaryotic host cells are then transformed, followed by culture of the obtained transformants so that the polypeptides encoded by the DNAs are expressed in the prokaryotic host cells. In this respect, the polypeptides may be expressed as fusion proteins with other proteins.

In the case of using eukaryotic cells as the host cells, expression vectors for eukaryotic cells having a promoter, a splicing region, a poly(A) addition site, etc. may be used as the expression vectors. Examples of such expression vectors can include pKA1, pCDM8, pSVK3, pMSG, pSVL, pBK-CMV, pBK-RSV, EBV, pRS, pcDNA3, and pYES2 vectors. In the same way as above, the DNAs encoding the above polypeptides can be incorporated into such expression vectors, with which eukaryotic host cells are then transformed, followed by culture of the obtained transformants so that the polypeptides encoded by the DNAs are expressed in the eukaryotic host cells. In the case of using expression vectors such as pIND/V5-His, pFLAG-CMV-2, pEGFP-N1, or pEGFP-C1, the polypeptides may be expressed as various fusion proteins tagged with His tag (e.g., $(His)_6$ to $(His)_{10}$), FLAG tag, myc tag, HA tag, GFP, or the like.

The expression vectors can be introduced into the host cells using well known methods such as electroporation, a calcium phosphate method, a liposome method, a DEAE dextran method, microinjection, viral infection, lipofection, and binding with cell-penetrating peptides.

The polypeptide of interest can be isolated and purified from the host cells by a combination of separation operations known in the art. Examples thereof include, but not limited to, treatment with a denaturant (e.g., urea) or a surfactant, ultrasonication, enzymatic digestion, salting-out, solvent fractionation and precipitation, dialysis, centrifugation, ultrafiltration, gel filtration, SDS-PAGE, isoelectric focusing electrophoresis, ion-exchange chromatography, hydrophobic chromatography, affinity chromatography, and reverse-phase chromatography.

In order to prepare the antibody according to the present invention, antigens thus prepared can be used as sensitizing antigens as described later.

<Structure of Antibody>

Antibodies (immunoglobulin) are usually heteromultimeric glycoproteins each comprising at least two heavy chains and two light chains. The immunoglobulins, except for IgM, are heterotetrameric glycoproteins of approximately 150 kDa each composed of two identical light (L) chains and two identical heavy (H) chains. Typically, each light chain is connected to a heavy chain via a single covalent disulfide bond, though the number of disulfide bonds between heavy chains varies among different immunoglobulin isotypes. Each of the heavy and light chains also has an intrachain disulfide bond. Each heavy chain has a variable domain (VH region) at one end, followed by a series of constant regions. Each light chain has a variable domain (VL region) at one end and has a single constant region at the other end. The light chain constant region is aligned with the first heavy chain constant region, while the light chain variable domain is aligned with the heavy chain variable domain. Particular regions called complementarity determining regions (CDRs) in the antibody variable domains exhibit specific variability and impart binding specificity to the antibody. Portions relatively conserved in the variable regions are called framework regions (FRs). The complete heavy and light chain variable domains each comprise four FRs connected via three CDRs. These three CDRs are called CDRH1, CDRH2, and CDRH3 in this order from the N-terminus of the heavy chain. Likewise, the CDRs are called CDRL1, CDRL2, and CDRL3 in the light chain. CDRH3 is most important for the binding specificity of the antibody for its antigen. In addition, CDRs in each chain are kept close to each other by the FR regions and contribute to the formation of an antigen-binding site in the antibody, together with CDRs in the other chain. The constant regions do not directly contribute to antibody-antigen binding, but exhibit various effector functions, for example, involvement in antibody-dependent cellular cytotoxicity (ADCC), phagocytosis mediated by binding to an Fcy receptor, half-life/clearance rate mediated by a neonatal Fc receptor (FcRn), and complement-dependent cytotoxicity (CDC) mediated by a C1q component in the complement cascade.

<Preparation of Antibody>

The anti-CAPRIN-1 antibody according to the present invention means an antibody having immunological reactivity with a full-length CAPRIN-1 protein or a fragment thereof. Particularly, the anti-CAPRIN-1 antibody of the present invention is an antibody immunologically binding to a partial polypeptide of a CAPRIN-1 protein (partial CAPRIN-1 polypeptide) that is a peptide containing an epitope and consisting of the amino acid sequence shown by SEQ ID NO: 5 or a polypeptide consisting of an amino acid sequence having 80% or higher, preferably 85% or higher, more preferably 90% or higher, further preferably 95% or higher sequence identity to the amino acid sequence. The antibody of the present invention preferably recognizes an epitope consisting of approximately 7 to 12 consecutive amino acids, for example, 8 to 11 consecutive amino acids, in the amino acid sequence shown by SEQ ID NO: 5 or an amino acid sequence having 80% or higher, preferably 85% or higher, more preferably 90% or higher, further preferably 95% or higher sequence identity to the amino acid sequence. This anti-CAPRIN-1 antibody of the present invention can specifically bind to the full-length CAPRIN-1 protein. The antibody of the present invention can be obtained by selecting an antibody immunologically binding to a polypeptide consisting of the amino acid sequence shown by SEQ ID NO: 5 or a polypeptide consisting of an amino acid sequence having 80% or higher, preferably 85% or higher, more preferably 90% or higher, further preferably 95% or higher sequence identity to the amino acid sequence, according to a routine method from among antibodies obtained with CAPRIN-1 proteins or fragments thereof as antigens.

In this context, the "immunological reactivity" means the property of the antibody binding to the CAPRIN-1 antigen (a full-length CAPRIN-1 protein or a partial polypeptide thereof) in vivo. Via such binding of the antibody of the present invention to the CAPRIN-1, the antibody exerts the function of damaging (e.g., killing, suppressing, or regressing) tumor cells. The antibody of the present invention can damage tumors such as breast cancer, kidney cancer, pancreatic cancer, colorectal cancer (e.g. colon cancer), lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma as a result of binding to the CAPRIN-1 protein.

The antibody of the present invention may be any type of antibody. Examples of the type of the antibody according to the present invention include monoclonal antibodies, polyclonal antibodies, synthetic antibodies, multispecific antibodies, human antibodies, humanized antibodies, chimeric antibodies, single-chain antibodies, and antibody fragments (e.g., Fab, F(ab')$_2$, and Fv). Also, the antibody is any class of immunoglobulin molecule, for example, IgG, IgE, IgM, IgA, IgD, or IgY, or any subclass, for example, IgG1, IgG2, IgG3, IgG4, IgA1, or IgA2.

Further the antibody may be modified by acetylation, formylation, amidation, phosphorylation, PEGylation, or the like, as well as glycosylation.

Hereinafter, preparation examples of various antibodies will be shown.

When the antibody of the present invention is a monoclonal antibody, for example, breast cancer cell lines SK-BR-3 expressing CAPRIN-1 is administered to each mouse for immunization. The spleen is extracted from this mouse. After separation of spleen cells, the cells are fused with mouse myeloma cells. Clones producing antibodies having a cancer cell growth inhibitory effect are selected from among the obtained fusion cells (hybridomas). Alternatively, clones producing antibodies binding to a polypeptide consisting of the amino acid sequence shown by SEQ ID NO: 5 or a polypeptide consisting of an amino acid sequence having 80% or higher sequence identity to the amino acid sequence may be selected. The hybridomas producing monoclonal antibodies having a cancer cell growth inhibitory effect or the hybridomas producing monoclonal antibodies against the polypeptides of SEQ ID NO: 5, etc. are isolated and cultured. The antibody of the present invention can be prepared by purification from the culture supernatant according to a general affinity purification method.

The monoclonal antibody-producing hybridomas may be prepared, for example, as follows. First, animals are immunized with sensitizing antigens according to a method known in the art. This immunization method generally involves intraperitoneally or subcutaneously injecting the sensitizing antigens to mammals. Specifically, the sensitizing antigens are diluted with or suspended in PBS (phosphate-buffered saline), physiological saline, or the like into an appropriate amount and then mixed, if desired, with an appropriate amount of a conventional adjuvant, for example, a complete Freund's adjuvant. After emulsification, it is administered to each mammal several times every 4 to 21 days. Alternatively, an appropriate carrier may be used for the immunization with sensitizing antigens.

After confirmation of a rise in the level of the desired antibody in the serum of the animal (typically, mammal) thus immunized, immunocytes are collected from the animal and subjected to cell fusion. Preferred examples of the immunocytes particularly include spleen cells.

Mammalian myeloma cells, for example, can be used as partner parent cells to be fused with the immunocytes. Various cell lines known in the art, for example, P3U1 (P3-X63Ag8U1), P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (deSt. Groth, S. F. et al., J. Immunol. Methods (1980) 35, 1-21), 5194 (Trowbridge, I. S. J. Exp. Med. (1978) 148, 313-323), and R210 (Galfre, G. et al., Nature (1979) 277, 131-133), are preferably used as the myeloma cells.

The cell fusion between the immunocytes and the myeloma cells can be performed basically according to a method known in the art, for example, the method of Kohler and Milstein (Kohler, G. and Milstein, C. Methods Enzymol. (1981) 73, 3-46).

More specifically, the cell fusion is carried out, for example, in the presence of a cell fusion promoter in a conventional nutrient medium. For example, polyethylene glycol (PEG) or hemagglutinating virus of Japan (HVJ) is used as the fusion promoter. If desired, an auxiliary such as dimethyl sulfoxide may be further added in order to enhance fusion efficiency.

The ratio between the immunocytes and the myeloma cells used can be arbitrarily set. For example, the amount of the immunocytes is preferably set to 1 to 10 times the amount of the myeloma cells. Examples of the medium that can be used in the cell fusion include RPMI1640 and MEM media suitable for the growth of the myeloma cell lines as well as conventional media for use in this type of cell culture. In addition, a serum supplement such as fetal calf serum (FCS) may be used in combination with this media.

For the cell fusion, the immunocytes and the myeloma cells are well mixed in a predetermined amount of the medium. A PEG solution (average molecular weight: for example, approximately 1000 to 6000) preheated to approximately 37° C. is usually added to the mixture at a concentration of 30 to 60% (w/v) and mixed therewith to form the hybridomas of interest. Subsequently, procedures of sequentially adding an appropriate medium and removing the supernatant by centrifugation are preferably repeated to remove cell fusion agents or the like unfavorable for the growth of the hybridomas.

The hybridomas thus obtained are cultured in a conventional selective medium, for example, a HAT medium (medium containing hypoxanthine, aminopterin, and thymidine) for selection. Culture in the HAT medium is continued for a period (usually, several days to several weeks) sufficient for the death of cells (non-fused cells) other than the hybridomas of interest. Subsequently, hybridomas producing the antibody of interest are screened for and cloned as single clones by a conventional limiting dilution method.

In addition to such obtainment of the hybridomas by the immunization of non-human animals with antigens, hybridomas producing human antibodies having the desired activity (e.g., cell growth inhibitory activity) may be obtained by sensitizing human lymphocytes, for example, EB virus-infected human lymphocytes, with proteins, protein-expressing cells, or lysates thereof in vitro and fusing the sensitized lymphocytes with human-derived myeloma cells capable of dividing permanently, for example, U266 (Accession No. TIB 196).

The monoclonal antibody-producing hybridomas thus prepared can be subcultured in a conventional medium and can also be stored for a long period in liquid nitrogen.

Specifically, the desired antigens or cells expressing the desired antigens are used as sensitizing antigens in immunization according to a conventional immunization method. The obtained immunocytes are fused with parent cells known in the art according to a conventional cell fusion method. Monoclonal antibody-producing cells (hybridomas) can be screened for by a conventional screening method to prepare the hybridomas producing monoclonal antibodies of interest.

Another example of the antibody that may be used in the present invention is a polyclonal antibody. The polyclonal antibody can be obtained, for example, as follows:

Serum is obtained from small animals such as mice, human antibody-producing mice, or rabbits immunized with natural CAPRIN-1 proteins or recombinant CAPRIN-1 proteins expressed as fusion proteins with GST or the like in microorganisms such as *E. coli*, or partial peptides thereof. Alternatively, serum may be obtained from mammals immunized with CAPRIN-1 fragment polypeptides each comprising the amino acid sequence shown by SEQ ID NO: 5 or an amino acid sequence having 80% or higher, preferably 85% or higher, more preferably 90% or higher, further preferably 95% or higher sequence identity to the amino acid sequence (preferably, a polypeptide consisting of the amino acid sequence of SEQ ID NO: 5), or polypeptides each comprising (preferably, consisting of) an epitope consisting of approximately 7 to 12 consecutive amino acids, for example, 8 to 11 consecutive amino acids, in the amino acid sequence shown by SEQ ID NO: 5 or an amino acid sequence having 80% or higher, preferably 85% or higher, more preferably 90% or higher, further preferably 95% or higher sequence identity to the amino acid sequence, as sensitizing antigens. These serums are purified using, for example, ammonium sulfate precipitation, protein A or protein G columns, DEAE ion-exchange chromatography, or affinity columns coupled with CAPRIN-1 proteins or synthetic peptides to prepare the anti-CAPRIN-1 polyclonal antibody. The polyclonal antibody of the present invention includes antibodies obtained from human antibody-producing animals (e.g., mice) immunized with CAPRIN-1 proteins.

In this context, for example, KM mice (Kirin Pharma Co., Ltd./Medarex) and Xeno mice (Amgen Inc.) are known as the human antibody-producing mice (e.g., International Publication Nos. WO02/43478 and WO02/092812). Complete human polyclonal antibodies can be obtained from the blood of such mice immunized with CAPRIN-1 proteins or fragments thereof. Alternatively, spleen cells may be isolated from the mice thus immunized and fused with myeloma cells. In this way, human monoclonal antibodies can be obtained.

The antigens can be prepared according to, for example, a method using animal cells (JP Patent Publication (Kohyo) No. 2007-530068 A (2007)) or a method using baculovirus (e.g., International Publication No. WO98/46777). Antigens having low immunogenicity can be bound to immunogenic macromolecules such as albumin for immunization. Antigens may be administered with adjuvants for immunization.

Alternatively, the antibody of the present invention may be obtained as recombinant antibodies, which are produced using a genetic engineering technique which involves: cloning the antibody genes from hybridomas; incorporating the antibody genes into appropriate vectors; and introducing the vectors into hosts (see, e.g., Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, antibody variable region (V region) cDNAs are synthesized from the mRNAs of hybridomas using reverse transcriptase. After obtainment of DNAs encoding the antibody V regions of interest, the DNAs are ligated with DNAs encoding the desired antibody constant regions (C regions). The resulting ligation products are incorporated into expression vectors. Alternatively, the antibody V region-encoding DNAs may be incorporated into expression vectors containing antibody C region DNAs. These DNAs are incorporated into the expression vectors so as to be expressed under the control of expression control regions, for example, an enhancer and a promoter. Next, host cells can be transformed with the resulting expression vectors and allowed to express antibodies.

The anti-CAPRIN-1 antibody of the present invention is preferably a monoclonal antibody. Alternatively, the anti-CAPRIN-1 antibody of the present invention may be a polyclonal antibody, a genetically engineered antibody (chimeric antibody, humanized antibody, etc.), or the like.

The monoclonal antibody includes human monoclonal antibodies, non-human animal monoclonal antibodies (e.g., mouse, rat, rabbit, and chicken monoclonal antibodies), chimeric monoclonal antibodies, and the like. The monoclonal antibody may be prepared by the culture of hybridomas obtained by the fusion between spleen cells from non-human animals (e.g., mice or human antibody-producing mice, chickens, and rabbits) immunized with CAPRIN-1 proteins or fragments thereof and myeloma cells. Alternatively, genes of heavy and light chain variable regions from the spleen cells of non-human animals (e.g., mice, human antibody-producing mice, chickens, and rabbits) immunized with CAPRIN-1 proteins or fragments thereof may be incorporated via linkers into phagemid vectors, which are then introduced into *E. coli* so that single-chain antibodies are expressed via helper phages to prepare the antibodies of interest. The chimeric antibody is an antibody prepared from a combination of sequences derived from different animals and is, for example, an antibody composed of mouse antibody heavy and light chain variable regions and human antibody heavy and light chain constant regions. The chimeric antibody can be prepared using a method known in the art which involves, for example: ligating DNAs encoding the antibody V regions with DNAs encoding human antibody C regions; incorporating the resulting ligation products into expression vectors; and introducing the vectors into hosts so that antibodies are produced.

Monoclonal antibodies that have immunological reactivity with a partial CAPRIN-1 polypeptide consisting of the amino acid sequence shown by SEQ ID NO: 5 and have an antitumor effect are prepared by methods described later in Examples. These monoclonal antibodies each comprise, for example, a heavy chain variable (VH) region having the amino acid sequence of SEQ ID NO: 9, 19, 58, 63, 69, or 77 and a light chain variable (VL) region having the amino acid sequence of SEQ ID NO: 13, 23, 53, 62, 65, 73, or 81. In these monoclonal antibodies, the VH region can comprise CDR1 shown by the amino acid sequence of SEQ ID NO: 6, 16, 55, 66, or 74, CDR2 shown by the amino acid sequence of SEQ ID NO: 7, 17, 56, 67, or 75, and CDR3 shown by the amino acid sequence of SEQ ID NO: 8, 18, 57, 68, or 76, and the VL region can comprise CDR1 shown by the amino acid sequence of SEQ ID NO: 10, 20, 50, 59, 70, or 78, CDR2 shown by the amino acid sequence of SEQ ID NO: 11, 21, 51, 60, 64, 71, or 79, and CDR3 shown by the amino acid sequence of SEQ ID NO: 12, 22, 52, 61, 72, or 80.

The humanized antibody, also called reshaped human antibody, is an engineered antibody. The humanized antibody is constructed by grafting antibody CDRs derived from an immunized animal into the complementarity determining regions of a human antibody. A general gene recombination approach therefor is also known.

Specifically, for example, DNA sequences designed so as to link mouse, rabbit, and chicken antibodies CDRs and human antibody framework regions (FRs) are synthesized by PCR using several prepared oligonucleotides having terminal portions overlapping with each other. The obtained DNAs are ligated with DNAs encoding human antibody constant regions. Subsequently, the resulting ligation products are incorporated into expression vectors, which are then introduced into hosts for antibody production to obtain the antibody of interest (see European Patent Application Publication No. EP239400 and International Publication No. WO96/02576). The human antibody FRs connected via CDRs are selected such that the complementarity determining regions form a favorable antigen-binding site. If necessary, amino acids in the framework regions of antibody variable regions may be substituted such that the complementarity determining regions of the resulting reshaped human antibody form an appropriate antigen-binding site (Sato K. et al., Cancer Research 1993, 53: 851-856). In addition, these framework regions may be replaced with framework regions derived from various human antibodies (see International Publication No. WO99/51743).

The human antibody framework regions connected via CDRs are selected such that the complementarity determining regions form a favorable antigen-binding site. If necessary, amino acids in the framework regions of antibody variable regions may be substituted such that the complementarity determining regions of the resulting reshaped human antibody form an appropriate antigen-binding site (Sato K. et al., Cancer Research 1993, 53: 851-856).

Amino acids in variable regions (e.g., FRs) or constant regions of the chimeric antibody or the humanized antibody thus prepared may be substituted, for example, by other amino acids.

The amino acid substitution is the substitution of, for example, less than 15, less than 10, 8 or less, 7 or less, 6 or less, 5 or less, 4 or less, 3 or less, or 2 or less amino acids, preferably 1 to 5 amino acids, more preferably 1 or 2 amino acids. The substituted antibody should be functionally equivalent to an unsubstituted antibody. The substitution is desirably conservative amino acid substitution, which is the substitution between amino acids similar in properties such as charge, side chains, polarity, and aromaticity. The amino acids can be classified in terms of similar properties into, for example: basic amino acids (arginine, lysine, and histidine); acidic amino acids (aspartic acid and glutamic acid); uncharged polar amino acids (glycine, asparagine, glutamine, serine, threonine, cysteine, and tyrosine); nonpolar amino acids (leucine, isoleucine, alanine, valine, proline, phenylalanine, tryptophan, and methionine); branched amino acids (leucine, valine, and isoleucine); and aromatic amino acids (phenylalanine, tyrosine, tryptophan, and histidine).

Examples of modified antibodies can include antibodies bound with various molecules such as polyethylene glycol (PEG). In the modified antibody of the present invention, the substance to be bound is not limited. In order to obtain such a modified antibody, the obtained antibody can be chemically modified. A method therefor has already been established in the art.

In this context, the phrase "functionally equivalent" means that an antibody concerned has biological or biochemical activity similar to that of the antibody of the present invention, specifically, the antibody concerned has the function of damaging tumor and essentially causes no rejection when applied to humans, for example. Examples of such activity can include cell growth inhibitory activity and binding activity.

A method for preparing a polypeptide functionally equivalent to a certain polypeptide, which involves introducing a mutation into a polypeptide, is well known to those skilled in the art. For example, those skilled in the art can introduce a mutation as appropriate into the antibody of the present invention using site-directed mutagenesis (Hashimoto-Gotoh, T. et al., (1995) Gene 152, 271-275; Zoller, M J., and Smith, M. (1983) Methods Enzymol. 100, 468-500; Kramer, W. et al., (1984) Nucleic Acids Res. 12, 9441-9456; Kramer, W. and Fritz, H J., (1987) Methods Enzymol. 154, 350-367; Kunkel, T A., (1985) Proc. Natl. Acad. Sci. USA. 82, 488-492; and Kunkel (1988) Methods Enzymol. 85, 2763-2766) or the like, thereby prepare an antibody functionally equivalent to the antibody of the present invention.

An antibody that recognizes an epitope of a CAPRIN-1 protein described above or a CAPRIN-1 polypeptide fragment including thereof can be obtained by a method generally known to those skilled in the art. For example, the antibody can be obtained by a method which involves determining the epitope of the CAPRIN-1 protein recognized by the anti-CAPRIN-1 antibody having a cancer cell growth inhibitory effect obtained by the above by a conventional method (e.g., epitope mapping or a method for identifying an epitope as described later) and preparing an antibody using a polypeptide having an amino acid sequence contained in the epitope as an immunogen, or a method which involves determining an epitope for an antibody prepared by a conventional method and selecting an antibody that recognizes the same epitope as that for the anti-CAPRIN-1 antibody. In this context, the "epitope" refers to a polypeptide fragment having antigenicity or immunogenicity in mammals, preferably humans. Its smallest unit consists of approximately 7 to 12 amino acids, preferably 8 to 11 amino acids.

The antibody of the present invention is an antibody having immunological reactivity with CAPRIN-1, an antibody specifically recognizing CAPRIN-1, or an antibody specifically binding to CAPRIN-1 and exhibits cytotoxic activity or tumor growth inhibitory effect on cancer. The antibody preferably has a structure that causes little or no rejection in recipient animals. Examples of such antibodies include human antibodies, humanized antibodies, chimeric antibodies (e.g., human-mouse chimeric antibodies), single-chain antibodies, and bispecific antibodies when the recipient animals are humans. These antibodies have heavy and light chain variable regions derived from a human antibody or have heavy and light chain variable regions consisting of complementarity determining regions (CDR1, CDR2, and CDR3) derived from a non-human animal antibody and framework regions derived from a human antibody. Alternatively, these antibodies are recombinant antibodies having heavy and light chain variable regions derived from a non-human animal antibody and heavy and light chain constant regions derived from a human antibody. The antibody of the present invention is preferably the former two antibodies.

Such recombinant antibodies can be prepared as follows: DNAs encoding monoclonal antibodies (e.g., human, mouse, rat, rabbit, and chicken monoclonal antibodies) against human CAPRIN-1 are cloned from the antibody-producing cells such as hybridomas and used as templates to prepare DNAs encoding the light and heavy chain variable regions of the antibodies by RT-PCR or the like. The respective sequences of the light and heavy chain variable regions and the respective sequences of CDR1, CDR2, and CDR3 in each region are determined on the basis of the Kabat EU numbering system (Kabat et al., Sequences of Proteins of Immunological Interest, 5th Ed. Public Health Service, National Institute of Health, Bethesda, Md. (1991)).

A DNA encoding each variable region or a DNA encoding each CDR is prepared using a genetic engineering technique (Sambrook et al., Molecular Cloning A Laboratory Manual, Cold Spring Harbor Laboratory Press (1989)) or a DNA synthesizer. The above-mentioned human monoclonal antibody-producing hybridomas can be prepared by immunizing human antibody-producing animals (e.g., mice) with human CAPRIN-1 and then fusing spleen cells excised from the immunized animals with myeloma cells. Separately, DNAs encoding light or heavy chain variable and constant regions derived from a human antibody are prepared, if necessary, using a genetic engineering technique or a DNA synthesizer.

For the humanized antibody, a DNA encoding the humanized antibody can be prepared by producing DNAs in which the CDR coding sequences in DNAs encoding a human antibody-derived light or heavy chain variable regions are substituted by corresponding CDR coding sequences of a non-human animal (e.g., mouse, rat, rabbit, or chicken)-derived antibody, ligating the resulting DNAs with the DNAs encoding human antibody-derived light or heavy chain constant regions, respectively.

For the chimeric antibody, a DNA encoding the chimeric antibody can be prepared by ligating DNAs encoding light or heavy chain variable regions of a non-human animal (e.g., mouse, rat, rabbit, or chicken)-derived antibody with DNAs encoding human antibody-derived light or heavy chain constant regions.

The single-chain antibody means an antibody in which heavy and light chain variable regions are linearly linked to each other via a linker. A DNA encoding the single-chain antibody can be prepared by ligating a DNA encoding the heavy chain variable region, a DNA encoding the linker, and a DNA encoding the light chain variable region. In this context, the heavy and light chain variable regions are both derived from a human antibody or derived from a human antibody in which CDRs alone are substituted by CDRs of a non-human animal (e.g., mouse, rat, rabbit, or chicken)-derived antibody. The linker consists of 12 to 19 amino acids. Examples thereof include $(G_4S)_3$ consisting of 15 amino acids (G. B. Kim et al., Protein Engineering Design and Selection 2007, 20 (9): 425-432).

The bispecific antibody (diabody) means an antibody capable of specifically binding to two different epitopes. A DNA encoding the bispecific antibody can be prepared by, for example, ligating a DNA encoding a heavy chain variable region A, a DNA encoding a light chain variable region B, a DNA encoding a heavy chain variable region B, and a DNA encoding a light chain variable region A in this order, wherein the DNA encoding the light chain variable region B and the DNA encoding the heavy chain variable region B are ligated via a DNA encoding a linker as described above. In this context, the heavy and light chain variable regions are all derived from a human antibody or derived from a human antibody in which CDRs alone are substituted by CDRs of a non-human animal (e.g., mouse, rat, rabbit, or chicken)-derived antibody.

The recombinant DNAs thus prepared can be incorporated into one or more appropriate vectors, which are then introduced into host cells (e.g., mammalian cells, yeast cells, and insect cells), and the DNAs are (co)expressed to produce recombinant antibodies (see, P. J. Delves., ANTIBODY PRODUCTION ESSENTIAL TECHNIQUES, 1997 WILEY, P. Shepherd and C. Dean, Monoclonal Antibodies, 2000 OXFORD UNIVERSITY PRESS; and J. W. Goding, Monoclonal Antibodies: principles and practice, 1993 ACADEMIC PRESS).

Examples of the antibody of the present invention prepared by any of the methods described above include the following antibodies (a) to (g) obtained in Examples described later:

(a) an antibody comprising a heavy chain variable region comprising complementarity determining regions of SEQ ID NOs: 6, 7, and 8 and a light chain variable region comprising complementarity determining regions of SEQ ID NOs: 10, 11, and 12 (e.g., an antibody having a heavy chain variable region of SEQ ID NO: 9 and a light chain variable region of SEQ ID NO: 13);

(b) an antibody comprising a heavy chain variable region comprising complementarity determining regions of SEQ ID NOs: 16, 17, and 18 and a light chain variable region comprising complementarity determining regions of SEQ ID NOs: 20, 21, and 22 (e.g., an antibody constructed using a heavy chain variable region of SEQ ID NO: 19 and a light chain variable region of SEQ ID NO: 23);

(c) an antibody comprising a heavy chain variable region comprising complementarity determining regions of SEQ ID NOs: 6, 7, and 8 and a light chain variable region comprising complementarity determining regions of SEQ ID NOs: 50, 51, and 52 (e.g., an antibody constructed using a heavy chain variable region of SEQ ID NO: 9 and a light chain variable region of SEQ ID NO: 53);

(d) an antibody comprising a heavy chain variable region comprising complementarity determining regions of SEQ ID NOs: 55, 56, and 57 and a light chain variable region comprising complementarity determining regions of SEQ ID NOs: 59, 60, and 61 (e.g., an antibody constructed using a heavy chain variable region of SEQ ID NO: 58 and a light chain variable region of SEQ ID NO: 62);

(e) an antibody comprising a heavy chain variable region comprising complementarity determining regions of SEQ ID NOs: 55, 56, and 57 and a light chain variable region comprising complementarity determining regions of SEQ ID NOs: 59, 64, and 61 (e.g., an antibody constructed using a heavy chain variable region of SEQ ID NO: 63 and a light chain variable region of SEQ ID NO: 65);

(f) an antibody comprising a heavy chain variable region comprising complementarity determining regions of SEQ ID NOs: 66, 67, and 68 and a light chain variable region comprising complementarity determining regions of SEQ ID NOs: 70, 71, and 72 (e.g., an antibody constructed using a heavy chain variable region of SEQ ID NO: 69 and a light chain variable region of SEQ ID NO: 73);

(g) an antibody comprising a heavy chain variable region comprising complementarity determining regions of SEQ ID NOs: 74, 75, and 76 and a light chain variable region comprising complementarity determining regions of SEQ ID NOs: 78, 79, and 80 (e.g., an antibody constructed using a heavy chain variable region of SEQ ID NO: 77 and a light chain variable region of SEQ ID NO: 81);

In this context, the amino acid sequences shown by SEQ ID NOs: 6, 7, and 8, and SEQ ID NOs: 16, 17, and 18 correspond to CDR1, CDR2, and CDR3, respectively, of a mouse antibody-derived heavy chain variable region. The amino acid sequences shown by SEQ ID NOs: 10, 11, and 12, SEQ ID NOs: 20, 21, and 22, and SEQ ID NOs: 50, 51, and 52 correspond to CDR1, CDR2, and CDR3, respectively, of a mouse antibody-derived light chain variable region. The amino acid sequences shown by SEQ ID NOs: 55, 56, and 57, SEQ ID NOs: 66, 67, and 68, and SEQ ID NOs: 74, 75, and 76 correspond to CDR1, CDR2, and CDR3, respectively, of a chicken antibody-derived heavy chain variable region. The amino acid sequences shown by SEQ ID NOs: 59, 60, and 61, SEQ ID NOs: 59, 64, and 61, SEQ ID NOs: 70, 71, and 72, and SEQ ID NOs: 78, 79, and 80 correspond to CDR1, CDR2, and CDR3, respectively, of a chicken antibody-derived light chain variable region.

Examples of the humanized antibody, the chimeric antibody, the single-chain antibody, or the bispecific antibody of the present invention include antibodies described below. The following antibodies are illustrative embodiments of the antibody (a), but there may be also similar embodiments of the other antibodies (b) to (g).

(i) an antibody comprising a heavy chain variable region comprising the amino acid sequences of SEQ ID NOs: 6, 7, and 8 and the amino acid sequences of human antibody-derived framework regions and a light chain variable region comprising the amino acid sequences of SEQ ID NOs: 10, 11, and 12 and the amino acid sequences of human antibody-derived framework regions.

(ii) an antibody comprising a heavy chain variable region comprising the amino acid sequences of SEQ ID NOs: 6, 7, and 8 and the amino acid sequences of human antibody-derived framework regions, a heavy chain constant region comprising a human antibody-derived amino acid sequence, a light chain variable region comprising the amino acid sequences of SEQ ID NOs: 10, 11, and 12 and the amino acid sequences of human antibody-derived framework regions, and a light chain constant region comprising a human antibody-derived amino acid sequence.

(iii) an antibody comprising a heavy chain variable region comprising the amino acid sequence of SEQ ID NO: 9, a heavy chain constant region comprising a human antibody-derived amino acid sequence, a light chain variable region comprising the amino acid sequence of SEQ ID NO: 13, and a light chain constant region comprising a human antibody-derived amino acid sequence.

The sequences of the constant and variable regions of human antibody heavy and light chains are available from, for example, NCBI (USA; GenBank, UniGene, etc.). For example, the following sequences can be referred to: Accession No. J00228 for a human IgG1 heavy chain constant region; Accession No. J00230 for a human IgG2 heavy chain constant region; Accession No. X03604 for a human IgG3 heavy chain constant region; Accession No. K01316 for a human IgG4 heavy chain constant region; Accession Nos. V00557, X64135, and X64133 for a human light chain κ constant region; and Accession Nos. X64132 and X64134 for a human light chain λ constant region.

Preferably, these antibodies have cytotoxic activity and can thereby exert an antitumor effect.

The above particular sequences of the heavy and light chain variable regions and CDRs in the above-mentioned antibodies are provided merely for illustrative purposes, and it is clear that the antibody of the present invention is not limited by the particular sequences. Hybridomas capable of producing anti-human CAPRIN-1 human antibodies or non-human animal antibodies (e.g., mouse antibodies) different from those specifically described above are prepared, and monoclonal antibodies produced by the hybridomas are recovered and it is determined whether or not the recovered antibodies are the antibodies of interest using the immunological binding activity against human CAPRIN-1 and cytotoxic activity as indicators. The monoclonal antibody-producing hybridomas of interest are thereby identified. Then, DNAs encoding heavy and light chain variable regions of the antibodies of interest are prepared from the hybridomas and sequenced, as described above. The DNAs are used for the preparation of different antibodies.

The antibody described above may be any of the antibodies (a) to (g), etc. having the substitution, deletion, or addition of one or several amino acids, in particular, in a region other than CDRs, for example, in a framework region sequence and/or a constant region sequence, as long as the antibody has such specificity that it can specifically recognize CAPRIN-1. Herein, the term "several" preferably means 2 to 5, more preferably 2 or 3.

The antibody of the present invention has an affinity constant Ka ($k_{on}/k_{off}$) of preferably at least $10^7$ M$^{-1}$, at least $10^8$ M$^{-1}$, at least $5\times10^8$ M$^{-1}$, at least $10^9$ M$^{-1}$, at least $5\times10^9$ M$^{-1}$, at least $10^{10}$ at least $5\times10^{10}$ M$^{-1}$, at least $10^{11}$ M$^{-1}$, at least $5\times10^{11}$ M$^{-1}$, at least $10^{12}$ M$^{-1}$, or at least $10^{13}$ M$^{-1}$ for the CAPRIN-1 protein or the fragment thereof.

The antibody of the present invention can be conjugated with an antitumor agent. The conjugation of the antibody with the antitumor agent can be performed via a spacer having a group reactive with an amino group, a carboxyl group, a hydroxy group, a thiol group, or the like (e.g., a succinimidyl group, a formyl group, a 2-pyridyldithio group, a maleimidyl group, an alkoxycarbonyl group, or a hydroxy group).

Examples of the antitumor agent include the following antitumor agents known by literatures, etc.: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethylenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, Adriamycin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens (e.g., calusterone, dromostanolone propionate, epitiostanol, mepitiostane, and testolactone), aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocin, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridin A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, Xeloda, ibandronate, irinotecan, topoisomerase inhibitors, difluoromethylornithine (DMFO), retinoic acid, capecitabine, and pharmaceutically acceptable salts and derivatives thereof.

Alternatively, the antibody of the present invention can be administered in combination with an antitumor agent to produce a higher therapeutic effect. This approach is adaptable to a patient with a cancer expressing CAPRIN-1 either before or after surgical operation. This approach can be applied, particularly after surgery, to CAPRIN-1-expressing cancer, which has been treated conventionally with an antitumor agent alone, to produce higher prevention of cancer recurrence or prolongation of survival time.

Examples of the antitumor agent used in the combined administration with the antibody of the present invention include the following antitumor agents known by literatures, etc.: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethylenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, Adriamycin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocin, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridin A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, Xeloda, ibandronate, irinotecan, topoisomerase inhibitors, difluoromethylornithine (DMFO), retinoic acid, capecitabine, and pharmaceutically acceptable salts (known in the art) and derivatives (known in the art) thereof. Of these antitumor agents, cyclophosphamide, paclitaxel, docetaxel, or vinorelbine is particularly preferably used.

The antibody of the present invention may be bound to a radioisotope known by literatures, etc., such as $^{211}$At, $^{131}$I, $^{125}$I, $^{90}$Y, $^{186}$Re, $^{188}$Re, $^{153}$Sm, $^{212}$Bi, $^{32}$P, $^{175}$Lu, or $^{176}$Lu. Preferably, a radioisotope effective for the treatment or diagnosis of tumor is used. Such a radioisotope is also included in the scope of the antitumor agent according to the present invention.

<Identification of Epitope>

The antibody of the present invention recognizes the amino acid sequence shown by SEQ ID NO: 5 as an epitope, as shown below in Examples. One example of a method for confirming the epitope for the antibody of the present invention comprises immobilizing the polypeptide of SEQ ID NO: 5 (epitope) onto a plate and evaluating the antibody for its reactivity against this epitope. Specifically, the polypeptide of SEQ ID NO: 5 is immobilized onto a plate through reaction with an electrophilic functional group attached via a spacer of e.g., oligoethylene glycol to the plate, and then reacted with the antibody of the present invention. For example, a HRP (horseradish peroxidase)-labeled secondary antibody capable of binding to the antibody of the present invention can be reacted therewith to evaluate the reactivity of the antibody (to confirm the epitope for the antibody of the present invention). The polypeptide of SEQ ID NO: 5 to be immobilized on a plate may be used as a form consisting of the sequence of SEQ ID NO: 5 or a partially modified form (e.g., a modified form of the polypeptide at the N- or C-terminal residue with any several amino acids or a protein such as KLH or a modified form of the polypeptide with a MAP protein), as long as the antibody of the present invention binds to these polypeptide forms.

Some antibodies of the present invention may not react with the polypeptide of SEQ ID NO: 5 (i.e., the epitope not being confirmed) in the above method. In such a case, the epitope for the antibody of the present invention can be confirmed by reacting the antibody with the antigen under solution conditions that facilitate antigen-antibody binding as described in Example 2, obtaining the resulting antigen-antibody complex by an immunoprecipitation method, and then separating a polypeptide moiety bound to the antibody, and determining its amino acid sequence. The antigen may be a polypeptide consisting of the sequence of SEQ ID NO: 5, its partially modified one, or a CAPRIN-1 protein as long as an epitope reactive with the antibody of the present invention can be confirmed therefor by the above-mentioned methods.

<Antitumor Effect>

It is considered that the antitumor effect of the anti-CAPRIN-1 antibody to be used in the present invention on CAPRIN-1-expressing cancer cells is brought about by the following mechanism: Antibody-dependent effector cell-mediated cytotoxicity (ADCC) against the CAPRIN-1-expressing cells and complement-dependent cytotoxicity (CDC) against the CAPRIN-1-expressing cells. However, the scope of the present invention is not intended to be limited by the mechanism.

The antitumor effect based on the mechanism is known to correlate with the number of antibody-binding target molecules expressed on the surface of cancer cells (Niwa R., Clinical Cancer Research (2005) Mar. 15; 11 (6): 2327-2336). The number of target molecules expressed on the surface of cancer cells can be examined using an existing assay kit capable of measuring the number of molecules on cell surface. Specifically, the number of antibody-binding target molecules can be determined by: reacting cancer cells with, for example, antibodies against the target molecules as primary antibodies; reacting therewith fluorescently labeled antibodies against the primary antibodies, together with calibration curve beads with the preliminarily known number of molecules; measuring the mean fluorescence intensity of the samples; and determining the number of the target molecules on the basis of the obtained calibration curve.

Thus, the anti-CAPRIN-1 antibody to be used in the present invention can be assayed for its activity by determining ex vivo the ADCC activity or the CDC activity against CAPRIN-1-expressing cancer cells or by examining the number of CAPRIN-1 molecules expressed on the surface of cancer cells in the case of using the anti-CAPRIN-1 antibody according to the present invention as a primary antibody as specifically shown below in Examples.

The anti-CAPRIN-1 antibody to be used in the present invention binds to CAPRIN-1 proteins on cancer cells and exhibits an antitumor effect through the activity. Thus, the anti-CAPRIN-1 antibody of the present invention is considered to be useful in the treatment or prevention of cancer. Specifically, the present invention provides a pharmaceutical composition for treatment and/or prevention of cancer, comprising the anti-CAPRIN-1 antibody as an active ingredient. The anti-CAPRIN-1 antibody to be used for the purpose of administration to human bodies (antibody therapy) is preferably a human antibody or a humanized antibody for reducing immunogenicity.

The anti-CAPRIN-1 antibody with higher binding affinity for a CAPRIN-1 protein on the surface of cancer cells exerts stronger antitumor activity. Thus, the antibody according to the present invention can be expected to have a stronger antitumor effect due to the high binding affinity for the CAPRIN-1 protein, and therefore it can be used as a pharmaceutical composition for use in the treatment and/or prevention of cancer. Preferably, the antibody according to the present invention has high binding affinity with association constant (affinity constant) Ka ($K_{on}/k_{off}$) of preferably at least $10^7 M^{-1}$, at least $10^8 M^{-1}$, at least $5 \times 10^8 M^{-1}$, at least $10^9 M^{-1}$, at least $5 \times 10^9 M^{-1}$, at least $10^{10} M^{-1}$, at least $5 \times 10^{10} M^{-1}$, at least $10^{11} M^{-1}$, at least $5 \times 10^{11} M^{-1}$, at least $10^{12} M^{-1}$, or at least $10^{13} M^{-1}$, as described above.

A larger number of CAPRIN-1 molecules that can bind to anti-CAPRIN-1 antibodies on the surface of cancer cells produces stronger antitumor activity. Desirably, in order to produce the expected antitumor effect, the number of CAPRIN-1 molecules to which the antibodies bind is $10^4$ or more, preferably $10^5$ or more CAPRIN-1 molecules per cancer cell, as measured using the anti-CAPRIN-1 antibody of the present invention. Tumor (cancer cells) having a large number of CAPRIN-1 molecules on its cell surface is particularly preferred as cancer subject to the administration of the antibody of the present invention.

<Binding to Antigen-Expressing Cells>

The ability of the antibody to bind to CAPRIN-1 can be determined by use of binding assay using, for example, ELISA, Western blot, immunofluorescence, and flow cytometry analysis, as described in Examples.

<Immunohistochemical Staining>

The antibody that recognizes CAPRIN-1 can be tested for its reactivity with CAPRIN-1 by an immunohistochemical method well known to those skilled in the art using a paraformaldehyde- or acetone-fixed frozen section or paraformaldehyde-fixed paraffin-embedded tissue section of a tissue obtained from a patient during surgical operation or from a xenograft tissue-carrying animal inoculated with a cell line expressing CAPRIN-1 either spontaneously or after transfection.

For immunohistochemical staining, the antibody reactive with CAPRIN-1 can be stained by various methods. For example, the antibody can be visualized through reaction with a horseradish peroxidase-conjugated goat anti-mouse antibody, goat anti-rabbit antibody, or goat anti-chicken antibody.

<Pharmaceutical Composition, and Method for Treating and/or Preventing Cancer>

A target of the pharmaceutical composition for treatment and/or prevention of cancer of the present invention is not particularly limited as long as the target is cancer (cells) expressing a CAPRIN-1 gene.

The terms "tumor" and "cancer" used herein mean malignant neoplasm and are used interchangeably with each other.

The cancer targeted in the present invention is cancer expressing a CAPRIN-1 protein-encoding gene and is preferably breast cancer, kidney cancer, pancreatic cancer, colorectal cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma.

Specific examples of these cancers include, but not limited to, breast adenocarcinoma, complex-type breast adenocarcinoma, malignant mixed tumor of mammary gland, intraductal papillary adenocarcinoma, lung adenocarcinoma, squamous cell cancer, small-cell cancer, large-cell cancer, glioma which is tumor of neuroepithelial tissue, ventricular ependymoma, neuronal tumor, embryonal neuroectodermal tumor, neurilemmoma, neurofibroma, meningioma, chronic lymphocytic leukemia, lymphoma, gastrointestinal lymphoma, alimentary lymphoma, small to medium cell-type lymphoma, cecal cancer, ascending colon cancer, descending colon cancer, transverse colon cancer, sigmoid colon cancer, rectal cancer, epithelial ovarian cancer, germ cell tumor, stromal cell tumor, pancreatic ductal carcinoma, invasive pancreatic ductal carcinoma, pancreatic adenocarcinoma, acinar cell carcinoma, adenosquamous carcinoma, giant cell tumor, intraductal papillary-mucinous neoplasm, mucinous cystic neoplasm, pancreatoblastoma, serous cystadenocarcinoma, solid papillary tumor, gastrinoma, glucagonoma, insulinoma, multiple endocrine neoplasia type-1 (Wermer's syndrome), nonfunctional islet cell tumor, somatostatinoma, and VIPoma.

The subject (patient) as the recipient is preferably mammals, for example, mammals including primates, pet animals, livestock, and sport animals, and particularly preferably humans, dogs, and cats.

When using the antibody of the present invention in a pharmaceutical composition, the pharmaceutical composition can be formulated by a method known to those skilled in the art. For example, the pharmaceutical composition can be used in the form of a parenteral injection of an aseptic solution or suspension with water or any other pharmaceutically acceptable liquid. For example, the pharmaceutical composition may be formulated with the antibody mixed in a unit dosage form required for generally accepted pharmaceutical practice, in combination with pharmacologically acceptable carriers or media, specifically, sterilized water, physiological saline, plant oil, an emulsifier, a suspending agent, a surfactant, a stabilizer, a flavoring agent, an excipient, a vehicle, a preservative, a binder, etc, as appropriate. The amount of the active ingredient in such a preparation is determined such that an appropriate dose within the indicated range can be achieved.

An aseptic composition for injection can be formulated according to conventional pharmaceutical practice using a vehicle such as injectable distilled water.

Examples of aqueous solutions for injection include physiological saline, isotonic solutions containing glucose and other adjuvants, for example, D-sorbitol, D-mannose, D-mannitol, and sodium chloride. These solutions may be used in combination with an appropriate solubilizer, for example, an alcohol (particularly, ethanol) or a polyalcohol (e.g., propylene glycol and polyethylene glycol), or a nonionic surfactant, for example, polysorbate 80™ or HCO-60.

Examples of oily solutions include those using sesame oil or soybean oil. The solutions may be used in combination with a solubilizer such as benzyl benzoate or benzyl alcohol. A buffer (e.g., a phosphate buffer solution or a sodium acetate buffer solution), a soothing agent (e.g., procaine hydrochloride), a stabilizer (e.g., benzyl alcohol or phenol), or an antioxidant may be added to the solutions. The injection solutions thus prepared are generally charged into appropriate ampules.

The pharmaceutical composition of the present invention is administered orally or parenterally, preferably parenterally. Specific examples of its dosage forms include injections, intranasal administration agents, transpulmonary administration agents, and percutaneous administration agents. Examples of the injections include intravenous injection, intramuscular injection, intraperitoneal injection, and subcutaneous injection, through which the pharmaceutical composition can be administered systemically or locally.

Also, the administration method can be appropriately selected depending on the age, weight, sex, symptoms, etc. of a patient. The dose of a pharmaceutical composition containing the antibody or a polynucleotide encoding the antibody can be selected within a range of, for example, 0.0001 to 1000 mg/kg of body weight per dose. Alternatively, the dose can be selected within a range of, for example, 0.001 to 100000 mg/body of a patient, though the dose is not necessarily limited to these numeric values. Although the dose and the administration method vary depending on the weight, age, sex, symptoms, etc. of a patient, those skilled in the art can appropriately select the dose and the method.

The pharmaceutical composition including the antibody of the present invention or fragments thereof can be administered to a subject to treat and/or prevent cancer, preferably breast cancer, kidney cancer, pancreatic cancer, colorectal cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma.

The present invention further encompasses a method for treating and/or preventing cancer, comprising administering the pharmaceutical composition of the present invention in combination with the antitumor agent as exemplified above or a pharmaceutical composition comprising the antitumor agent to a subject. The antibody of the present invention or the fragment thereof may be administered simultaneously with or separately from the antitumor agent to the subject. In the case of separately administering these pharmaceutical compositions, either one may be administered first or later. Their dosing intervals, doses, administration routes, and the number of doses can be appropriately selected by a specialist. The other pharmaceutical dosage forms to be administered simultaneously also include, for example, pharmaceutical compositions formulated by mixing the antibody of the present invention or the fragment thereof or the antitumor agent into a pharmacologically acceptable carrier (or medium). The above descriptions about composition, formulation, administration routes, doses, cancer, etc. as to the pharmaceutical compositions and dosage forms containing the antibody of the present invention are also applicable to any of the above-mentioned pharmaceutical compositions and dosage forms containing the antitumor agent.

Thus, the present invention also provides a pharmaceutical combination for treatment and/or prevention of cancer, comprising the pharmaceutical composition of the present invention and a pharmaceutical composition comprising the antitumor agent as exemplified above, and a method for treating and/or preventing cancer, comprising administering thereof. The present invention also provides a pharmaceutical composition for treatment and/or prevention of cancer, comprising the antibody or the fragment thereof of the present invention and the antitumor agent together with a pharmacologically acceptable carrier.

<Polypeptide and DNA>

The present invention further provides a DNA encoding the antibody of the present invention or the fragment (antibody-binding fragment) thereof. The DNA may be a DNA encoding the heavy and/or light chains of the antibody or may be a DNA encoding the heavy and/or light chain variable regions of the antibody. The DNA may also be a DNA encoding each or a combination of the complementarity determining regions of antibody. Such a DNA includes, for example, a heavy chain variable region-encoding DNA comprising nucleotide sequences encoding the amino acid sequences of SEQ ID NOs: 6, 7, and 8, and a light chain variable region-encoding DNA comprising nucleotide sequences encoding the amino acid sequences of SEQ ID NOs: 10, 11, and 12, in the case of the above-mentioned antibody (a).

The complementarity determining regions (CDRs) encoded by the DNA having these sequences serve as regions that determine the specificity of the antibody. Sequences encoding the other regions (i.e., constant regions and framework regions) of the antibody may therefore be sequences derived from other antibodies. In this context, "other antibodies" also include antibodies derived from non-human organisms, but are preferably those derived from humans from the viewpoint of reducing adverse reactions. Specifically, in the DNA of the present invention, regions encoding each framework region and each constant region in the heavy and light chains preferably comprise nucleotide sequences encoding corresponding human antibody-derived amino acid sequences.

Further examples of the DNA encoding the antibody of the present invention include a DNA encoding a heavy chain variable region comprising a nucleotide sequence encoding the amino acid sequence of SEQ ID NO: 9, and a DNA encoding a light chain variable region comprising a nucleotide sequence encoding the amino acid sequence of SEQ ID NO: 13, in the case of the above-mentioned antibody (a). In this context, an example of nucleotide sequences encoding the amino acid sequence of SEQ ID NO: 9 is the nucleotide sequence of SEQ ID NO: 14. An example of nucleotide sequences encoding the amino acid sequence of SEQ ID NO: 13 is the nucleotide sequence of SEQ ID NO: 15. When such a DNA comprises regions encoding constant regions of the heavy and light chains, each of the regions preferably comprises a nucleotide sequence encoding a corresponding human antibody-derived amino acid sequence (amino acid sequence of each constant region of the heavy and light chains).

These antibody DNAs can be obtained, for example, by the methods described above, or the following method. First, total RNAs are prepared from hybridomas producing the antibody of the present invention using a commercially available RNA extraction kit, and cDNAs are synthesized therefrom using reverse transcriptase and random primers or the like. Subsequently, the antibody-encoding cDNAs are amplified by PCR using oligonucleotide primers for conserved sequences of variable regions in known mouse antibody heavy or light chain genes. Sequences encoding the constant regions can be obtained by PCR amplification of the known sequences. The nucleotide sequence of the DNA can be incorporated into a plasmid or a phage for sequencing, for example, and determined according to a conventional method.

The present invention further provides the following polypeptides and DNAs related to the above-mentioned antibodies (a) to (g):

(i) a polypeptide comprising any of amino acid sequences of SEQ ID NOs: 9, 19, 58, 63, 69, and 77, and a DNA encoding the polypeptide (e.g., a DNA comprising any of the nucleotide sequences of SEQ ID NOs: 14 and 24);

(ii) a polypeptide comprising any of amino acid sequences of SEQ ID NOs: 13, 23, 53, 62, 65, 73, and 81, and a DNA encoding the polypeptide (e.g., a DNA comprising any of the nucleotide sequences of SEQ ID NOs: 15, 25, and 54);

(iii) heavy chain CDR polypeptides selected from the group consisting of amino acid sequences shown by SEQ ID NOs: 6, 7, and 8, SEQ ID NOs: 16, 17, and 18, SEQ ID NOs: 55, 56, and 57, SEQ ID NOs: 66, 67, and 68, and SEQ ID NOs: 74, 75, and 76, and a DNA encoding the polypeptides; and (iv) light chain CDR polypeptides selected from amino acid sequences shown by SEQ ID NOs: 10, 11, and 12, SEQ ID NOs: 20, 21, and 22, SEQ ID NOs: 50, 51, and 52, SEQ ID NOs: 59, 60, and 61, SEQ ID NOs: 59, 64, and 61, SEQ ID NOs: 70, 71, and 72, and SEQ ID NOs: 78, 79, and 80, and a DNA encoding the polypeptides.

These polypeptides and DNAs can be prepared using genetic engineering techniques as described above.

SUMMARY OF THE PRESENT INVENTION

The aspects of the present invention described above are summarized below.

(1) An antibody or a fragment thereof which has immunological reactivity with a partial CAPRIN-1 polypeptide consisting of the amino acid sequence shown by SEQ ID NO: 5 or an amino acid sequence having 80% or higher sequence identity to the amino acid sequence.

(2) The antibody or the fragment thereof according to (1), wherein the antibody or the fragment thereof has cytotoxic activity against a cancer cell expressing a CAPRIN-1 protein.

(3) The antibody or the fragment thereof according to (1) or (2), wherein the antibody is a monoclonal antibody or a polyclonal antibody.

(4) The antibody or the fragment thereof according to any of (1) to (3), wherein the antibody is a human antibody, a humanized antibody, a chimeric antibody, a single-chain antibody, or a multispecific antibody.

(5) The antibody or the fragment thereof according to any of (1) to (4), which comprises a heavy chain variable region comprising complementarity determining regions of SEQ ID NOs: 6, 7, and 8 and a light chain variable region comprising complementarity determining regions of SEQ ID NOs: 10, 11, and 12 and has immunological reactivity with the CAPRIN-1 protein.

(6) The antibody or the fragment thereof according to any of (1) to (4), which comprises a heavy chain variable region comprising complementarity determining regions of SEQ ID NOs: 16, 17, and 18 and a light chain variable region comprising complementarity determining regions of SEQ ID NOs: 20, 21, and 22 and has immunological reactivity with the CAPRIN-1 protein.

(7) The antibody or the fragment thereof according to any of (1) to (4), which comprises a heavy chain variable region comprising complementarity determining regions of SEQ ID NOs: 6, 7, and 8 and a light chain variable region comprising complementarity determining regions of SEQ ID NOs: 50, 51, and 52 and has immunological reactivity with the CAPRIN-1 protein.

(8) The antibody or the fragment thereof according to any of (1) to (4), which comprises a heavy chain variable region comprising complementarity determining regions of SEQ ID NOs: 55, 56, and 57 and a light chain variable region comprising complementarity determining regions of SEQ ID NOs: 59, 60, and 61 and has immunological reactivity with the CAPRIN-1 protein.

(9) The antibody or the fragment thereof according to any of (1) to (4), which comprises a heavy chain variable region comprising complementarity determining regions of SEQ ID NOs: 55, 56, and 57 and a light chain variable region comprising complementarity determining regions of SEQ ID NOs: 59, 64, and 61 and has immunological reactivity with the CAPRIN-1 protein.

(10) The antibody or the fragment thereof according to any of (1) to (4), which comprises a heavy chain variable region comprising complementarity determining regions of SEQ ID NOs: 66, 67, and 68 and a light chain variable region comprising complementarity determining regions of SEQ ID NOs: 70, 71, and 72 and has immunological reactivity with the CAPRIN-1 protein.

(11) The antibody or the fragment thereof according to any of (1) to (4), which comprises a heavy chain variable region comprising complementarity determining regions of SEQ ID NOs: 74, 75, and 76 and a light chain variable region comprising complementarity determining regions of SEQ ID NOs: 78, 79, and 80 and has immunological reactivity with the CAPRIN-1 protein.

(12) The antibody or the fragment thereof according to any of (1) to (11), wherein the antibody or the fragment thereof is conjugated with an antitumor agent.

(13) A pharmaceutical composition for treatment and/or prevention of cancer, comprising the antibody or the fragment thereof according to any of (1) to (12) as an active ingredient.

(14) The pharmaceutical composition according to (13), wherein the cancer is breast cancer, kidney cancer, pancreatic cancer, colorectal cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma.

(15) A pharmaceutical combination for treatment and/or prevention of cancer, comprising the pharmaceutical composition according to (13) or (14) and a pharmaceutical composition comprising an antitumor agent.

(16) A DNA encoding the antibody or the fragment thereof according to any of (1) to (11).

(17) A method for treating and/or preventing cancer, comprising administering the antibody or the fragment thereof according to any of (1) to (12), the pharmaceutical composition according to (13) or (14), or the pharmaceutical combination according to (15), to a subject.

EXAMPLES

Hereinafter, the present invention will be described specifically with reference to Examples. However, the scope of the present invention is not intended to be limited by these specific examples.

Example 1

Analysis of CAPRIN-1 Expression in Each Tissue

CAPRIN-1 gene expression in canine and human normal tissues and various cell lines was examined by RT-PCR according to Example 1(4) of WO2010/016526. As a result, strong expression was observed in the testis among the healthy canine tissues, whereas expression was observed in canine breast cancer and adenocarcinoma tissues. Further, as a result of examining the expression in human tissues, the expression was observed only in the testis among normal tissues, as with the canine CAPRIN-1 gene. By contrast, the expression was detected in many types of cancer cell lines, including 8 human breast cancer cell lines (ZR75-1, MCF7, T47D, SK-BR-3, MDA-MB-157, BT-20, MDA-MB-231V, and MRK-nu-1) and 4 pancreatic cancer cell lines (Capan-2, MIAPaCa-2, Panc-1, and BxPc-3), among cancer cells. These results demonstrated that CAPRIN-1 expression is not found in normal tissues other than the testis, whereas CAPRIN-1 is expressed in the breast cancer cell lines and the pancreatic cancer cell lines.

Example 2

Preparation of Mouse Monoclonal Antibody Against CAPRIN-1

(1) Preparation of Mouse Monoclonal Antibody #1

100 µg of human CAPRIN-1 proteins (having the amino acid sequence of SEQ ID NO: 2) prepared in Example 3 of WO2010/016526 was mixed with an equal amount of MPL+TDM adjuvant (Sigma-Aldrich Corp.). This mixture was used as an antigen solution per mouse. The antigen solution was intraperitoneally administered to each 6-week-old Balb/c mouse (prepared by Japan SLC, Inc.). Then, 7 administrations were performed every 1 week to complete immunization. Three days after the final immunization, the spleen of each mouse was excised and ground between two sterilized glass slides. Procedures of washing with PBS(−) (manufactured by Nissui Pharmaceutical Co., Ltd.) and centrifuging at 1500 rpm for 10 minutes to remove the supernatant were repeated three times to obtain spleen cells. The obtained spleen cells were mixed with mouse myeloma cells SP2/0 (purchased from ATCC) at a ratio of 10:1. A PEG solution prepared by mixing 200 µl of an RPMI1640 medium containing 10% FBS, which was heated to 37° C., with 800 µl of PEG1500 (manufactured by Boehringer Ingelheim GmbH) was added to the cell mixture, and then it was left to stand for 5 minutes for cell fusion. After removal of the supernatant via centrifugation at 1700 rpm for 5 minutes, the cells were suspended in 150 ml of an RPMI1640 medium containing 15% FBS supplemented with 2% equivalent of a HAT solution (Gibco) (HAT selective medium). This suspension was seeded onto fifteen 96-well plates (Nunc) at 100 µl/well. The spleen cells and the myeloma cells were fused by culturing for 7 days at 37° C., 5% $CO_2$ to obtain hybridomas.

The prepared hybridomas were screened for the binding affinity of antibodies produced by the hybridomas against CAPRIN-1 proteins as an indicator. A 1 µg/ml solution of the CAPRIN-1 protein prepared in Example 3 of WO2010/016526 was added to a 96-well plate at 100 µl/well and left to stand at 4° C. for 18 hours. Each well was washed three times with PBS-T. Then, a 0.5% bovine serum albumin (BSA) solution (manufactured by Sigma-Aldrich Corp.) was added thereto at 400 µl/well and left to stand at room temperature for 3 hours. The solution in each well was removed, and each well was washed three times with 400 µl of PBS-T. Then, the culture supernatant of each hybridoma obtained above was added thereto at 100 µl/well and left to stand at room temperature for 2 hours. Each well was washed three times with PBS-T. Then, HRP-labeled anti-mouse IgG (H+L) antibodies (manufactured by Invitrogen Corp.) diluted 5000-fold with PBS were added thereto at 100 Owen and left to stand at room temperature for 1 hour. Each well was washed three times with PBS-T. Then, a TMB substrate solution (manufactured by Thermo Fisher Scientific Inc.) was added thereto at 100 µl/well and left to stand for 15 to 30 minutes to cause color reaction. After the color development, the reaction was terminated by the addition of 1N sulfuric acid at 100 µl/well. The absorbance was measured at 450 nm and 595 nm using an absorption spectrometer. As a result, several hybridomas producing antibodies having high absorbance were selected.

The selected hybridomas were added to a 96-well plate at 0.5 cells/well and cultured in the plate. One week later, hybridomas forming single colonies in the wells were observed. The cells in these wells were further cultured, and the cloned hybridomas were screened for the binding affinity of antibodies produced by the hybridomas to the CAPRIN-1 protein as an indicator. A 1 µg/ml solution of the CAPRIN-1 protein prepared in Example 3 of WO2010/016526 was added to a 96-well plate at 100 µl/well and left to stand at 4° C. for 18 hours. Each well was washed three times with PBS-T. Then, a 0.5% BSA solution was added thereto at 400 µl/well and left to stand at room temperature for 3 hours. The solution in each well was removed, and each well was washed three times with 400 µl of PBS-T. Then, the culture supernatant of each hybridoma obtained above was added thereto at 100 µl/well and left to stand at room temperature for 2 hours. Each well was washed three times with PBS-T. Then, HRP-labeled anti-mouse IgG (H+L) antibodies (manufactured by Invitrogen Corp.) diluted 5000-fold with PBS were added thereto at 100 µl/well and left to stand at room temperature for 1 hour. Each well was washed three times with PBS-T. Then, a TMB substrate solution (manufactured by Thermo Fisher Scientific Inc.) was added thereto at 100 µl/well and left to stand for 15 to 30 minutes to cause color reaction. After the color development, the reaction was terminated by the addition of 1N sulfuric acid at 100 µl/well. The absorbance was measured at 450 nm and 595 nm using an absorption spectrometer. As a result, 88 hybridoma lines producing monoclonal antibodies reactive with the CAPRIN-1 protein were obtained.

Next, these monoclonal antibodies were screened for antibodies reactive with the surface of breast cancer cells expressing CAPRIN-1. Specifically, $10^6$ cells of a human breast cancer cell line MDA-MB-231V were centrifuged in a 1.5-ml microcentrifuge tube. 100 µl of the culture supernatant of the hybridoma obtained above was added thereto and left to stand for 1 hour on ice. After washing with PBS, FITC-labeled goat anti-mouse IgG antibodies (manufactured by Invitrogen Corp.) diluted 500-fold with PBS containing 0.1% FBS were added thereto and left to stand for 1 hour on ice. After washing with PBS, the fluorescence intensity was measured using FACSCalibur (Becton, Dickinson and Company). On the other hand, the same operation as above was performed using the serum of each untreated 6-week-old Balb/c mouse diluted 500-fold with a medium for hybridoma culture, instead of the antibodies, to prepare a control. As a result, one monoclonal antibody (#1) having stronger fluorescence intensity than that of the control, i.e., reactive with the surface of the breast cancer cells, was selected.

(2) Identification of CAPRIN-1 Epitope Recognized by Anti-CAPRIN-1 Monoclonal Antibody #1

The cancer cell surface-reactive anti-CAPRIN-1 monoclonal antibody #1 obtained in the section (1) was used to identify a CAPRIN-1 epitope region recognized thereby. 100 µg of recombinant CAPRIN-1 proteins was dissolved in a protein inhibitor-free dissolution buffer and reacted with the mouse monoclonal antibody #1. A digestive enzyme trypsin or chymotrypsin was added to the solution to perform digestion reaction at an adequate temperature. After the reaction, a protein G Sepharose carrier was added to the reaction mixture, reacted therewith, and precipitated by centrifugation. After removal of the supernatant, the carrier was washed with a dissolution buffer and PBS and dissolved in 0.1% formic acid, and the supernatant was recovered. The recovered supernatant sample was applied to a reverse-phase column (HLB Extraction Cartridge (Oasis)) for antibody removal to obtain a sample solution. The obtained sample was subjected to reverse-phase liquid chromatography (Chromatography Nanosystem (KYA Tech Corp.)) to recover a solution containing only peptides, which was then introduced to a tandem mass spectrometer quadrupole-TOF mass spectrometer (Waters-MicroMass) for MS/MS analysis to detect the peptides contained in the sample. As a result, a polypeptide consisting of the amino acid sequence of SEQ ID NO: 5 was identified as a partial CAPRIN-1 sequence recognized by the anti-CAPRIN-1 monoclonal antibody #1.

(3) Preparation of Mouse Monoclonal Antibodies #2 and #3

In a similar way to that described in the section (1), a fusion protein of the amino acid sequence of SEQ ID NO: 5 identified in the section (2) and a carrier protein KLH (keyhole limpet haemocyanin) was mixed as an immunogen with an equal amount of an adjuvant TiterMax Gold® (CytRx Corp.), and this mixture was subcutaneously administered at a dose of 20 µg/shot to each mouse at 7-day intervals. After administration with four shots in total, spleen cells were obtained from the mouse 3 days after the final immunization and fused with mouse myeloma cells in the same way as in the section (1) to produce hybridomas. Then, antibodies were screened for, as an indicator, the reactivity of the antibodies contained in the culture supernatants of the produced hybridomas with a 1 µg/ml solution of CAPRIN-1 proteins prepared in Example 3 of WO2010/016526 or a fusion protein (used as an immunogen) of the amino acid sequence of SEQ ID NO: 5 and a carrier protein KLH. The 1 µg/ml solution of CAPRIN-1 proteins prepared in Example 3 of WO2010/016526 and the fusion protein (30 µg/ml) of the amino acid sequence of SEQ ID NO: 5 and a carrier protein KLH were each added at 100 µl/well to 96-well plates and left to stand at 4° C. for 18 hours. Each well was washed with PBS-T. Then, a Blockace (DS Pharma Biomedical Co., Ltd.) solution was added thereto at 400 µl/well and left to stand at room temperature for 3 hours. The solution in each well was removed, and each well was washed with PBS-T. Then, the culture supernatant of each hybridoma obtained above was added thereto at 100 µl/well and left to stand at room temperature for 2 hours. Each well was washed with PBS-T. Then, HRP-labeled anti-mouse IgG (H+L) antibodies (manufactured by Invitrogen Corp.) diluted 5000-fold with PBS were added thereto at 100 µl/well and left to stand at room temperature for 1 hour. Each well was washed with PBS-T. Then, a TMB substrate solution (manufactured by Thermo Fisher Scientific Inc.) was added thereto at 100 µl/well and left to stand for 5 to 30 minutes to cause color reaction. After the color development, the reaction was terminated by the addition of 1N sulfuric acid at 100 µl/well. The absorbance was measured at 450 nm and 595 nm using an absorption spectrometer. As a result, hybridomas producing antibodies having high absorbance were selected.

The selected hybridomas were added to a 96-well plate at 0.3 cells/well and cultured in the plate. One week later, hybridomas forming single colonies in the wells were observed. The cells in these wells were further cultured, and the cloned hybridomas were screened in the same way as above for the binding affinity of antibodies produced by the hybridomas to the amino acid sequence of SEQ ID NO: 5 as a partial CAPRIN-1 sequence as an indicator to obtain hybridomas producing antibodies against the amino acid of SEQ ID NO: 5.

Monoclonal antibodies produced by the obtained hybridomas were screened for antibodies reactive with the surface of breast cancer cells expressing CAPRIN-1. Specifically, $10^6$ cells of a human breast cancer cell line MDA-MB-231V were centrifuged in a 1.5-ml microcentrifuge tube. 100 µl of the culture supernatant of the hybridoma obtained above was added thereto and left to stand for 1 hour on ice. After washing with PBS, FITC-labeled goat anti-mouse IgG antibodies (manufactured by Invitrogen Corp.) diluted 500-fold with PBS containing 0.1% FBS were added thereto and left to stand for 1 hour on ice. After washing with PBS, the fluorescence intensity was measured using FACSCalibur (Becton, Dickinson and Company). On the other hand, the same operation as above was performed to prepare a sample using the serum of each untreated 6-week-old Balb/c mouse diluted 500-fold with a medium for hybridoma culture or prepare a negative control sample by the reaction only with secondary antibodies, instead of the antibodies. As a result, 2 monoclonal antibodies (#2 and #3) having stronger fluorescence intensity than that of the negative control, i.e., reactive with the surface of the breast cancer cells, were obtained.

The obtained mouse monoclonal antibodies #2 and #3 were examined for their specific reaction with the amino acid sequence of SEQ ID NO: 5 as a partial CAPRIN-1 sequence used as an immunogen. A 30 µg/ml solution of the amino acid sequence of SEQ ID NO: 5 prepared with a 0.1 M aqueous sodium carbonate solution and a partial CAPRIN-1 sequence free from the amino acid sequence of SEQ ID NO: 5 were each added to a 96-well plate Immobilizer Amino for ELISA (Nunc) at 100 µg/ml and reacted for one whole day and night at 4° C. to bind the peptides to the wells. A 0.1 M aqueous sodium carbonate solution containing 10 mM ethanolamine was added to the peptide-bound wells and left to stand at room temperature for 1 hour. The solution in each well was removed, and each well was then washed with PBS-T. Then, a Blockace solution was added thereto at 400 µl/well and left to stand at room temperature for 3 hours. The solution in each well was removed, and each well was washed with PBS-T. Then, the culture supernatant containing the mouse monoclonal antibody #2 was added thereto at 50 Owen and reacted at room temperature for 1 hour. Then, each well was washed with PBS-T, and HRP-labeled anti-mouse IgG (H+L) antibodies (manufactured by Invitrogen) diluted 5000-fold with a Blockace solution were added thereto at 50 µl/well and left to stand at room temperature for 1 hour. Each well was fully washed with PBS-T. Then, a TMB substrate solution (manufactured by Thermo Fisher Scientific Inc.) was added thereto at 100 µl/well and left to stand for 5 to 30 minutes to cause color reaction. After the color development, the reaction was terminated by the addition of 1N sulfuric acid at 100 µl/well. The absorbance was measured at 450 nm and 595 nm using an absorption spectrometer. As a result, the mouse monoclonal antibodies #2 and #3 did not react with the partial CAPRIN-1 sequence free from the amino acid sequence of SEQ ID NO: 5, but specifically reacted only with the amino acid sequence of SEQ ID NO: 5. The results demonstrated that the polypeptide of SEQ ID NO: 5 contains an epitope region for the anti-CAPRIN-1 antibodies #2 and #3.

Example 3

Preparation of Chicken Monoclonal Antibody Against CAPRIN-1

Chicken-derived monoclonal antibodies were prepared using as an immunogen a fusion protein of the amino acid sequence of SEQ ID NO: 5 identified in Example 2(2) and a carrier protein KLH (keyhole limpet haemocyanin). 300 µg of the immunogen was mixed with an equal amount of a complete Freund's adjuvant. This mixture was used as an antigen solution per chicken. The antigen solution was intraperitoneally administered to each 7-week-old chicken. Then, 7 administrations were performed every 4 weeks to complete immunization. Four days after the final immunization, the spleen of each chicken was excised and ground between two sterilized glass slides. Procedures of washing with PBS(−) (manufactured by Nissui Pharmaceutical Co., Ltd.) and centrifuging at 1500 rpm for 10 minutes to remove the supernatant were repeated three times to obtain spleen cells. The obtained spleen cells were mixed with light chain-deficient chicken myeloma cells established from chickens by transformation using avian reticuloendotheliosis virus, at a ratio of 5:1. A PEG solution prepared by mixing 200 µl of an IMDM medium containing 10% FBS, which was heated to 37° C., with 800 µl of PEG1500 (manufactured by Boehringer Ingelheim GmbH) was added to the cell mixture, and then it was left to stand for 5 minutes for cell fusion. After removal of the supernatant via centrifugation at 1700 rpm for 5 minutes, the cells were suspended in 300 ml of an IMDM medium containing 10% FBS supplemented with 2% equivalent of a HAT solution (Gibco) (HAT selective medium). This suspension was seeded onto thirty 96-well plates (Nunc) at 100 µl/well. The spleen cells and the chicken myeloma cells were fused by culturing for 7 days at 37° C., 5% $CO_2$ to obtain hybridomas.

Then, the antibodies were screened for, as an indicator, the reactivity of the antibody contained in the culture supernatants of the prepared hybridomas with a solution of CAPRIN-1 proteins prepared as described in Example 3 of WO2010/016526 or a fusion protein (used as an immunogen) of the amino acid sequence of SEQ ID NO: 5 and a carrier protein BSA. Specifically, the 1 µg/ml solution of CAPRIN-1 proteins prepared in Example 3 of WO2010/016526 and the fusion protein (1 µg/ml) of the amino acid sequence of SEQ ID NO: 5 and the carrier protein BSA were each added at 50 µl/well to 96-well plates and left to stand at 4° C. for 18 hours. Each well was washed with PBS-T. Then, a Blockace (DS Pharma Biomedical Co., Ltd.) solution was added thereto at 300 µl/well and left to stand at room temperature for 3 hours. The solution in each well was removed, and each well was washed with PBS-T. Then, the culture supernatant of each hybridoma obtained above was added thereto at 50 µl/well and left to stand at room temperature for 1 hour. Each well was washed with PBS-T. Then, HRP-labeled anti-chicken IgY antibodies (manufactured by KPL, Kirkegaard & Perry Laboratories, Inc.) diluted 1000-fold with PBS were added thereto at 100 µl/well and left to stand at room temperature for 1 hour. Each well was washed three times with PBS-T. Then, an OPD substrate solution was added thereto at 50 µl/well and left to stand for 5 to 15 minutes to cause color reaction. After the color development, the reaction was terminated by the addition of 2N sulfuric acid at 50 µl/well. The absorbance was measured at 490 nm and 630 nm using an absorption spectrometer. As a result, several hybridomas producing antibodies having high absorbance were selected.

The selected hybridomas were added to a 96-well plate at 0.5 cells/well and cultured in the plate. One week later, hybridomas forming single colonies in the wells were observed. The cells in these wells were further cultured, and the cloned hybridomas were screened for, as an indicator, the binding affinity of antibodies produced by the hybridomas to the CAPRIN-1 proteins or the reactivity of the antibodies against the fusion protein (used as an immunogen) of the amino acid sequence of SEQ ID NO: 5 and the carrier protein BSA, to obtain chicken monoclonal antibodies.

Next, these monoclonal antibodies were screened for antibodies reactive with the surface of breast cancer cells expressing CAPRIN-1. Specifically, $2 \times 10^5$ cells of a human breast cancer cell line MDA-MB-231V were centrifuged in a 1.5-ml microcentrifuge tube. 50 µl of the culture supernatant of each hybridoma obtained above was added thereto and left to stand for 1 hour on ice. After washing with PBS, FITC-labeled goat anti-chicken IgG (H+L) antibodies (manufactured by SouthernBiotech) diluted 100-fold with PBS containing 0.5% FBS were added thereto and left to stand for 1 hour on ice. After washing with PBS, the fluorescence intensity was measured using FACSCalibur (Becton, Dickinson and Company). On the other hand, the same operation as above was performed using a medium for hybridoma culture to prepare a negative control sample. As a result, 4 chicken monoclonal antibodies (chicken monoclonal antibodies #1, #2, #3, and #4) having stronger fluorescence intensity than that of the control, i.e., reactive with the surface of breast cancer cells expressing CAPRIN-1, were selected. These antibodies can bind to CAPRIN-1 expressed on the surface of breast cancer cells.

Example 4

Characterization of Selected Monoclonal Antibody (1) Characterization of Mouse Monoclonal Antibody
Amplification fragments of genes encoding the variable regions of the mouse monoclonal antibodies obtained in Example 2 were obtained according to a method described in Example 5 of WO2010/016526 and analyzed for their gene sequences and amino acid sequences encoded thereby. The resulting gene sequence encoding the heavy chain variable region of the mouse-derived monoclonal antibody #1 is shown in SEQ ID NO: 24, and the amino acid sequence is shown in SEQ ID NO: 19; and the gene sequence encoding the light chain variable region thereof is shown in SEQ ID NO: 25, and the amino acid sequence is shown in SEQ ID NO: 23. The resulting gene sequence encoding the heavy chain variable region of the mouse-derived monoclonal antibody #2 is shown in SEQ ID NO: 14, and the amino acid sequence is shown in SEQ ID NO: 9; and the gene sequence encoding the light chain variable region thereof is shown in SEQ ID NO: 15, and the amino acid sequence is shown in SEQ ID NO: 13. The resulting gene sequence encoding the heavy chain variable region of the mouse-derived monoclonal antibody #3 is shown in SEQ ID NO: 14, and the amino acid sequence is shown in SEQ ID NO: 9; and the gene sequence encoding the light chain variable region thereof is shown in SEQ ID NO: 54, and the amino acid sequence is shown in SEQ ID NO: 53.

In other words, the mouse monoclonal antibody #1 was found to comprise the heavy chain variable region of SEQ ID NO: 19 and the light chain variable region of SEQ ID NO: 23, wherein the heavy chain variable region had CDR1, CDR2, and CDR3 consisting of the amino acid sequences of SEQ ID NOs: 16, 17, and 18, respectively, and the light chain variable region had CDR1, CDR2, and CDR3 consisting of the amino acid sequences of SEQ ID NOs: 20, 21, and 22, respectively. The mouse monoclonal antibody #2 was found to comprise the heavy chain variable region of SEQ ID NO: 9 and the light chain variable region of SEQ ID NO: 13, wherein the heavy chain variable region had CDR1, CDR2, and CDR3 consisting of the amino acid sequences of SEQ ID NOs: 6, 7, and 8, respectively, and the light chain variable region had CDR1, CDR2, and CDR3 consisting of the amino acid sequences of SEQ ID NOs: 10, 11, and 12, respectively. The mouse monoclonal antibody #3 was found to comprise the heavy chain variable region of SEQ ID NO: 9 and the light chain variable region of SEQ ID NO: 53, wherein the heavy chain variable region had CDR1, CDR2, and CDR3 consisting of the amino acid sequences of SEQ ID NOs: 6, 7, and 8, respectively, and the light chain variable region had CDR1, CDR2, and CDR3 consisting of the amino acid sequences of SEQ ID NOs: 50, 51, and 52, respectively.

(2) Characterization of Chicken Monoclonal Antibody

Amplification fragments of genes encoding the variable regions of the chicken monoclonal antibodies (chicken monoclonal antibodies #1, #2, #3, and #4) obtained in Example 3 were obtained according to the method described in Example 4 of WO2011/096519 and analyzed for their gene sequences and amino acid sequences encoded thereby. The resulting amino acid sequence of the heavy chain variable region of the chicken monoclonal antibody #1 is shown in SEQ ID NO: 58, and the amino acid sequence of the light chain variable region thereof is shown in SEQ ID NO: 62. The amino acid sequence of the heavy chain variable region of the chicken monoclonal antibody #2 is shown in SEQ ID NO: 63, and the amino acid sequence of the light chain variable region thereof is shown in SEQ ID NO: 65. The amino acid sequence of the heavy chain variable region of the chicken monoclonal antibody #3 is shown in SEQ ID NO: 69, and the amino acid sequence of the light chain variable region thereof is shown in SEQ ID NO: 73. The amino acid sequence of the heavy chain variable region of the chicken monoclonal antibody #4 is shown in SEQ ID NO: 77, and the amino acid sequence of the light chain variable region thereof is shown in SEQ ID NO: 81.

In other words, the chicken monoclonal antibody #1 was found to comprise the heavy chain variable region of SEQ ID NO: 58 and the light chain variable region of SEQ ID NO: 62, wherein the heavy chain variable region had CDR1, CDR2, and CDR3 consisting of the amino acid sequences of SEQ ID NOs: 55, 56, and 57, respectively, and the light chain variable region had CDR1, CDR2, and CDR3 consisting of the amino acid sequences of SEQ ID NOs: 59, 60, and 61, respectively. The chicken monoclonal antibody #2 was found to comprise the heavy chain variable region of SEQ ID NO: 63 and the light chain variable region of SEQ ID NO: 65, wherein the heavy chain variable region had CDR1, CDR2, and CDR3 consisting of the amino acid sequences of SEQ ID NOs: 55, 56, and 57, respectively, and the light chain variable region had CDR1, CDR2, and CDR3 consisting of the amino acid sequences of SEQ ID NOs: 59, 64, and 61, respectively. The chicken monoclonal antibody #3 was found to comprise the heavy chain variable region of SEQ ID NO: 69 and the light chain variable region of SEQ ID NO: 73, wherein the heavy chain variable region had CDR1, CDR2, and CDR3 consisting of the amino acid sequences of SEQ ID NOs: 66, 67, and 68, respectively, and the light chain variable region had CDR1, CDR2, and CDR3 consisting of the amino acid sequences of SEQ ID NOs: 70, 71, and 72, respectively. The chicken monoclonal antibody #4 was found to comprise the heavy chain variable region of SEQ ID NO: 77 and the light chain variable region of SEQ ID NO: 81, wherein the heavy chain variable region had CDR1, CDR2, and CDR3 consisting of the amino acid sequences of SEQ ID NOs: 74, 75, and 76, respectively, and the light chain variable region had CDR1, CDR2, and CDR3 consisting of the amino acid sequences of SEQ ID NOs: 78, 79, and 80, respectively.

Example 5

Preparation of Polyclonal Antibody Against Partial CAPRIN-1 Polypeptide Present on Cancer Cell Surface For the purpose of obtaining polyclonal antibodies against partial CAPRIN-1 polypeptides present on cancer cell surface, a polypeptide (CAPRIN-1-derived peptide shown in SEQ ID NO: 5) comprising the epitope regions for the anti-CAPRIN-1 monoclonal antibodies #1, #2, and #3, a polypeptide having a region of amino acid residues 50 to 98 in the human CAPRIN-1 amino acid sequence of SEQ ID NO: 2, and a polypeptide having a region of amino acid residues 233 to 305 of SEQ ID NO: 2 were synthesized. 1 mg of these peptides were each mixed as an antigen with an equal volume of an incomplete Freund's adjuvant (IFA) solution. This mixture was subcutaneously administered to rabbit four times every two weeks. Then, blood was collected therefrom to obtain antiserum containing polyclonal antibody against each antigen. The antiserum was further purified using a protein G carrier (manufactured by GE Healthcare Bio-Sciences Ltd.), followed by replacement with PBS, to obtain polyclonal antibodies against partial CAPRIN-1 polypeptides present on cancer cell surface. In addition, the serum of a rabbit that received no antigen was prepared by purification using a protein G carrier in the same way as above and used as a control antibody.

Example 6

Analysis of CAPRIN-1 Protein Expression on Cancer Cell

Next, 8 human breast cancer cell lines (ZR75-1, MCF7, T47D, SK-BR-3, MDA-MB-157, BT-20, MDA-MB-231V, and MRK-nu-1) observed to have a high level of CAPRIN-1 gene expression were examined for their expression of CAPRIN-1 proteins on the cell surface. $5 \times 10^5$ cells of the human breast cancer cell lines that were observed above to have the gene expression were each centrifuged in a 1.5-ml microcentrifuge tube. After adding 2 µg (5 µl) of the polyclonal antibodies against CAPRIN-1-derived peptides prepared as described above in Example 5 thereto, the cells were further mixed with 95 µl of PBS containing 0.1% fetal bovine serum, and left to stand for 1 hour on ice. After washing with PBS, the resulting solution was mixed with 2 µl of Alexa 488-labeled goat anti-rabbit IgG antibodies (manufactured by Invitrogen Corp.) and 98 µl of PBS containing 0.1% fetal bovine serum (FBS) and left to stand for 30 hours on ice. After washing with PBS, the fluorescence intensity was measured using FACSCalibur (Becton, Dickinson and Company). On the other hand, the same operation as above was performed using the control antibodies prepared as described above in Example 5 instead of the polyclonal antibodies against CAPRIN-1-derived peptides to prepare a control. As a result, the cancer cells treated with the anti-CAPRIN-1 antibodies all exhibited fluorescence intensity at least 35% stronger than that of the control. This demonstrated that CAPRIN-1 proteins are expressed on the cell membrane surface of the human cancer cell lines. The rates of enhancement in the fluorescence intensity are expressed as the rates of increase in mean fluorescence intensity (MFI) in respective cell lines, which are calculated according to the following formula.

Rate of increase in mean fluorescence intensity(Rate of enhancement in fluorescence intensity)(%)= ((MFI of cells reacted with the anti-CAPRIN-1 antibodies)−(Control MFI))/(Control MFI)×100

Also, the fluorescence intensity was measured in 3 kidney cancer cell lines (Caki-1, Caki-2, and A498), a urinary bladder cancer cell line (T24), an ovary cancer cell line (SKOV3), a lung cancer cell line (QG56), a prostate cancer cell line (PC3), a uterine cervix cancer cell line (HeLa), a fibrosarcoma cell line (HT1080), 2 brain tumor cell lines (T98G and U87MG), a gastric cancer cell line (MNK28), a colorectal cancer cell line (Lovo), and pancreatic cancer cell lines (Capan-2, MIAPaCa-2, Panc-1, and BxPC-3) using the same approach as above. As a result, all the cancer cells had fluorescence intensity at least 35% stronger than that of the control.

As with the results obtained above, CAPRIN-1 expression was also confirmed using the anti-CAPRIN-1 monoclonal antibody (mouse monoclonal antibody #1) having the heavy chain variable region of SEQ ID NO: 19 and the light chain variable region of SEQ ID NO: 23, the anti-CAPRIN-1 monoclonal antibody (mouse monoclonal antibody #2) having the heavy chain variable region of SEQ ID NO: 9 and the light chain variable region of SEQ ID NO: 13, and the anti-CAPRIN-1 monoclonal antibody (mouse monoclonal antibody #3) having the heavy chain variable region of SEQ ID NO: 9 and the light chain variable region of SEQ ID NO: 53, which were obtained in Example 2, and the anti-CAPRIN-1 chicken monoclonal antibody #1 having the heavy chain variable region of SEQ ID NO: 58 and the light chain variable region of SEQ ID NO: 62, the anti-CAPRIN-1 chicken monoclonal antibody #2 having the heavy chain variable region of SEQ ID NO: 63 and the light chain variable region of SEQ ID NO: 65, the anti-CAPRIN-1 chicken monoclonal antibody #3 having the heavy chain variable region of SEQ ID NO: 69 and the light chain variable region of SEQ ID NO: 73, and the anti-CAPRIN-1 chicken monoclonal antibody #4 having the heavy chain variable region of SEQ ID NO: 77 and the light chain variable region of SEQ ID NO: 81 (chicken monoclonal antibodies #1 to #4), which were obtained in Example 3.

Example 7

Immunohistochemical Staining (1) CAPRIN-1 Expression in Mouse and Canine Normal Tissues A mouse (Balb/c, female) and a dog (beagle, female) were exsanguinated under ether anesthesia and under ketamine/isoflurane anesthesia and subjected to abdominal section. Then, each organ (stomach, liver, eyeball, thymus, muscle, bone marrow, uterus, small intestine, esophagus, heart, kidney, salivary gland, large intestine, mammary gland, brain, lung, skin, adrenal gland, ovary, pancreas, spleen, and urinary bladder) was transferred to a 10-cm dish containing PBS. Each organ was cut open in PBS and perfusion-fixed overnight in a 0.1 M phosphate buffer solution (pH 7.4) containing 4% paraformaldehyde (PFA). The perfusate was discarded, and the tissue surface of each organ was rinsed with PBS. Each tissue was placed in a PBS solution containing 10% sucrose in a 50-ml centrifuge tube and shaken at 4° C. for 2 hours using a rotor. The solution was replaced with a PBS solution containing 20% sucrose, and the resulting solution was left to stand at 4° C. until the tissue was precipitated. Then, the solution was replaced with a PBS solution containing 30% sucrose, and the resulting solution was left to stand at 4° C. until the tissue was precipitated. The tissue was taken out, and necessary portions were cut off with a surgical knife. Next, OCT compound (Tissue Tek) was poured onto the tissue surface and spread over the surface. Then, the tissue was mounted on Cryomold. The Cryomold was placed on dry ice to quickly freeze the tissue, and then the tissue was sliced into 10 to 20 µm thick using Cryostat (manufactured by Leica Biosystems), and dried in air, together with the glass slide, for 30 minutes using a hair dryer to prepare a glass slide with a tissue slice placed thereon. Next, the glass slide was placed in a staining bottle filled with PBS-T (physiological saline containing 0.05% Tween 20), and procedures of replacing PBS-T with a fresh one every 5 minutes were performed three times. Redundant water around each section was wiped off with Kimwipe. The section on the glass slide was encircled with a Dako pen (manufactured by Dako Japan Inc.). Then, MOM mouse Ig blocking reagent (Vectastain) for the mouse tissues and a PBS-T solution containing 10% FBS for the canine tissues were applied thereto as blocking solutions, and the glass slide was left to stand at room temperature for 1 hour in a moist chamber.

Next, a cancer cell surface-reactive polyclonal antibody against the CAPRIN-1-derived peptide (SEQ ID NO: 5) prepared in Example 5 was prepared into a 10 µg/ml solution with a blocking solution, and this solution was applied thereto. The glass slide was left to stand overnight at 4° C. in a moist chamber. After washing with PBS-T for 10 minutes three times, MOM biotin-labeled anti-IgG antibodies (Vectastain) diluted 250-fold with a blocking solution were applied thereto, and the glass slide was left to stand at room temperature for 1 hour in a moist chamber. After washing with PBS-T for 10 minutes three times, Avidin-Biotin ABC reagent (Vectastain) was applied thereto, and the glass slide was left to stand at room temperature for 5 minutes in a moist chamber. After washing with PBS-T for 10 minutes three times, a DAB staining solution (10 mg of DAB+10 µl of 30% $H_2O_2$/50 ml of 0.05 M tris-HCl (pH 7.6)) was applied thereto, and the glass slide was left to stand at room temperature for 30 minutes in a moist chamber. After rinsing with distilled water, a hematoxylin reagent (manufactured by Dako Japan Inc.) was applied thereto, and the glass slide was left to stand at room temperature for 1 minute and then rinsed with distilled water. The glass slide was placed in 70%, 80%, 90%, 95%, and 100% ethanol solutions in this order for 1 minute per solution and then left to stand overnight in xylene. The glass slide was taken out and mounted in Glycergel Mounting Medium (manufactured by Dako Japan Inc.), followed by observation. As a result, the intracellular expression of CAPRIN-1 was slightly observed in respective tissues of the salivary gland, kidney, colon, and stomach. Its expression, however, was not observed on the cell surface of these tissues. In addition, no expression was observed in tissues derived from the other organs.

(2) Expression of CAPRIN-1 in Canine Breast Cancer Tissue

Frozen breast cancer tissues of dogs pathologically diagnosed as malignant breast cancer were used in the preparation of frozen section slides and immunohistochemical staining using the polyclonal antibodies against the CAPRIN-1-derived peptide (SEQ ID NO: 5) prepared in Example 5, in the same way as above. As a result, the expression of CAPRIN-1 was observed in the canine breast cancer tissues.

(3) Expression of CAPRIN-1 in Various Human Cancer Tissues

Paraffin-embedded human various cancer tissue array samples (manufactured by US Biomax, Inc.) were used in immunohistochemical staining using the polyclonal antibodies (prepared in Example 5) against the CAPRIN-1-derived peptide (SEQ ID NO: 5) in the same way as above. As a result, the expression of CAPRIN-1 was observed in esophageal cancer, colon cancer, rectal cancer, lung cancer, pancreatic cancer, kidney cancer, urinary bladder cancer, and uterine cervix cancer.

Example 8

Preparation of Human-Mouse Chimeric Monoclonal Antibody

The gene amplification fragment prepared in Example 4 comprising the sequence (SEQ ID NO: 14) of the heavy chain variable region of the mouse monoclonal antibody #2 was treated at both ends with a restriction enzyme, then purified, and inserted according to a conventional method into a vector pcDNA4/myc-His (manufactured by Invitrogen Corp.) already having gene inserts of a mouse antibody-derived leader sequence and a human $IgG_1$ H chain constant region comprising the amino acid sequence of SEQ ID NO: 48. Also, the gene amplification fragment comprising the sequence (SEQ ID NO: 15) of the light chain variable region of the mouse monoclonal antibody #2 was treated at both ends with a restriction enzyme, then purified, and inserted according to a conventional method into a vector pcDNA3.1/myc-His (manufactured by Invitrogen Corp.) already having gene inserts of a mouse antibody-derived leader sequence and a human $IgG_1$ L chain constant region comprising the amino acid sequence of SEQ ID NO: 49.

Next, the recombinant vector having the insert of the nucleotide sequence encoding the heavy chain variable region (SEQ ID NO: 14) of the mouse monoclonal antibody #2 and the recombinant vector having the insert of the nucleotide sequence encoding the light chain variable region (SEQ ID NO: 15) of the mouse monoclonal antibody #2 were introduced into CHO-K1 cells (obtained from Riken Cell Bank). Specifically, $2 \times 10^5$ CHO-K1 cells were cultured in a Ham's F12 medium (manufactured by Invitrogen Corp.) containing 1 ml of 10% FBS per well in a 12-well culture plate, and washed with PBS(−). Then, a fresh Ham's F12 medium containing 1 ml of 10% FBS per well was added thereto. 250 ng each of the vectors in 30 µl of OptiMEM (manufactured by Invitrogen Corp.) was mixed with 30 µl of Polyfect transfection reagent (manufactured by Qiagen N.V.), and this mixture was added to each well. The CHO-K1 cells cotransfected with the recombinant vectors were cultured in a Ham's F12 medium containing 10% FBS supplemented with 200 µg/ml Zeocin (manufactured by Invitrogen Corp.) and 200 µg/ml Geneticin (manufactured by Roche Diagnostics K.K.) and then seeded in a 96-well plate at 0.5 cells/well to prepare a cell line stably producing a human-mouse chimeric monoclonal antibody #1 (#1) having the variable regions of the mouse monoclonal antibody #1. Cell lines stably producing a human-mouse chimeric monoclonal antibody #2 (#2) or a human-mouse chimeric monoclonal antibody #3 (#3) were also prepared in the same way as above as to the mouse monoclonal antibodies #2 and #3.

Each prepared cell line was cultured for 5 days in a 150-$cm^2$ flask at $5 \times 10^5$ cells/ml in 30 ml of a serum-free OptiCHO medium (manufactured by Invitrogen Corp.) to obtain culture supernatants containing #1, #2, or #3.

Also, cell lines stably producing human-mouse chimeric comparative antibodies 1 to 11 were prepared in the same way as above respectively, on the basis of the following anti-CAPRIN-1 mouse-derived monoclonal antibodies disclosed in WO2010/016526 as comparative antibodies: a comparative antibody 1 having the heavy chain variable region of SEQ ID NO: 26 and the light chain variable region of SEQ ID NO: 27; a comparative antibody 2 having the heavy chain variable region of SEQ ID NO: 28 and the light chain variable region of SEQ ID NO: 29; a comparative antibody 3 having the heavy chain variable region of SEQ ID NO: 30 and the light chain variable region of SEQ ID NO: 31; a comparative antibody 4 having the heavy chain variable region of SEQ ID NO: 32 and the light chain variable region of SEQ ID NO: 33; a comparative antibody 5 having the heavy chain variable region of SEQ ID NO: 34 and the light chain variable region of SEQ ID NO: 35; a comparative antibody 6 having the heavy chain variable region of SEQ ID NO: 36 and the light chain variable region of SEQ ID NO: 37; a comparative antibody 7 having the heavy chain variable region of SEQ ID NO: 38 and the light chain variable region of SEQ ID NO: 39; a comparative antibody 8 having the heavy chain variable region of SEQ ID NO: 40 and the light chain variable region of SEQ ID NO: 41; a comparative antibody 9 having the heavy chain variable region of SEQ ID NO: 42 and the light chain variable region of SEQ ID NO: 43; a comparative antibody 10 having the heavy chain variable region of SEQ ID NO: 44 and the light chain variable region of SEQ ID NO: 45; and a comparative antibody 11 having the heavy chain variable region of SEQ ID NO: 46 and the light chain variable region of SEQ ID NO: 47. Each prepared cell line was cultured for 5 days in a 150-$cm^2$ flask at $5 \times 10^5$ cells/ml in 30 ml of a serum-free OptiCHO medium (manufactured by Invitrogen Corp.) to obtain culture supernatants containing respective human-mouse chimeric comparative monoclonal antibodies 1 to 11.

Example 9

Preparation of Human-Chicken Chimeric Monoclonal Antibody

On the basis of the chicken monoclonal antibody #1 obtained in Example 3, a cell line stably producing a human-chicken chimeric antibody #1 having the variable regions of the chicken monoclonal antibody #1 was prepared according to the method described in Example 4(2) of WO2011/096519 on the basis of. The prepared cell line was cultured for 5 days in a 150-cm² flask at 5×10⁵ cells/ml in 30 ml of a serum-free OptiCHO medium (manufactured by Invitrogen Corp.) to obtain a culture supernatant containing human-chicken chimeric antibody #1.

Also, on the basis of the chicken monoclonal antibodies #2, #3, and #4, cell lines stably producing a human-chicken chimeric antibody #2, #3, or #4 were also prepared using the same approach as above. Each prepared cell line was used to obtain culture supernatants containing the human-chicken chimeric antibody #1, #2, #3, or #4.

Example 10

Expression Analysis of CAPRIN-1 on Surface of Various Cancer Cells Using Mouse Monoclonal Antibodies #1, #2, and #3 and Chicken Monoclonal Antibodies #1, #2, #3, and #4

Next, the human breast cancer cell lines (ZR75-1, MCF7, T47D, SK-BR-3, MDA-MB-157, BT-20, MDA-MB-231V, and MRK-nu-1), the kidney cancer cell lines (Caki-1, Caki-2, A498, and ACHN), the urinary bladder cancer cell line (T24), the ovary cancer cell line (SKOV3), the lung cancer cell lines (QG56 and A549), the pancreatic cancer cell lines (Capan-2 and MIAPaCa-2), the prostate cancer cell line (PC3), the uterine cervix cancer cell line (SW756), the fibrosarcoma cell line (HT1080), the brain tumor cell lines (T98G, U87MG, U251, SNB19, and U373), the gastric cancer cell lines (MNK28 and MNK45), the colorectal cancer cell lines (HT29, Lovo, CaCo2, SW480, and HCT116), the leukemia cell line (AML5), and the lymphoma cell line (Ramos) observed to have CAPRIN-1 gene expression were examined for their expression of CAPRIN-1 proteins on the cell surface using the culture supernatants respectively containing #1, #2, and #3 obtained in Example 2 and the chicken monoclonal antibodies #1, #2, #3, and #4 obtained in Example 3. 10⁶ cells of each cell line were centrifuged in each 1.5-ml microcentrifuge tube. Each culture supernatant (100 µl) containing any of the antibodies #1, #2, and #3 and the chicken monoclonal antibodies #1, #2, #3, and #4 was added to the tube and left to stand for 1 hour on ice. After washing with PBS, FITC-labeled goat anti-mouse IgG (H+L) antibodies (manufactured by Jackson ImmunoResearch Laboratories, Inc.) diluted with PBS containing 0.1% FBS for the mouse-derived antibodies or FITC-labeled goat anti-chicken IgG (H+L) antibodies (manufactured by SouthernBiotech) diluted 100-fold with PBS containing 0.1% FBS for the chicken-derived antibodies were added thereto and left to stand at 4° C. for 30 minutes. After washing with PBS, the fluorescence intensity was measured using FACSCalibur (Becton, Dickinson and Company). The negative control used was cells reacted only with secondary antibodies. As a result, all the cells each treated with any of the antibodies #1, #2, and #3 and the chicken monoclonal antibodies #1 to #4 had fluorescence intensity at least 35% stronger than that of the negative control. This demonstrated that CAPRIN-1 proteins are expressed on the cell membrane surface of the human cancer cell lines. The rates of enhancement in the fluorescence intensity was expressed as the rates of increase in mean fluorescence intensity (MFI) in respective cell lines, which are calculated according to the following formula.

Rate of increase in mean fluorescence intensity(Rate of enhancement in fluorescence intensity)(%)= ((MFI of cells reacted with the anti-CAPRIN-1 antibodies)−(Control MFI))/(Control MFI)×100

Example 11

Antitumor Activity Against Cancer Cells of Antibody Against CAPRIN-1-Derived Peptide (SEQ ID NO: 5)

In order to evaluate the antibodies against the CAPRIN-1-derived peptide (SEQ ID NO: 5) for the strength of its cytotoxicity against cancer cells expressing CAPRIN-1, ADCC activity was determined. The polyclonal antibodies (prepared in Example 5) against the peptide shown in SEQ ID NO: 5 were used in this evaluation. Similar evaluation was conducted using polyclonal antibodies against other human CAPRIN-1-derived peptides (polyclonal antibodies against amino acid residues 50 to 98 in the amino acid sequence of human CAPRIN-1 and polyclonal antibodies against amino acid residues 233 to 305 in the amino acid sequence of human CAPRIN-1, which were prepared in Example 5) as antibodies for comparison or the rabbit serum-derived control antibodies prepared in Example 5 as a negative control.

10⁶ cells of the human breast cancer cell line MCF7, the human colorectal cancer cell line HCT-116, the human pancreatic cancer cell line MIAPaCa-2, the human kidney cancer cell line Caki-2, and the human lung cancer cell line QG56 observed to have CAPRIN-1 expression were each collected into a 50-ml centrifuge tube, and 100 µCi of chromium 51 was then added thereto, followed by incubation at 37° C. for 2 hours. Then, the cells were washed three times with an RPMI1640 medium containing 10% fetal calf serum and added at 2×10³ cells/well to a 96-well V-bottom plate. The polyclonal antibodies against the human CAPRIN-1-derived peptide (SEQ ID NO: 5) and two types of polyclonal antibodies against other human CAPRIN-1-derived peptides (polyclonal antibodies against amino acid residues 50 to 98 of human CAPRIN-1 and polyclonal antibodies against amino acid residues 233 to 305 of human CAPRIN-1) were each added thereto at 1 µg/well. Lymphocytes separated from human peripheral blood according to a conventional method were further added thereto at 4×10⁵ cells/well and cultured for 4 hours at 37° C., 5% CO₂. After the culture, the amount of chromium (Cr) 51 released from damaged cancer cells was measured in the culture supernatant to calculate the ADCC activity against the cancer cells due to the polyclonal antibodies against the human CAPRIN-1-derived peptides. As a result, all the polyclonal antibodies obtained by immunization with the human partial CAPRIN-1 peptides having the amino acid sequence of amino acid residues 50 to 98 or amino acid residues 233-305 of human CAPRIN-1 had activity less than 10% against the human breast cancer cell line MCF7, the human colorectal cancer cell line HCT-116, the human pancreatic cancer cell line MIAPaCa-2, the human kidney cancer cell line Caki-2, and the human lung cancer cell line QG56. By contrast, the groups of the cells treated with the polyclonal antibodies against the human CAPRIN-1-derived peptide (SEQ ID NO: 5) exhibited 25% or higher cytotoxic activity against all the cancer cell lines. The negative control antibodies had activity less than 4% against all the cancer cells. These results revealed that antibodies against CAPRIN-1 shown in SEQ ID NO: 5 exerts strong cytotoxic activity against cancer cells expressing CAPRIN-1.

These results were obtained via determination of cytotoxic activity by, as described above, mixing the anti-CAPRIN-1 antibody used in the present invention, lymphocytes, and 2×10³ cells of each cancer cell line with incorporated chromium 51; culturing the cells for 4 hours; after the culture, measuring the amount of chromium 51 released into the medium; and calculating the cytotoxic activity against each cancer cell line according to the following formula*.

Cytotoxic activity(%)=[Amount of chromium 51 released from the target cells treated with the antibody against CAPRIN-1 and lymphocytes]/ [Amount of chromium 51 released from target cells treated with 1N hydrochloric acid]×100     *Expression The human-mouse chimeric monoclonal antibodies #1, #2, and #3 obtained in Example 8 and the human-chicken chimeric monoclonal antibodies #1, #2, #3, and #4 obtained in Example 9 were evaluated for their cytotoxic activity against human cancer cells. The culture supernatant of each cell line producing any of #1, #2, and #3 and the human-chicken chimeric monoclonal antibodies #1, #2, #3, and #4 was purified using Hitrap Protein A Sepharose FF (manufactured by GE Healthcare Bio-Sciences Ltd.). After replacement with PBS(−), the solution was filtered through a 0.22-μm filter (manufactured by Millipore Corp.). The resulting antibody was used for activity assay. $10^6$ cells each of the human breast cancer cell line MCF7, the human colorectal cancer cell line HCT-116, the human pancreatic cancer cell line MIAPaCa-2, the human kidney cancer cell line Caki-2, and the human lung cancer cell line QG56 were collected into a 50-ml centrifuge tube, and 100 μCi of chromium 51 was then added thereto, followed by incubation at 37° C. for 2 hours. Then, the cells were washed three times with an RPMI1640 medium containing 10% FBS and added at $2×10^3$ cells/well to a 96-well V-bottom plate to prepare target cells. The purified antibodies (human-mouse chimeric monoclonal antibodies #1, #2, and #3 and human-chicken chimeric monoclonal antibodies #1, #2, #3, and #4) and the human-mouse chimeric comparative monoclonal antibodies 1 to 11 obtained in Example 8 were each added thereto at 1.3 μg/well. A cell population containing human NK cells was separated using a conventional method from human peripheral blood lymphocytes prepared according to a conventional method. The cell population containing human NK cells that was used in this evaluation was prepared as follows: human peripheral blood mononuclear cells separated using a specific gravity separation solution Histopaque for peripheral blood mononuclear cell separation (Sigma-Aldrich Corp.) were reacted with FITC fluorescent dye-labeled antibodies (anti-human CD3 antibody, anti-human CD20 antibody, anti-human CD19 antibody, anti-human CD11c antibody, or anti-HLA-DR antibody (Becton, and Dickinson and Company)); and a cell population containing NK cells unstained with the antibodies was separated therefrom using a cell sorter (FACS Vantage SE (Becton, and Dickinson and Company)), or a cell population was separated with human NK cell separation kit (manufactured by Miltenyi Biotec K.K.). The separated cell population containing NK cells was added to the plate at $2×10^5$ cells/well and cultured for 4 hours at 37° C., 5% $CO_2$. After the culture, the amount of chromium 51 released from damaged tumor cells was measured in the culture supernatant to calculate the cytotoxic activity of each anti-CAPRIN-1 antibody against the cancer cells. The negative control used was cells treated with isotype control antibodies. As a result, the isotype control antibodies used and the human-mouse chimeric comparative monoclonal antibodies 1 to 11 had cytotoxic activity of less than 5% against MCF7, less than 3% against HCT-116, 7% against MIAPaCa-2, less than 8% against Caki-2, and less than 5% against QG56. By contrast, the human-mouse chimeric monoclonal antibody #1 and the human-chicken chimeric monoclonal antibodies #1 to #4 had cytotoxic activity of 30% or higher against MCF7, 19% or higher against HCT-116, 28% or higher against MIAPaCa-2, 34% or higher against Caki-2, and 10% or higher against QG56. Also, the human-mouse chimeric monoclonal antibodies #2 and #3 had cytotoxic activity of 32% or higher against MCF7, 18% or higher against HCT-116, 32% or higher against MIAPaCa-2, 18% or higher against Caki-2, and 10% or higher against QG56. Likewise, the isotype control antibodies used and the comparative antibodies 1 to 11 used had cytotoxic activity less than 4% against all other cancer cells: breast cancer cell lines ZR75-1, T47D, Hs578T, BT-20, SK-BR-3, MDA-MB-231V, and MRK-nu-1, glioma cell lines T98G and U373, a lung cancer cell line A549, kidney cancer cell lines Caki-1 and ACHN, a uterine cervix cancer cell line SW756, a urinary bladder cancer cell line T24, gastric cancer cell lines MKN28 and MKN45, a colorectal cancer cell line SW480, a leukemia cell line AML5, and a lymphoma cell line Ramos. By contrast, the human-mouse chimeric monoclonal antibodies #1, #2, and #3 and the human-chicken chimeric monoclonal antibodies #1, #2, #3, and #4 were observed to have 10% or higher cytotoxic activity against these cell lines. These results showed that the obtained monoclonal antibodies #1, #2, and #3 and human-chicken chimeric monoclonal antibodies #1, #2, #3, and #4 against CAPRIN-1 damage CAPRIN-1-expressing cancer cells through their ADCC activity, and it was demonstrated that the human-mouse chimeric monoclonal antibodies #1, #2, and #3 and the human-chicken chimeric monoclonal antibodies #1, #2, #3, and #4 exhibit stronger cytotoxic activity against human cancer cells than that of the comparative antibodies 1 to 11.

Also, the human-chicken chimeric monoclonal antibodies #1, #2, #3, and #4 were evaluated in the same way as above for their cytotoxic activity against the human breast cancer cell line MDA-MB-436, the human kidney cancer cell line Caki-1, the human lung cancer cell line A549, the human pancreatic cancer cell line Panc-1, and the human colorectal cancer cells DLD-1 observed to have CAPRIN-1 gene expression. Further, human-chicken chimeric antibodies #1 and #2 against CAPRIN-1 described in Example 4 of WO2011/096517 were used as comparative antibodies 12 and 13, respectively; a human-chicken chimeric antibody #1 against CAPRIN-1 described in Example 4 of WO2011/096519 was used as a comparative antibody 13; a human-chicken chimeric antibody #1 and mouse monoclonal antibodies #2, #3, #4, #5, and #6 against CAPRIN-1 described in Example 4 of WO2011/096528 were used as comparative antibodies 14, 15, 16, 17, 18, and 19 respectively; mouse monoclonal antibodies #1, #2, and #3 against CAPRIN-1 described in Example 3 of WO2011/096533 were used as comparative antibodies 20, 21, and 22, respectively; and mouse monoclonal antibodies #1, #2, and #3 against CAPRIN-1 described in Example 3 of WO2011/096534 were used as comparative antibodies 23, 24, and 25, respectively, for evaluation of the cytotoxic activity. Specifically, $10^6$ cells of the human colorectal cancer cell line DLD-1 were collected into a 50-ml centrifuge tube, and 100 μCi of chromium 51 was then added thereto, followed by incubation at 37° C. for 1 hour. Then, the cells were washed three times with an RPMI1640 medium containing 10% FBS and added at $2×10^3$ cells/well to a 96-well V-bottom plate to prepare target cells. Next, the human-chicken chimeric monoclonal antibodies #1 to #4 and the comparative antibodies 12 to 25 were each added thereto at 1 μg/well. A cell population containing human NK cells prepared according to a conventional method was further added thereto at $10^5$ cells/well and cultured for 4 hours at 37° C., 5% $CO_2$. After the culture, the amount of chromium 51 released from damaged tumor cells was measured in the culture supernatant to calculate the cytotoxic activity of each anti-CAPRIN-1 antibody against the cancer cells. Cytotoxicity against MDA-MB-436, Caki-1, A549, and Panc-1 was also evaluated in the same way as above. As a result, all the comparative antibodies 12 to 25 had 5% or lower cytotoxic activity against MDA-MB-436, whereas the human-chicken chimeric monoclonal antibodies #1, #2, #3, and #4 exhibited 18% or higher cytotoxic activity against this cell line. All the comparative antibodies 12 to 25 had 5% or lower cytotoxic activity against Caki-1, whereas the human-chicken chimeric monoclonal antibodies #1, #2, #3, and #4 exhibited 14% or higher cytotoxic activity against this cell line. All the comparative antibodies 12 to 25 had 5% or lower cytotoxic activity against A549, whereas the human-chicken chimeric monoclonal antibodies #1, #2, #3, and #4 exhibited 12% or higher cytotoxic activity against this cell line. All the comparative antibodies 12 to 25 had 5% or lower cytotoxic activity against Panc-1, whereas the human-chicken chimeric monoclonal antibodies #1, #2, #3 and #4 exhibited 18% or higher cytotoxic activity against this cell line. All the comparative antibodies 12 to 25 had 7% or lower cytotoxic activity against DLD-1, whereas the human-chicken chimeric monoclonal antibodies #1, #2, #3, and #4 exhibited 15% or higher cytotoxic activity against this cell line.

These results were obtained via determination of cytotoxic activity by, as described above, mixing the anti-CAPRIN-1 antibody used in the present invention, lymphocytes (cell population containing NK cells), and 2×10³ cells of each cancer cell line with incorporated chromium 51; culturing the cells for 4 hours; after the culture, measuring the amount of chromium 51 released into the medium; and calculating the cytotoxic activity against each cancer cell line according to the following formula*.

Cytotoxic activity(%)=[Amount of chromium 51 released from the target cells treated with the antibody against CAPRIN-1 and lymphocytes (cell population containing NK cells)]/[Amount of chromium 51 released from target cells treated with 1N hydrochloric acid]×100    *Expression

Example 12

The Number of CAPRIN-1 Molecules on Surface of Various Cancer Cells Recognized by Anti-CAPRIN-1 Monoclonal Antibodies #1, #2, and #3

Human breast cancer cell lines (ZR75-1, MCF7, T47D, SK-BR-3, MDA-MB-157, BT-20, MDA-MB-231V, and MRK-nu-1), kidney cancer cell lines (Caki-1, Caki-2, A498, and ACHN), a urinary bladder cancer cell line (T24), an ovary cancer cell line (SKOV3), lung cancer cell lines (QG56 and A549), pancreatic cancer cell lines (MIAPaCa-2 and Capan-2), a prostate cancer cell line (PC3), a uterine cervix cancer cell line (SW756), a fibrosarcoma cell line (HT1080), brain tumor cell lines (T98G, U87MG, U251, SNB19, and U373), gastric cancer cell lines (MNK28 and MNK45), colorectal cancer cell lines (HT29, Lovo, CaCo2, SW480, and HCT116), a leukemia cell line (AML5), and a lymphoma cell line (Ramos) were examined using an assay kit for the number of molecules "QIFIKIT" (manufactured by Dako Japan Inc.) for the number of CAPRIN-1 molecules on their cell surface recognized by the mouse monoclonal antibodies #1, #2, and #3 obtained in Example 2. Similarly, the number of CAPRIN-1 molecules on the surface of these various cancer cells was also examined using the comparative monoclonal antibodies 1 to 11.

Specifically, according to the protocol attached to the kit, each antibody (mouse monoclonal antibodies #1, #2, and #3 and comparative antibodies 1 to 11) was diluted into 5 µg/ml at final concentration with PBS, and this dilution was added to each cell line and reacted for 30 minutes. After washing with PBS, fluorescently labeled anti-mouse IgG antibodies attached to the kit were added as secondary antibodies, together with calibration beads attached to the kit, to each cell line and left to stand for 45 minutes on ice. Each cell line and the calibration beads were washed with PBS. Then, the fluorescence intensity was measured using FACSCalibur (Becton, Dickinson and Company) to obtain a mean fluorescence intensity value (mean) for all the antibodies described above. The negative control used was cells reacted with isotype control antibodies, and a mean was also obtained. Each mean fluorescence intensity value (mean) was used to calculate the number of molecules according to the protocol attached to the kit. As a result, the number of CAPRIN-1 molecules on the surface of various cancer cells recognized by the mouse monoclonal antibodies #1, #2, and #3 was $10^5$ or more per cell for all the examined human cancer cell lines. On the other hand, the number of molecules recognized by the comparative antibodies 1 to 11 was less than $10^5$ per cell.

INDUSTRIAL APPLICABILITY

The antibody of the present invention is useful in the treatment and/or prevention of cancer.

All publications, patents, and patent applications cited herein are incorporated herein by reference in their entirety.

The invention claimed is:

1. An antibody or a fragment thereof which has immunological reactivity with a partial CAPRIN-1 polypeptide consisting of the amino acid sequence shown by SEQ ID NO: 5.

2. The antibody or the fragment thereof according to claim 1, wherein the antibody or the fragment thereof has cytotoxic activity against a cancer cell expressing a CAPRIN-1 protein.

3. The antibody or the fragment thereof according to claim 1, wherein the antibody is a monoclonal antibody or a polyclonal antibody.

4. The antibody or the fragment thereof according to claim 1, wherein the antibody is a human antibody, a humanized antibody, a chimeric antibody, a single-chain antibody, or a multispecific antibody.

5. The antibody or the fragment thereof according to claim 1, which comprises a heavy chain variable region comprising complementarity determining regions of SEQ ID NOs: 6, 7, and 8 and a light chain variable region comprising complementarity determining regions of SEQ ID NOs: 10, 11, and 12 and has immunological reactivity with the CAPRIN-1 protein.

6. The antibody or the fragment thereof according to claim 1, which comprises a heavy chain variable region comprising complementarity determining regions of SEQ ID NOs: 16, 17, and 18 and a light chain variable region comprising complementarity determining regions of SEQ ID NOs: 20, 21, and 22 and has immunological reactivity with the CAPRIN-1 protein.

7. The antibody or the fragment thereof according to claim 1, which comprises a heavy chain variable region comprising complementarity determining regions of SEQ ID NOs: 6, 7, and 8 and a light chain variable region comprising complementarity determining regions of SEQ ID NOs: 50, 51, and 52 and has immunological reactivity with the CAPRIN-1 protein.

8. The antibody or the fragment thereof according to claim 1, which comprises a heavy chain variable region comprising complementarity determining regions of SEQ ID NOs: 55, 56, and 57 and a light chain variable region comprising complementarity determining regions of SEQ ID NOs: 59, 60, and 61 and has immunological reactivity with the CAPRIN-1 protein.

9. The antibody or the fragment thereof according to claim 1, which comprises a heavy chain variable region comprising complementarity determining regions of SEQ ID NOs: 55, 56, and 57 and a light chain variable region comprising complementarity determining regions of SEQ ID NOs: 59, 64, and 61 and has immunological reactivity with the CAPRIN-1 protein.

10. The antibody or the fragment thereof according to claim 1, which comprises a heavy chain variable region comprising complementarity determining regions of SEQ ID NOs: 66, 67, and 68 and a light chain variable region comprising complementarity determining regions of SEQ ID NOs: 70, 71, and 72 and has immunological reactivity with the CAPRIN-1 protein.

11. The antibody or the fragment thereof according to claim 1, which comprises a heavy chain variable region comprising complementarity determining regions of SEQ ID NOs: 74, 75, and 76 and a light chain variable region comprising complementarity determining regions of SEQ ID NOs: 78, 79, and 80 and has immunological reactivity with the CAPRIN-1 protein.

12. The antibody or the fragment thereof according to claim 1, wherein the antibody or the fragment thereof is conjugated with an antitumor agent.

13. A pharmaceutical composition for treatment of cancer, comprising the antibody or the fragment thereof according to claim 1 as an active ingredient, wherein the cancer is a CAPRIN-1 expressing cancer.

14. The pharmaceutical composition according to claim 13, wherein the cancer is breast cancer, kidney cancer, pancreatic cancer, colorectal cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma.

15. A pharmaceutical combination for treatment of cancer, comprising a pharmaceutical composition according to claim 13 and a pharmaceutical composition comprising an antitumor agent.

16. A DNA encoding the antibody or the fragment thereof according to claim 1.

17. A method for treating cancer, comprising administering the antibody or the fragment thereof according to claim 1, wherein the cancer is a CAPRIN-1 expressing cancer.

18. The antibody or the fragment thereof according to claim 2, wherein the antibody is a monoclonal antibody or a polyclonal antibody.

19. The antibody or the fragment thereof according to claim 2, wherein the antibody is a human antibody, a humanized antibody, a chimeric antibody, a single-chain antibody, or a multispecific antibody.

20. The antibody or the fragment thereof according to claim 3, wherein the antibody is a human antibody, a humanized antibody, a chimeric antibody, a single-chain antibody, or a multispecific antibody.

\* \* \* \* \*

SEQUENCE LISTING

```
<160> NUMBER OF SEQ ID NOS: 81

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)
<223> OTHER INFORMATION:

<400> SEQUENCE: 1
cagagggctg ctggctggct aagtccctcc cgctcccggc tctcgcctca ctaggagcgg     60
ctctcggtgc agcgggacag ggcgaagcgg cctgcgccca cggagcgcgc gacactgccc    120
ggaagggacc gccacccttg cccctcagc  tgcccactcg tgatttccag cggcctccgc    180
```

```
gcgcgcacg atg ccc tcg gcc acc agc cac agc ggg agc ggc agc aag tcg    231
          Met Pro Ser Ala Thr Ser His Ser Gly Ser Gly Ser Lys Ser
            1               5                  10 tcc gga ccg cca ccg ccg tcg ggt tcc tcc ggg agt gag gcg gcc gcg    279
Ser Gly Pro Pro Pro Pro Ser Gly Ser Ser Gly Ser Glu Ala Ala Ala
 15              20                  25                  30 gga gcc ggg gcc gcc gcg ccg gct tct cag cac ccc gca acc ggc acc    327
Gly Ala Gly Ala Ala Ala Pro Ala Ser Gln His Pro Ala Thr Gly Thr
                 35                  40                  45 ggc gct gtc cag acc gag gcc atg aag cag att ctc ggg gtg atc gac    375
Gly Ala Val Gln Thr Glu Ala Met Lys Gln Ile Leu Gly Val Ile Asp
             50                  55                  60 aag aaa ctt cgg aac ctg gag aag aaa aag ggt aag ctt gat gat tac    423
Lys Lys Leu Arg Asn Leu Glu Lys Lys Lys Gly Lys Leu Asp Asp Tyr
         65                  70                  75 cag gaa cga atg aac aaa ggg gaa agg ctt aat caa gat cag ctg gat    471
Gln Glu Arg Met Asn Lys Gly Glu Arg Leu Asn Gln Asp Gln Leu Asp
     80                  85                  90 gcc gtt tct aag tac cag gaa gtc aca aat aat ttg gag ttt gca aaa    519
Ala Val Ser Lys Tyr Gln Glu Val Thr Asn Asn Leu Glu Phe Ala Lys
 95                 100                 105                 110 gaa tta cag agg agt ttc atg gca cta agt caa gat att cag aaa aca    567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa    615
Ile Lys Lys Thr Ala Arg Arg Glu Gln Leu Met Arg Glu Glu Ala Glu
            130                 135                 140 cag aaa cgt tta aaa act gta ctt gag cta cag tat gtt ttg gac aaa    663
Gln Lys Arg Leu Lys Thr Val Leu Glu Leu Gln Tyr Val Leu Asp Lys
        145                 150                 155 ttg gga gat gat gaa gtg cgg act gac ctg aaa caa ggt ttg aat gga    711
Leu Gly Asp Asp Glu Val Arg Thr Asp Leu Lys Gln Gly Leu Asn Gly
    160                 165                 170 gtg cca ata ttg tcc gaa gag gag ttg tca ttg ttg gat gaa ttc tat    759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag    807
Lys Leu Val Asp Pro Glu Arg Asp Met Ser Leu Arg Leu Asn Glu Gln
                195                 200                 205 tat gaa cat gcc tcc att cac ctg tgg gac ctg ctg gaa ggg aag gaa    855
Tyr Glu His Ala Ser Ile His Leu Trp Asp Leu Leu Glu Gly Lys Glu
            210                 215                 220 aaa cct gta tgt gga acc acc tat aaa gtt cta aag gaa att gtt gag    903
Lys Pro Val Cys Gly Thr Thr Tyr Lys Val Leu Lys Glu Ile Val Glu
        225                 230                 235 cgt gtt ttt cag tca aac tac ttt gac agc acc cac aac cac cag aat    951
Arg Val Phe Gln Ser Asn Tyr Phe Asp Ser Thr His Asn His Gln Asn
    240                 245                 250 ggg ctg tgt gag gaa gaa gag gca gcc tca gca cct gca gtt gaa gac    999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa    1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa    1095
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt    1143
Thr Gln Phe Thr Ser Gly Glu Lys Glu Gln Val Asp Glu Trp Thr Val
        305                 310                 315
```

```
gaa acg gtt gag gtg gta aat tca ctc cag cag caa cct cag gct gca    1191
Glu Thr Val Glu Val Val Asn Ser Leu Gln Gln Gln Pro Gln Ala Ala
    320                 325                 330 tcc cct tca gta cca gag ccc cac tct ttg act cca gtg gct cag gca    1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg    1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat    1335
Gln Gly Pro Tyr Asn Phe Ile Gln Asp Ser Met Leu Asp Phe Glu Asn
        370                 375                 380 cag aca ctt gat cct gcc att gta tct gca cag cct atg aat cca aca    1383
Gln Thr Leu Asp Pro Ala Ile Val Ser Ala Gln Pro Met Asn Pro Thr
            385                 390                 395 caa aac atg gac atg ccc cag ctg gtt tgc cct cca gtt cat tct gaa    1431
Gln Asn Met Asp Met Pro Gln Leu Val Cys Pro Pro Val His Ser Glu
400                 405                 410 tct aga ctt gct cag cct aat caa gtt cct gta caa cca gaa gcg aca    1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa    1527
Gln Val Pro Leu Val Ser Ser Thr Ser Glu Gly Tyr Thr Ala Ser Gln
                435                 440                 445 ccc ttg tac cag cct tct cat gct aca gag caa cga cca cag aag gaa    1575
Pro Leu Tyr Gln Pro Ser His Ala Thr Glu Gln Arg Pro Gln Lys Glu
        450                 455                 460 cca att gat cag att cag gca aca atc tct tta aat aca gac cag act    1623
Pro Ile Asp Gln Ile Gln Ala Thr Ile Ser Leu Asn Thr Asp Gln Thr
            465                 470                 475 aca gca tca tca tcc ctt cct gct gcg tct cag cct caa gta ttt cag    1671
Thr Ala Ser Ser Ser Leu Pro Ala Ala Ser Gln Pro Gln Val Phe Gln
480                 485                 490 gct ggg aca agc aaa cct tta cat agc agt gga atc aat gta aat gca    1719
Ala Gly Thr Ser Lys Pro Leu His Ser Ser Gly Ile Asn Val Asn Ala
495                 500                 505                 510 gct cca ttc caa tcc atg caa acg gtg ttc aat atg aat gcc cca gtt    1767
Ala Pro Phe Gln Ser Met Gln Thr Val Phe Asn Met Asn Ala Pro Val
                515                 520                 525 cct cct gtt aat gaa cca gaa act tta aaa cag caa aat cag tac cag    1815
Pro Pro Val Asn Glu Pro Glu Thr Leu Lys Gln Gln Asn Gln Tyr Gln
        530                 535                 540 gcc agt tat aac cag agc ttt tct agt cag cct cac caa gta gaa caa    1863
Ala Ser Tyr Asn Gln Ser Phe Ser Ser Gln Pro His Gln Val Glu Gln
            545                 550                 555 aca gag ctt cag caa gaa cag ctt caa aca gtg gtt ggc act tac cat    1911
Thr Glu Leu Gln Gln Glu Gln Leu Gln Thr Val Val Gly Thr Tyr His
560                 565                 570 ggt tcc cca gac cag tcc cat caa gtg act ggt aac cac cag cag cct    1959
Gly Ser Pro Asp Gln Ser His Gln Val Thr Gly Asn His Gln Gln Pro
575                 580                 585                 590 cct cag cag aac act gga ttt cca cgt agc aat cag ccc tat tac aat    2007
Pro Gln Gln Asn Thr Gly Phe Pro Arg Ser Asn Gln Pro Tyr Tyr Asn
                595                 600                 605 agt cgt ggt gtg tct cgt gga ggc tcc cgt ggt gct aga ggc ttg atg    2055
Ser Arg Gly Val Ser Arg Gly Gly Ser Arg Gly Ala Arg Gly Leu Met
        610                 615                 620 aat gga tac cgg ggc cct gcc aat gga ttc aga gga gga tat gat ggt    2103
Asn Gly Tyr Arg Gly Pro Ala Asn Gly Phe Arg Gly Gly Tyr Asp Gly
```

```
                625                 630                 635
tac cgc cct tca ttc tct aac act cca aac agt ggt tat aca cag tct    2151
Tyr Arg Pro Ser Phe Ser Asn Thr Pro Asn Ser Gly Tyr Thr Gln Ser
        640                 645                 650 cag ttc agt gct ccc cgg gat tac tct ggc tat caa cgg gat gga tat    2199
Gln Phe Ser Ala Pro Arg Asp Tyr Ser Gly Tyr Gln Arg Asp Gly Tyr
655                 660                 665                 670 cag cag aat ttc aag cga ggc tct ggg cag agt gga cca cgg gga gcc    2247
Gln Gln Asn Phe Lys Arg Gly Ser Gly Gln Ser Gly Pro Arg Gly Ala
                675                 680                 685 cca cga ggt cgt gga ggg ccc cca aga ccc aac aga ggg atg ccg caa    2295
Pro Arg Gly Arg Gly Gly Pro Pro Arg Pro Asn Arg Gly Met Pro Gln
            690                 695                 700 atg aac act cag caa gtg aat taa tctgattcac aggattatgt ttaatcgcca   2349
Met Asn Thr Gln Gln Val Asn
            705 aaaacacact ggccagtgta ccataatatg ttaccagaag agttattatc tatttgttct   2409 cccttttcagg aaacttattg taaagggact gttttcatcc cataaagaca ggactacaat  2469 tgtcagcttt ctattacctg gatatggaag gaaactattt ttactctgca tgttctgtcc   2529 taagcgtcat cttgagcctt gcacatgata ctcagattcc tcacccttgc ttaggagtaa   2589 aacaatatac tttacagggt gataataatc tccatagtta tttgaagtgg cttgaaaaag   2649 gcaagattga cttttatgac attggataaa atctacaaat cagccctcga gttattcaat   2709 gataactgac aaactaaatt atttccctag aaaggaagat gaaaggagtg gagtgtggtt   2769 tggcagaaca actgcatttc acagcttttc cagttaaatt ggagcactga acgttcagat   2829 gcataccaaa ttatgcatgg gtcctaatca cacatataag gctggctacc agctttgaca   2889 cagcactgtt catctggcca aacaactgtg gttaaaaaca catgtaaaat gcttttttaac  2949 agctgatact gtataagaca aagccaagat gcaaaattag gctttgattg gcacttttttg  3009 aaaaatatgc aacaaatatg ggatgtaatc cggatggccg cttctgtact taatgtgaaa   3069 tatttagata cctttttgaa cacttaacag tttctttgag acaatgactt ttgtaaggat    3129 tggtactatc tatcattcct tatgacatgt acattgtctg tcactaatcc ttggattttg    3189 ctgtattgtc acctaaattg gtacaggtac tgatgaaaat ctctagtgga taatcataac    3249 actctcggtc acatgttttt ccttcagctt gaaagctttt ttttaaaagg aaagatacc     3309 aaatgcctgc tgctaccacc cttttcaatt gctatctttt gaaaggcacc agtatgtgtt    3369 ttagattgat ttccctgttt cagggaaatc acggacagta gtttcagttc tgatggtata    3429 agcaaaacaa ataaaacgtt tataaaagtt gtatcttgaa acactggtgt tcaacagcta    3489 gcagcttatg tgattcaccc catgccacgt tagtgtcaca aattttatgg tttatctcca    3549 gcaacatttc tctagtactt gcacttatta tcttttgtct aatttaacct taactgaatt    3609 ctccgtttct cctggaggca tttatattca gtgataattc cttccctttag atgcataggg   3669 agagtctcta aatttgatgg aaatggacac ttgagtagtg acttagcctt atgtactctg    3729 ttggaatttg tgctagcagt ttgagcacta gttctgtgtg cctaggaagt taatgctgct    3789 tattgtctca ttctgacttc atggagaatt aatcccacct ttaagcaaag gctactaagt    3849 taatggtatt ttctgtgcag aaattaaatt ttattttcag catttagccc aggaattctt    3909 ccagtaggtg ctcagctatt taaaaacaaa actattctca acattcatc attagacaac     3969 tggagttttt gctggtttttg taacctacca aaatggatag gctgttgaac attccacatt   4029 caaaagtttt gtagggtggt gggaaatggg ggatcttcaa tgtttatttt aaaataaaat    4089
```

```
aaaataagtt cttgactttt ctcatgtgtg gttgtggtac atcatattgg aagggttaac    4149
ctgttacttt ggcaaatgag tattttttg ctagcacctc cccttgcgtg ctttaaatga     4209
catctgcctg ggatgtacca caaccatatg ttacctgtat cttagggaa tggataaaat     4269 atttgtggtt tactgggtaa tccctagatg atgtatgctt gcagtcctat ataaaactaa    4329
atttgctatc tgtgtagaaa ataatttcat gacatttaca atcaggactg aagtaagttc    4389
ttcacacagt gacctctgaa tcagtttcag agaaggatg ggggagaaaa tgccttctag     4449
gttttgaact tctatgcatt agtgcagatg ttgtgaatgt gtaaaggtgt tcatagtttg    4509
actgttccta tgtatgtttt ttcaaagaat tgttccttt tttgaactat aattttttctt    4569 tttttggtta ttttaccatc acagtttaaa tgtatatctt ttatgtctct actcagacca    4629 tattttaaa ggggtgcctc attatggggc agagaacttt tcaataagtc tcattaagat     4689
ctgaatcttg gttctaagca ttctgtataa tatgtgattg cttgtcctag ctgcagaagg    4749
ccttttgttt ggtcaaatgc atattttagc agagtttcaa ggaaatgatt gtcacacatg    4809
tcactgtagc ctcttggtgt agcaagctca catacaaaat acttttgtat atgcataata    4869
taaatcatct catgtggata tgaaacttct tttttaaaac ttaaaaaggt agaatgttat    4929
tgattacctt gattagggca gttttattc cagatcctaa taattcctaa aaaatatgga     4989 aaagttttt ttcaatcatt gtaccttgat attaaaacaa atatccttta agtatttcta     5049
atcagttagc ttctacagtt cttttgtctc cttttatatg cagctcttac gtgggagact    5109
tttccactta aaggagacat agaatgtgtg cttattctca gaaggttcat taactgaggt    5169
gatgagttaa caactagttg agcagtcagc ttcctaagtg ttttaggaca tttgttcatt    5229
atattttccg tcatataact agaggaagtg gaatgcagat aagtgccgaa ttcaaaccct    5289
tcattttatg tttaagctcc tgaatctgca ttccacttgg gttgttttta agcattctaa    5349
attttagttg attataagtt agatttcaca gaatcagtat tgcccttgat cttgtccttt    5409
ttatggagtt aacggggagg aagacccctc aggaaaacga aagtaaattg ttaaggctca    5469
tcttcatacc ttttccatt ttgaatccta caaaaatact gcaaaagact agtgaatgtt     5529
taaaattaca ctagattaaa aatatgaaa gtc                                   5562
```

<210> SEQ ID NO 2
<211> LENGTH: 709
<212> TYPE: PRT
<213> ORGANISM: Homo sapiens

<400> SEQUENCE: 2

```
Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Gly Ala Ala Ala Pro Ala Ser Gln His Pro Ala Thr Gly Thr Gly Ala
            35                  40                  45

Val Gln Thr Glu Ala Met Lys Gln Ile Leu Gly Val Ile Asp Lys Lys
        50                  55                  60

Leu Arg Asn Leu Glu Lys Lys Lys Gly Lys Leu Asp Asp Tyr Gln Glu
    65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110
```

-continued

```
Gln Arg Ser Phe Met Ala Leu Ser Gln Asp Ile Gln Lys Thr Ile Lys
            115                 120                 125
Lys Thr Ala Arg Arg Glu Gln Leu Met Arg Glu Glu Ala Glu Gln Lys
    130                 135                 140
Arg Leu Lys Thr Val Leu Glu Leu Gln Tyr Val Leu Asp Lys Leu Gly
145                 150                 155                 160
Asp Asp Glu Val Arg Thr Asp Leu Lys Gln Gly Leu Asn Gly Val Pro
                165                 170                 175
Ile Leu Ser Glu Glu Leu Ser Leu Leu Asp Glu Phe Tyr Lys Leu
                180                 185                 190
Val Asp Pro Glu Arg Asp Met Ser Leu Arg Leu Asn Glu Gln Tyr Glu
                195                 200                 205
His Ala Ser Ile His Leu Trp Asp Leu Leu Glu Gly Lys Glu Lys Pro
    210                 215                 220
Val Cys Gly Thr Thr Tyr Lys Val Leu Lys Glu Ile Val Glu Arg Val
225                 230                 235                 240
Phe Gln Ser Asn Tyr Phe Asp Ser Thr His Asn His Gln Asn Gly Leu
                245                 250                 255
Cys Glu Glu Glu Ala Ala Ser Ala Pro Ala Val Gly Asp Gln Val
                260                 265                 270
Pro Glu Ala Glu Pro Glu Pro Ala Glu Glu Tyr Thr Glu Gln Ser Glu
    275                 280                 285
Val Glu Ser Thr Glu Tyr Val Asn Arg Gln Phe Met Ala Glu Thr Gln
    290                 295                 300
Phe Thr Ser Gly Glu Lys Glu Gln Val Asp Glu Trp Thr Val Glu Thr
305                 310                 315                 320
Val Glu Val Val Asn Ser Leu Gln Gln Gln Pro Gln Ala Ala Ser Pro
                325                 330                 335
Ser Val Pro Glu Pro His Ser Leu Thr Pro Val Ala Gln Ala Asp Pro
                340                 345                 350
Leu Val Arg Arg Gln Arg Val Gln Asp Leu Met Ala Gln Met Gln Gly
            355                 360                 365
Pro Tyr Asn Phe Ile Gln Asp Ser Met Leu Asp Phe Glu Asn Gln Thr
    370                 375                 380
Leu Asp Pro Ala Ile Val Ser Ala Gln Pro Met Asn Pro Thr Gln Asn
385                 390                 395                 400
Met Asp Met Pro Gln Leu Val Cys Pro Pro Val His Ser Glu Ser Arg
                405                 410                 415
Leu Ala Gln Pro Asn Gln Val Pro Gln Pro Glu Ala Thr Gln Val
                420                 425                 430
Pro Leu Val Ser Ser Thr Ser Glu Gly Tyr Thr Ala Ser Gln Pro Leu
    435                 440                 445
Tyr Gln Pro Ser His Ala Thr Glu Gln Arg Pro Gln Lys Glu Pro Ile
    450                 455                 460
Asp Gln Ile Gln Ala Thr Ile Ser Leu Asn Thr Asp Gln Thr Thr Ala
465                 470                 475                 480
Ser Ser Ser Leu Pro Ala Ala Ser Gln Pro Gln Val Phe Gln Ala Gly
                485                 490                 495
Thr Ser Lys Pro Leu His Ser Ser Gly Ile Asn Val Asn Ala Ala Pro
            500                 505                 510
Phe Gln Ser Met Gln Thr Val Phe Asn Met Asn Ala Pro Val Pro Pro
    515                 520                 525
```

```
Val Asn Glu Pro Glu Thr Leu Lys Gln Gln Asn Gln Tyr Gln Ala Ser
    530                 535                 540
Tyr Asn Gln Ser Phe Ser Ser Gln Pro His Gln Val Glu Gln Thr Glu
545                 550                 555                 560
Leu Gln Gln Glu Gln Leu Gln Thr Val Val Gly Thr Tyr His Gly Ser
                565                 570                 575
Pro Asp Gln Ser His Gln Val Thr Gly Asn His Gln Pro Pro Gln
            580                 585                 590
Gln Asn Thr Gly Phe Pro Arg Ser Asn Gln Pro Tyr Tyr Asn Ser Arg
        595                 600                 605
Gly Val Ser Arg Gly Gly Ser Arg Gly Ala Arg Gly Leu Met Asn Gly
    610                 615                 620
Tyr Arg Gly Pro Ala Asn Gly Phe Arg Gly Gly Tyr Asp Gly Tyr Arg
625                 630                 635                 640
Pro Ser Phe Ser Asn Thr Pro Asn Ser Gly Tyr Thr Gln Ser Gln Phe
                645                 650                 655
Ser Ala Pro Arg Asp Tyr Ser Gly Tyr Gln Arg Asp Gly Tyr Gln Gln
            660                 665                 670
Asn Phe Lys Arg Gly Ser Gly Gln Ser Gly Pro Arg Gly Ala Pro Arg
        675                 680                 685
Gly Arg Gly Gly Pro Pro Arg Pro Asn Arg Gly Met Pro Gln Met Asn
    690                 695                 700
Thr Gln Gln Val Asn
705

<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)
<223> OTHER INFORMATION:

<400> SEQUENCE: 3
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccaccccttg cccctcagc tgcccactcg tgatttccag cggcctccgc     180 gcgcgcacg atg ccc tcg gcc acc agc cac agc ggg agc ggc agc aag tcg    231
            Met Pro Ser Ala Thr Ser His Ser Gly Ser Gly Ser Lys Ser
              1               5                  10 tcc gga ccg cca ccg ccg tcg ggt tcc tcc ggg agt gag gcg gcc gcg    279
Ser Gly Pro Pro Pro Pro Ser Gly Ser Ser Gly Ser Glu Ala Ala Ala
15                  20                  25                  30 gga gcc ggg gcc gcc gcg ccg gct tct cag cac ccc gca acc ggc acc    327
Gly Ala Gly Ala Ala Ala Pro Ala Ser Gln His Pro Ala Thr Gly Thr
                35                  40                  45 ggc gct gtc cag acc gag gcc atg aag cag att ctc ggg gtg atc gac    375
Gly Ala Val Gln Thr Glu Ala Met Lys Gln Ile Leu Gly Val Ile Asp
            50                  55                  60 aag aaa ctt cgg aac ctg gag aag aaa aag ggt aag ctt gat gat tac    423
Lys Lys Leu Arg Asn Leu Glu Lys Lys Lys Gly Lys Leu Asp Asp Tyr
65                  70                  75 cag gaa cga atg aac aaa ggg gaa agg ctt aat caa gat cag ctg gat    471
Gln Glu Arg Met Asn Lys Gly Glu Arg Leu Asn Gln Asp Gln Leu Asp
        80                  85                  90 gcc gtt tct aag tac cag gaa gtc aca aat aat ttg gag ttt gca aaa    519
```

```
              Ala Val Ser Lys Tyr Gln Glu Val Thr Asn Asn Leu Glu Phe Ala Lys
              95                  100                 105                 110 gaa tta cag agg agt ttc atg gca cta agt caa gat att cag aaa aca               567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa               615
Ile Lys Lys Thr Ala Arg Arg Glu Gln Leu Met Arg Glu Glu Ala Glu
            130                 135                 140 cag aaa cgt tta aaa act gta ctt gag cta cag tat gtt ttg gac aaa               663
Gln Lys Arg Leu Lys Thr Val Leu Glu Leu Gln Tyr Val Leu Asp Lys
        145                 150                 155 ttg gga gat gat gaa gtg cgg act gac ctg aaa caa ggt ttg aat gga               711
Leu Gly Asp Asp Glu Val Arg Thr Asp Leu Lys Gln Gly Leu Asn Gly
    160                 165                 170 gtg cca ata ttg tcc gaa gag gag ttg tca ttg ttg gat gaa ttc tat               759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag               807
Lys Leu Val Asp Pro Glu Arg Asp Met Ser Leu Arg Leu Asn Glu Gln
                195                 200                 205 tat gaa cat gcc tcc att cac ctg tgg gac ctg ctg gaa ggg aag gaa               855
Tyr Glu His Ala Ser Ile His Leu Trp Asp Leu Leu Glu Gly Lys Glu
            210                 215                 220 aaa cct gta tgt gga acc acc tat aaa gtt cta aag gaa att gtt gag               903
Lys Pro Val Cys Gly Thr Thr Tyr Lys Val Leu Lys Glu Ile Val Glu
        225                 230                 235 cgt gtt ttt cag tca aac tac ttt gac agc acc cac aac cac cag aat               951
Arg Val Phe Gln Ser Asn Tyr Phe Asp Ser Thr His Asn His Gln Asn
    240                 245                 250 ggg ctg tgt gag gaa gaa gag gca gcc tca gca cct gca gtt gaa gac               999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa              1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa              1095
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt              1143
Thr Gln Phe Thr Ser Gly Glu Lys Glu Gln Val Asp Glu Trp Thr Val
        305                 310                 315 gaa acg gtt gag gtg gta aat tca ctc cag cag caa cct cag gct gca              1191
Glu Thr Val Glu Val Val Asn Ser Leu Gln Gln Gln Pro Gln Ala Ala
    320                 325                 330 tcc cct tca gta cca gag ccc cac tct ttg act cca gtg gct cag gca              1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg              1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat              1335
Gln Gly Pro Tyr Asn Phe Ile Gln Asp Ser Met Leu Asp Phe Glu Asn
            370                 375                 380 cag aca ctt gat cct gcc att gta tct gca cag cct atg aat cca aca              1383
Gln Thr Leu Asp Pro Ala Ile Val Ser Ala Gln Pro Met Asn Pro Thr
        385                 390                 395 caa aac atg gac atg ccc cag ctg gtt tgc cct cca gtt cat tct gaa              1431
Gln Asn Met Asp Met Pro Gln Leu Val Cys Pro Pro Val His Ser Glu
    400                 405                 410
```

| | |
|---|---:|
| tct aga ctt gct cag cct aat caa gtt cct gta caa cca gaa gcg aca<br>Ser Arg Leu Ala Gln Pro Asn Gln Val Pro Val Gln Pro Glu Ala Thr<br>415                         420                         425                      430 | 1479 |
| cag gtt cct ttg gta tca tcc aca agt gag ggg tac aca gca tct caa<br>Gln Val Pro Leu Val Ser Ser Thr Ser Glu Gly Tyr Thr Ala Ser Gln<br>                        435                         440                         445 | 1527 |
| ccc ttg tac cag cct tct cat gct aca gag caa cga cca cag aag gaa<br>Pro Leu Tyr Gln Pro Ser His Ala Thr Glu Gln Arg Pro Gln Lys Glu<br>                        450                         455                         460 | 1575 |
| cca att gat cag att cag gca aca atc tct tta aat aca gac cag act<br>Pro Ile Asp Gln Ile Gln Ala Thr Ile Ser Leu Asn Thr Asp Gln Thr<br>               465                        470                         475 | 1623 |
| aca gca tca tca tcc ctt cct gct gcg tct cag cct caa gta ttt cag<br>Thr Ala Ser Ser Ser Leu Pro Ala Ala Ser Gln Pro Gln Val Phe Gln<br>     480                         485                         490 | 1671 |
| gct ggg aca agc aaa cct tta cat agc agt gga atc aat gta aat gca<br>Ala Gly Thr Ser Lys Pro Leu His Ser Ser Gly Ile Asn Val Asn Ala<br>495                         500                         505                        510 | 1719 |
| gct cca ttc caa tcc atg caa acg gtg ttc aat atg aat gcc cca gtt<br>Ala Pro Phe Gln Ser Met Gln Thr Val Phe Asn Met Asn Ala Pro Val<br>                        515                         520                         525 | 1767 |
| cct cct gtt aat gaa cca gaa act tta aaa cag caa aat cag tac cag<br>Pro Pro Val Asn Glu Pro Glu Thr Leu Lys Gln Gln Asn Gln Tyr Gln<br>               530                        535                         540 | 1815 |
| gcc agt tat aac cag agc ttt tct agt cag cct cac caa gta gaa caa<br>Ala Ser Tyr Asn Gln Ser Phe Ser Ser Gln Pro His Gln Val Glu Gln<br>     545                         550                         555 | 1863 |
| aca gag ctt cag caa gaa cag ctt caa aca gtg gtt ggc act tac cat<br>Thr Glu Leu Gln Gln Glu Gln Leu Gln Thr Val Val Gly Thr Tyr His<br>560                         565                         570 | 1911 |
| ggt tcc cca gac cag tcc cat caa gtg act ggt aac cac cag cag cct<br>Gly Ser Pro Asp Gln Ser His Gln Val Thr Gly Asn His Gln Gln Pro<br>575                         580                         585                        590 | 1959 |
| cct cag cag aac act gga ttt cca cgt agc aat cag ccc tat tac aat<br>Pro Gln Gln Asn Thr Gly Phe Pro Arg Ser Asn Gln Pro Tyr Tyr Asn<br>                        595                         600                         605 | 2007 |
| agt cgt ggt gtg tct cgt gga ggc tcc cgt ggt gct aga ggc ttg atg<br>Ser Arg Gly Val Ser Arg Gly Gly Ser Arg Gly Ala Arg Gly Leu Met<br>               610                        615                         620 | 2055 |
| aat gga tac cgg ggc cct gcc aat gga ttc aga gga gga tat gat ggt<br>Asn Gly Tyr Arg Gly Pro Ala Asn Gly Phe Arg Gly Gly Tyr Asp Gly<br>     625                         630                         635 | 2103 |
| tac cgc cct tca ttc tct aac act cca aac agt ggt tat aca cag tct<br>Tyr Arg Pro Ser Phe Ser Asn Thr Pro Asn Ser Gly Tyr Thr Gln Ser<br>640                         645                         650 | 2151 |
| cag ttc agt gct ccc cgg gat tac tct ggc tat caa cgg gat gga tat<br>Gln Phe Ser Ala Pro Arg Asp Tyr Ser Gly Tyr Gln Arg Asp Gly Tyr<br>655                         660                         665                        670 | 2199 |
| cag cag aat ttc aag cga ggc tct ggg cag agt gga cca cgg gga gcc<br>Gln Gln Asn Phe Lys Arg Gly Ser Gly Gln Ser Gly Pro Arg Gly Ala<br>                        675                         680                         685 | 2247 |
| cca cga ggt aat att ttg tgg tgg tga tcctagctcc taagtggagc<br>Pro Arg Gly Asn Ile Leu Trp Trp<br>               690 | 2294 |
| ttctgttctg gccttggaag agctgttaat agtctgcatg ttaggaatac atttatcctt | 2354 |
| tccagacttg ttgctaggga ttaaatgaaa tgctctgttt ctaaaactta atcttggacc | 2414 |
| caaattttaa ttttgaatg atttaatttt ccctgttact atataaactg tcttgaaaac | 2474 |
| tagaacatat tctcttctca gaaaagtgt ttttccaact gaaaattatt tttcaggtcc | 2534 |

```
taaaacctgc taaatgtttt taggaagtac ttactgaaac attttttgtaa gacattttg    2594
gaatgagatt gaacatttat ataaatttat tattcctctt tcattttttt gaaacatgcc    2654
tattatattt tagggccaga cacccttttaa tggccggata agccatagtt aacatttaga   2714
gaaccattta gaagtgatag aactaatgga atttgcaatg ccttttggac ctctattagt    2774
gatataaata tcaagttatt tctgactttt aaacaaaact cccaaattcc taacttattg    2834
agctatactt aaaaaaaatt acaggtttag agagttttttt gtttttctttt tactgttgga 2894
aaactacttc ccattttggc aggaagttaa cctatttaac aattagagct agcatttcat    2954
gtagtctgaa attctaaatg gttctctgat ttgagggagg ttaaacatca aacaggtttc    3014
ctctattggc cataacatgt ataaaatgtg tgttaaggag gaattacaac gtactttgat    3074
ttgaatacta gtagaaactg gccaggaaaa aggtacattt ttctaaaaat taatggatca    3134
cttgggaatt actgacttga ctagaagtat caaaggatgt ttgcatgtga atgtgggtta    3194
tgttctttcc caccttgtag catattcgat gaaagttgag ttaactgata gctaaaaatc    3254
tgttttaaca gcatgtaaaa agttatttta tctgttaaaa gtcattatac agttttgaat    3314
gttatgtagt ttcttttttaa cagtttaggt aataaggtct gttttcattc tggtgctttt   3374
attaattttg atagtatgat gttacttact actgaaatgt aagctagagt gtacactaga   3434
atgtaagctc catgagagca ggtaccttgt ctgtcttctc tgctgtatct attcccaacg   3494
cttgatgatg gtgcctggca catagtaggc actcaataaa tatttgttga atgaatgaa    3553
```

```
<210> SEQ ID NO 4
<211> LENGTH: 694
<212> TYPE: PRT
<213> ORGANISM: Homo sapiens

<400> SEQUENCE: 4
```

```
Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Gly Ala Ala Ala Pro Ala Ser Gln His Pro Ala Thr Gly Thr Gly Ala
            35                  40                  45

Val Gln Thr Glu Ala Met Lys Gln Ile Leu Gly Val Ile Asp Lys Lys
50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
                100                 105                 110

Gln Arg Ser Phe Met Ala Leu Ser Gln Asp Ile Gln Lys Thr Ile Lys
            115                 120                 125

Lys Thr Ala Arg Arg Glu Gln Leu Met Arg Glu Glu Ala Glu Gln Lys
        130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190
```

```
Val Asp Pro Glu Arg Asp Met Ser Leu Arg Leu Asn Glu Gln Tyr Glu
    195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Ala Ala Ser Ala Pro Ala Val Glu Asp Gln Val
                260                 265                 270

Pro Glu Ala Glu Pro Glu Pro Ala Glu Glu Tyr Thr Glu Gln Ser Glu
                275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Pro Gln Ala Ala Ser Pro
                325                 330                 335

Ser Val Pro Glu Pro His Ser Leu Thr Pro Val Ala Gln Ala Asp Pro
                340                 345                 350

Leu Val Arg Arg Gln Arg Val Gln Asp Leu Met Ala Gln Met Gln Gly
                355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
                420                 425                 430

Pro Leu Val Ser Ser Thr Ser Glu Gly Tyr Thr Ala Ser Gln Pro Leu
    435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
                500                 505                 510

Phe Gln Ser Met Gln Thr Val Phe Asn Met Asn Ala Pro Val Pro Pro
    515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Pro Pro Gln
                580                 585                 590

Gln Asn Thr Gly Phe Pro Arg Ser Asn Gln Pro Tyr Tyr Asn Ser Arg
    595                 600                 605

Gly Val Ser Arg Gly Gly Ser Arg Gly Ala Arg Gly Leu Met Asn Gly
```

```
                    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Asn Ile Leu Trp Trp
    690

<210> SEQ ID NO 5
<211> LENGTH: 18
<212> TYPE: PRT
<213> ORGANISM: Homo sapiens

<400> SEQUENCE: 5

Val Phe Asn Met Asn Ala Pro Val Pro Pro Val Asn Glu Pro Glu Thr
1               5                   10                  15

Leu Lys

<210> SEQ ID NO 6
<211> LENGTH: 5
<212> TYPE: PRT
<213> ORGANISM: Mus musculus

<400> SEQUENCE: 6

Ser Tyr Gly Met Ser
1               5

<210> SEQ ID NO 7
<211> LENGTH: 14
<212> TYPE: PRT
<213> ORGANISM: Mus musculus

<400> SEQUENCE: 7

Trp Val Arg Gln Thr Pro Glu Lys Arg Leu Glu Trp Val Ala
1               5                   10

<210> SEQ ID NO 8
<211> LENGTH: 11
<212> TYPE: PRT
<213> ORGANISM: Mus musculus

<400> SEQUENCE: 8

Leu Ala Ser Tyr Tyr Phe Asp Tyr Trp Gly Gln
1               5                   10

<210> SEQ ID NO 9
<211> LENGTH: 110
<212> TYPE: PRT
<213> ORGANISM: Mus musculus

<400> SEQUENCE: 9

Gly Gly Gly Leu Val Lys Pro Gly Gly Ser Leu Lys Leu Ser Cys Ala
1               5                   10                  15

Ala Ser Gly Phe Thr Phe Ser Ser Tyr Gly Met Ser Trp Val Arg Gln
            20                  25                  30

Thr Pro Glu Lys Arg Leu Glu Trp Val Ala Thr Ile Ser Ser Gly Gly
        35                  40                  45
```

```
Ser Tyr Thr Tyr Tyr Pro Asp Ser Val Lys Gly Arg Phe Thr Ile Ser
 50                  55                  60
Arg Asp Asn Ala Lys Asn Thr Leu Tyr Leu Gln Met Ser Ser Leu Arg
 65                  70                  75                  80
Ser Glu Asp Thr Ala Met Tyr Tyr Cys Ala Ser Leu Ala Ser Tyr Tyr
                 85                  90                  95
Phe Asp Tyr Trp Gly Gln Gly Thr Thr Leu Thr Val Ser Ser
                100                 105                 110
```

```
<210> SEQ ID NO 10
<211> LENGTH: 15
<212> TYPE: PRT
<213> ORGANISM: Mus musculus

<400> SEQUENCE: 10

Thr Met Thr Cys Gln Ala Ser Gln Gly Thr Ser Ile Asn Leu Asn
1               5                   10                  15
```

```
<210> SEQ ID NO 11
<211> LENGTH: 7
<212> TYPE: PRT
<213> ORGANISM: Mus musculus

<400> SEQUENCE: 11

Gly Ala Ser Ser Leu Glu Asp
1               5
```

```
<210> SEQ ID NO 12
<211> LENGTH: 11
<212> TYPE: PRT
<213> ORGANISM: Mus musculus

<400> SEQUENCE: 12

Leu Gln His Ser Tyr Leu Pro Pro Leu Thr Phe
1               5                   10
```

```
<210> SEQ ID NO 13
<211> LENGTH: 113
<212> TYPE: PRT
<213> ORGANISM: Mus musculus

<400> SEQUENCE: 13

Gly Ala Arg Cys Asp Val Gln Met Ile Gln Ser Pro Ser Ser Leu Ser
1               5                   10                  15
Ala Ser Leu Gly Asp Ile Val Thr Met Thr Cys Gln Ala Ser Gln Gly
                20                  25                  30
Thr Ser Ile Asn Leu Asn Trp Phe Gln Gln Lys Pro Gly Lys Ala Pro
             35                  40                  45
Lys Leu Leu Ile Tyr Gly Ala Ser Ser Leu Glu Asp Gly Val Pro Ser
 50                  55                  60
Arg Phe Ser Gly Ser Cys Phe Thr Asp Phe Thr Leu Thr Ile Ser
 65                  70                  75                  80
Ser Leu Glu Asp Glu Asp Met Ala Thr Tyr Phe Cys Leu Gln His Ser
                 85                  90                  95
Tyr Leu Pro Pro Leu Thr Phe Gly Ala Gly Thr Lys Leu Glu Leu Lys
                100                 105                 110
Arg
```

```
<210> SEQ ID NO 14
```

```
<211> LENGTH: 330
<212> TYPE: DNA
<213> ORGANISM: Mus musculus

<400> SEQUENCE: 14
gggggaggct tagtgaagcc tggagggtcc ctgaaactct cctgtgcagc ctctggattc      60
actttcagta gctatggcat gtcttgggtt cgccagactc cggagaagag gctggagtgg     120
gtcgcaacca ttagtagtgg tggtagttac acctactatc agacagtgt gaagggtcga      180 ttcaccatct ccagagacaa tgccaagaac accctgtacc tgcaaatgag cagtctgagg     240
tctgaggaca cggccatgta ttactgtgca agcctggcct cctactactt tgactactgg     300
ggccaaggca ccactctcac agtctcctca                                      330

<210> SEQ ID NO 15
<211> LENGTH: 339
<212> TYPE: DNA
<213> ORGANISM: Mus musculus

<400> SEQUENCE: 15
ggtgccagat gtgatgtcca gatgattcag tctccatcct ccctgtctgc atctttggga     60
gacatagtca ccatgacttg ccaggcaagt cagggcacta gcattaattt aaactggttt    120
cagcaaaaac cagggaaagc tcctaagctc ctgatctatg gtgcaagcag cttggaagat    180
ggggtcccat caaggttcag tggcagttgt tttgggacag atttcactct caccatcagc    240
agcctggagg atgaagatat ggcaacttat ttctgtctac agcatagtta tctccctccg    300
ctcacgttcg gtgctgggac caagctggag ctgaaacgt                           339

<210> SEQ ID NO 16
<211> LENGTH: 5
<212> TYPE: PRT
<213> ORGANISM: Mus musculus

<400> SEQUENCE: 16

Thr Tyr Asp Leu His
1               5

<210> SEQ ID NO 17
<211> LENGTH: 16
<212> TYPE: PRT
<213> ORGANISM: Mus musculus

<400> SEQUENCE: 17

Val Ile Trp Ser Gly Gly Ser Thr Asp Tyr Asn Ala Ala Phe Ile Ser
1               5                   10                  15

<210> SEQ ID NO 18
<211> LENGTH: 11
<212> TYPE: PRT
<213> ORGANISM: Mus musculus

<400> SEQUENCE: 18

Asn Tyr Gly Tyr Ser Ala Trp Phe Ala Tyr Trp
1               5                   10

<210> SEQ ID NO 19
<211> LENGTH: 111
<212> TYPE: PRT
<213> ORGANISM: Mus musculus

<400> SEQUENCE: 19
```

Gly Pro Gly Leu Val Gln Pro Ser Gln Ser Leu Ser Ile Thr Cys Thr
1               5                   10                  15

Val Ser Gly Phe Ser Leu Thr Thr Tyr Asp Leu His Trp Val Arg Gln
            20                  25                  30

Ser Pro Gly Lys Gly Leu Glu Trp Leu Gly Val Ile Trp Ser Gly Gly
            35                  40                  45

Ser Thr Asp Tyr Asn Ala Ala Phe Ile Ser Arg Leu Ser Ile Ser Lys
    50                  55                  60

Asp Asn Ser Lys Ser Gln Val Phe Phe Lys Met Asn Ser Leu Gln Ala
65                  70                  75                  80

Asn Asp Thr Ala Ile Tyr Tyr Cys Ala Arg Asn Tyr Gly Tyr Ser Ala
                85                  90                  95

Trp Phe Ala Tyr Trp Gly Gln Gly Thr Leu Val Thr Val Ser Ala
            100                 105                 110

<210> SEQ ID NO 20
<211> LENGTH: 15
<212> TYPE: PRT
<213> ORGANISM: Mus musculus

<400> SEQUENCE: 20

Ala Ser Ile Ser Cys Arg Ser Ser Gln Ser Ile Val His Ser Asn
1               5                   10                  15

<210> SEQ ID NO 21
<211> LENGTH: 7
<212> TYPE: PRT
<213> ORGANISM: Mus musculus

<400> SEQUENCE: 21

Lys Val Ser Asn Arg Phe Ser
1               5

<210> SEQ ID NO 22
<211> LENGTH: 9
<212> TYPE: PRT
<213> ORGANISM: Mus musculus

<400> SEQUENCE: 22

Phe Gln Gly Ser His Val Pro Leu Thr
1               5

<210> SEQ ID NO 23
<211> LENGTH: 118
<212> TYPE: PRT
<213> ORGANISM: Mus musculus

<400> SEQUENCE: 23

Pro Ala Ser Ser Ser Asp Val Leu Met Thr Gln Thr Pro Leu Ser Leu
1               5                   10                  15

Pro Val Ser Leu Gly Asp Gln Ala Ser Ile Ser Cys Arg Ser Ser Gln
            20                  25                  30

Ser Ile Val His Ser Asn Gly Asn Thr Tyr Leu Glu Trp Tyr Leu Gln
            35                  40                  45

Lys Pro Gly Gln Ser Pro Lys Leu Leu Ile Tyr Lys Val Ser Asn Arg
    50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Leu Gly Val Tyr
                85                  90                  95

Tyr Cys Phe Gln Gly Ser His Val Pro Leu Thr Phe Gly Ala Gly Thr
                100                 105                 110

Lys Leu Glu Leu Lys Arg
        115

<210> SEQ ID NO 24
<211> LENGTH: 333
<212> TYPE: DNA
<213> ORGANISM: Mus musculus

<400> SEQUENCE: 24
ggacctggcc tagtgcagcc ctcacagagc ctgtccatca cctgcacagt ctctggtttc      60
tcattgacta cctatgattt acactgggtt cgccagtctc caggaaaggg tctggagtgg     120
ctgggagtga tatggagtgg tggaagcaca gactataatg cagctttcat atccagactg     180
agcatcagca aggacaattc caagagccaa gttttcttta aaatgaacag tctgcaagct     240
aatgacacag ccatatatta ctgtgccaga aactacggct actccgcctg gtttgcttac     300
tggggccaag ggactctggt cactgtctct gca                                   333

<210> SEQ ID NO 25
<211> LENGTH: 354
<212> TYPE: DNA
<213> ORGANISM: Mus musculus

<400> SEQUENCE: 25
cctgcttcca gcagtgatgt tttgatgacc caaactccac tctccctgcc tgtcagtctt      60
ggagatcaag cctccatctc ttgcagatct agtcagagca ttgtacatag taatggaaac     120
acctatttag aatggtacct gcagaaacca ggccagtctc caaagctcct gatctacaaa     180
gtttccaacc gattttctgg ggtcccagac aggttcagtg cagtggatc agggacagat      240 ttcacactca agatcagcag agtggaggct gaggatctgg gagtttatta ctgctttcaa     300
ggttcacatg ttccgctcac gttcggtgct gggaccaagc tggagctgaa acgt           354

<210> SEQ ID NO 26
<211> LENGTH: 148
<212> TYPE: PRT
<213> ORGANISM: Mus musculus

<400> SEQUENCE: 26

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
            130                 135                 140

Pro Ser Val Tyr
145

<210> SEQ ID NO 27
<211> LENGTH: 139
<212> TYPE: PRT
<213> ORGANISM: Mus musculus

<400> SEQUENCE: 27

Met Ser Val Leu Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
    50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110

Ser Thr Leu Thr Phe Gly Ala Gly Thr Lys Leu Glu Leu Lys Arg Ala
        115                 120                 125

Asp Ala Ala Pro Thr Val Ser Asn Pro Tyr Asp
    130                 135

<210> SEQ ID NO 28
<211> LENGTH: 148
<212> TYPE: PRT
<213> ORGANISM: Mus musculus

<400> SEQUENCE: 28

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 29
<211> LENGTH: 132
<212> TYPE: PRT
<213> ORGANISM: Mus musculus

<400> SEQUENCE: 29

Ala Val Leu Arg Cys Ser Arg Gly Leu Leu Val Ile Trp Ile Ser Asp
1               5                   10                  15

Ile Gln Leu Thr Gln Ser Pro Ser Ser Leu Ala Val Thr Ala Gly Glu
            20                  25                  30

Lys Val Thr Met Ser Cys Lys Ser Ser Gln Ser Leu Leu Trp Ser Val
        35                  40                  45

Asn Gln Lys Asn Tyr Leu Ser Trp Tyr Gln Gln Lys Gln Arg Gln Pro
    50                  55                  60

Pro Lys Leu Leu Ile Tyr Gly Ala Ser Ile Arg Glu Ser Trp Val Pro
65                  70                  75                  80

Asp Arg Phe Thr Gly Ser Gly Ser Gly Thr Asp Phe Thr Leu Thr Ile
                85                  90                  95

Ser Asn Val His Ala Glu Asp Leu Ala Val Tyr Tyr Cys Gln His Asn
            100                 105                 110

His Gly Ser Phe Leu Pro Ser Arg Ser Glu Gln Val Pro Ser Trp Arg
        115                 120                 125

Ser Asn Asn Arg
    130

<210> SEQ ID NO 30
<211> LENGTH: 148
<212> TYPE: PRT
<213> ORGANISM: Mus musculus

<400> SEQUENCE: 30

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 31
<211> LENGTH: 117
<212> TYPE: PRT
<213> ORGANISM: Mus musculus

<400> SEQUENCE: 31

Arg Thr Thr Ser His Met Asp Ser Asp Ile Gln Leu Thr Gln Ser Pro
1               5                   10                  15

Ala Ser Leu Ser Ala Ser Val Gly Glu Thr Val Thr Ile Thr Cys Arg
                20                  25                  30

Ala Ser Gly Asn Ile His Asn Tyr Leu Ala Trp Tyr Gln Gln Lys Gln
            35                  40                  45

Gly Lys Ser Pro Gln Leu Leu Val Tyr Asn Ala Lys Thr Leu Ala Asp
    50                  55                  60

Gly Val Pro Ser Arg Phe Ser Gly Ser Gly Ser Gly Thr Gln Tyr Ser
65                  70                  75                  80

Leu Lys Ile Asn Ser Leu Gln Pro Glu Asp Phe Gly Ser Tyr Tyr Cys
                85                  90                  95

Gln His Phe Trp Ser Thr Leu Thr Phe Gly Gly Gly Thr Lys Leu Glu
            100                 105                 110

Ile Lys Gln Ser Asp
        115

<210> SEQ ID NO 32
<211> LENGTH: 148
<212> TYPE: PRT
<213> ORGANISM: Mus musculus

<400> SEQUENCE: 32

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
                20                  25                  30

Pro Gly Ala Ser Val Lys Ile Ser Cys Lys Ala Ser Gly Tyr Thr Phe
            35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 33
<211> LENGTH: 94
<212> TYPE: PRT
<213> ORGANISM: Mus musculus

<400> SEQUENCE: 33

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
                20                  25                  30

Leu Ile Lys Tyr Ala Ser Gln Ser Ile Ser Gly Ile Pro Ser Arg Phe

```
                35                  40                  45
Ser Gly Ser Gly Ser Gly Thr Asp Phe Thr Leu Ser Ile Asn Ser Val
         50                  55                  60
Glu Thr Glu Asp Phe Gly Met Tyr Phe Cys Gln Gln Ser Asn Ser Trp
 65                  70                  75                  80
Pro Tyr Thr Phe Gly Ala Gly Thr Lys Leu Glu Ile Lys Gln
                 85                  90

<210> SEQ ID NO 34
<211> LENGTH: 148
<212> TYPE: PRT
<213> ORGANISM: Mus musculus

<400> SEQUENCE: 34

Met Glu Trp Ser Gly Val Phe Ile Phe Leu Leu Ser Gly Thr Ala Gly
  1               5                  10                  15
Val Leu Ser Glu Val Gln Leu His Gln Phe Gly Ala Glu Leu Val Lys
                 20                  25                  30
Pro Gly Ala Ser Val Lys Ile Ser Cys Lys Ala Ser Gly Tyr Thr Phe
             35                  40                  45
Thr Asp Tyr Asn Met Asp Trp Val Lys Gln Ser His Gly Lys Ser Leu
         50                  55                  60
Glu Trp Ile Gly Asp Ile Asn Pro Asn Tyr Asp Ser Thr Ser Tyr Asn
 65                  70                  75                  80
Gln Lys Phe Lys Gly Lys Ala Thr Leu Thr Val Asp Lys Ser Ser
                 85                  90                  95
Thr Ala Tyr Met Glu Leu Arg Ser Leu Thr Ser Glu Asp Thr Ala Val
                100                 105                 110
Tyr Tyr Cys Ala Arg Ser Arg Ser Tyr Asp Tyr Glu Gly Phe Ala Tyr
            115                 120                 125
Trp Gly Gln Gly Thr Leu Val Thr Val Ser Ala Ala Lys Thr Thr Pro
        130                 135                 140
Pro Ser Val Tyr
145

<210> SEQ ID NO 35
<211> LENGTH: 105
<212> TYPE: PRT
<213> ORGANISM: Mus musculus

<400> SEQUENCE: 35

Gly Leu Phe Cys Ser Val Glu Arg Cys His Tyr Gln Leu Gln Ser Ser
  1               5                  10                  15
Gln Asn Leu Leu Ser Ile Val Asn Arg Tyr His Tyr Met Ser Gly Asn
                 20                  25                  30
Pro Pro Lys Leu Leu Val Tyr Pro Ala Leu Leu Ile Tyr Glu Ala Ser
             35                  40                  45
Ile Thr Lys Ser Cys Val Pro Asp Arg Phe Thr Arg Ser Gly Ser Gly
         50                  55                  60
Thr Asn Phe Thr Leu Thr Ile Asn Phe Val His Ala Asp Asp Leu Ile
 65                  70                  75                  80
Phe Tyr Tyr Cys Gln His Asn Arg Gly Ser Phe Leu Pro Ser Ser Ser
                 85                  90                  95
Val Gln Val Pro Arg Arg Ser Asn
                100                 105
```

```
<210> SEQ ID NO 36
<211> LENGTH: 100
<212> TYPE: PRT
<213> ORGANISM: Mus musculus

<400> SEQUENCE: 36

Asp Ile Leu Gln Ala Ser Gly Tyr Ser Phe Thr Gly Tyr Thr Met Asn
1               5                   10                  15

Trp Val Lys Gln Ser His Gly Lys Asn Leu Glu Trp Ile Gly Leu Ile
            20                  25                  30

Asn Pro Tyr Asn Gly Gly Thr Ser Tyr Asn Gln Lys Phe Lys Gly Lys
        35                  40                  45

Ala Thr Leu Thr Val Asp Lys Ser Ser Ser Thr Ala Tyr Met Glu Leu
    50                  55                  60

Leu Ser Leu Thr Ser Glu Asp Ser Ala Val Tyr Tyr Cys Ala Arg Trp
65                  70                  75                  80

Gly Val Trp Ser Ala Met Asp Tyr Trp Gly Gln Gly Thr Thr Val Thr
                85                  90                  95

Val Ser Ser Lys
            100

<210> SEQ ID NO 37
<211> LENGTH: 90
<212> TYPE: PRT
<213> ORGANISM: Mus musculus

<400> SEQUENCE: 37

Asp Arg Val Ser Ile Thr Cys Lys Ala Ser Gln Asn Val Arg Thr Ala
1               5                   10                  15

Val Ala Trp Tyr Gln Gln Lys Pro Arg Gln Ser Pro Lys Ala Leu Ile
            20                  25                  30

Tyr Leu Ala Ser Asn Arg Asp Thr Gly Leu Pro Asp Arg Phe Pro Gly
        35                  40                  45

Arg Gly Ser Gly Thr Asp Phe Thr Leu Asn Ile Thr Asn Val Gln Ser
    50                  55                  60

Glu Asp Leu Glu Asp Tyr Phe Cys Leu Gln His Cys Asn Tyr Pro Asn
65                  70                  75                  80

Glu Phe Arg Gly Cys Thr Lys Val Pro Ile
                85                  90

<210> SEQ ID NO 38
<211> LENGTH: 116
<212> TYPE: PRT
<213> ORGANISM: Mus musculus

<400> SEQUENCE: 38

Leu Gln Glu Ser Gly Ala Glu Leu Ala Arg Pro Gly Ala Ser Val Lys
1               5                   10                  15

Leu Ser Cys Lys Ala Ser Gly Tyr Thr Phe Thr Ser Tyr Trp Met Gln
            20                  25                  30

Trp Val Lys Gln Arg Pro Gly Gln Gly Leu Glu Trp Ile Gly Ala Ile
            35                  40                  45

Tyr Pro Gly Asp Gly Asp Thr Arg Tyr Thr Gln Lys Phe Lys Gly Lys
        50                  55                  60

Ala Thr Leu Thr Ala Asp Lys Ser Ser Ser Thr Ala Tyr Met Gln Leu
65                  70                  75                  80

Ser Ser Leu Ala Ser Glu Asp Ser Ala Val Tyr Tyr Cys Ala Arg Gly
                85                  90                  95
```

```
Glu Tyr Gly Asn Tyr Phe Ala Tyr Trp Gly Gln Gly Thr Thr Val Thr
                100                 105                 110

Val Ser Ser Asn
        115

<210> SEQ ID NO 39
<211> LENGTH: 100
<212> TYPE: PRT
<213> ORGANISM: Mus musculus

<400> SEQUENCE: 39

Thr Ser Asp Ala Ser Leu Gly Glu Arg Val Thr Ile Thr Cys Lys Ala
1               5                   10                  15

Ser Gln Asp Ile Asn Ser Tyr Leu Ser Trp Phe Gln Gln Lys Pro Gly
            20                  25                  30

Lys Ser Pro Lys Thr Leu Ile Tyr Arg Ala Asn Arg Leu Val Asp Gly
        35                  40                  45

Val Pro Ser Arg Phe Ser Gly Ser Gly Ser Gln Asp Tyr Ser Leu
    50                  55                  60

Thr Ile Ser Ser Leu Glu Tyr Glu Asp Met Gly Ile Tyr Tyr Cys Leu
65                  70                  75                  80

Gln Tyr Asp Glu Phe Pro Leu Thr Phe Gly Gly Thr Lys Leu Glu
                85                  90                  95

Ile Lys Gln Lys
        100

<210> SEQ ID NO 40
<211> LENGTH: 108
<212> TYPE: PRT
<213> ORGANISM: Mus musculus

<400> SEQUENCE: 40

Ala Trp Leu Ser Gln Leu Ser Cys Thr Ala Ser Gly Phe Asn Ile Lys
1               5                   10                  15

Asp Thr Tyr Met His Trp Val Lys Gln Arg Pro Glu Gln Gly Leu Glu
            20                  25                  30

Trp Ile Gly Arg Ile Asp Pro Ala Asn Gly Asn Thr Lys Tyr Asp Pro
        35                  40                  45

Lys Phe Gln Gly Lys Ala Thr Ile Thr Ala Asp Thr Ser Ser Asn Thr
    50                  55                  60

Ala Tyr Leu Gln Leu Ser Ser Leu Thr Ser Glu Asp Thr Ala Val Tyr
65                  70                  75                  80

Tyr Cys Ala Arg Pro Ile His Tyr Tyr Gly Ser Ser Leu Ala Tyr
                85                  90                  95

Trp Gly Gln Gly Thr Thr Val Thr Val Ser Ser Lys
            100                 105

<210> SEQ ID NO 41
<211> LENGTH: 104
<212> TYPE: PRT
<213> ORGANISM: Mus musculus

<400> SEQUENCE: 41

Glu Phe His Ala Val Ser Leu Gly Gln Arg Ala Thr Ile Ser Cys Arg
1               5                   10                  15

Ala Ser Glu Ser Val Asp Ser Tyr Gly Asn Ser Phe Met His Trp Tyr
            20                  25                  30
```

Gln Gln Lys Pro Gly Gln Pro Pro Lys Leu Leu Ile Tyr Arg Ala Ser
        35                  40                  45

Asn Leu Glu Ser Gly Ile Pro Ala Arg Phe Ser Gly Ser Gly Ser Arg
 50                  55                  60

Thr Asp Phe Thr Leu Thr Ile Asn Pro Val Glu Ala Asp Asp Val Ala
 65                  70                  75                  80

Thr Tyr Tyr Cys Gln Gln Ser Asn Glu Asp Pro Gly Arg Ser Glu Val
                 85                  90                  95

Val Pro Ser Trp Arg Ser Asn Lys
                100

<210> SEQ ID NO 42
<211> LENGTH: 109
<212> TYPE: PRT
<213> ORGANISM: Mus musculus

<400> SEQUENCE: 42

Pro Arg Ala Ser Leu Gly Val Ser Glu Thr Leu Leu Cys Thr Ser Gly
 1               5                  10                  15

Phe Thr Phe Thr Asp Tyr Tyr Met Ser Trp Val Arg Gln Pro Pro Gly
                20                  25                  30

Lys Ala Leu Glu Trp Leu Gly Phe Ile Arg Asn Lys Ala Asn Gly Tyr
            35                  40                  45

Thr Thr Glu Tyr Ser Ala Ser Val Lys Gly Arg Phe Thr Ile Ser Arg
     50                  55                  60

Asp Asn Ser Gln Ser Ile Leu Tyr Leu Gln Met Asn Thr Leu Arg Ala
 65                  70                  75                  80

Glu Asp Ser Ala Thr Tyr Tyr Cys Ala Arg Ala Asn Trp Ala Phe Asp
                 85                  90                  95

Tyr Trp Gly Gln Gly Thr Thr Val Thr Val Ser Ser Lys
                100                 105

<210> SEQ ID NO 43
<211> LENGTH: 94
<212> TYPE: PRT
<213> ORGANISM: Mus musculus

<400> SEQUENCE: 43

Ser Gly Asp Arg Val Ser Leu Ser Cys Arg Ala Ser Gln Ser Ile Ser
 1               5                  10                  15

Asn Tyr Leu His Trp Tyr Gln Gln Lys Ser His Glu Ser Pro Arg Leu
                20                  25                  30

Leu Ile Lys Tyr Ala Ser Gln Ser Ile Ser Gly Ile Pro Ser Arg Phe
            35                  40                  45

Ser Gly Ser Gly Ser Gly Thr Asp Phe Thr Leu Ser Ile Asn Ser Val
     50                  55                  60

Glu Thr Glu Asp Phe Gly Met Tyr Phe Cys Gln Gln Ser Asn Ser Trp
 65                  70                  75                  80

Pro Tyr Thr Phe Gly Gly Gly Thr Lys Leu Glu Ile Lys Gln
                 85                  90

<210> SEQ ID NO 44
<211> LENGTH: 111
<212> TYPE: PRT
<213> ORGANISM: Mus musculus

<400> SEQUENCE: 44

Pro Ala Cys Leu Pro Gly Gly Ser Leu Arg Leu Ser Cys Ala Thr Ser
 1               5                  10                  15

```
                1               5                  10                 15
            Gly Phe Thr Phe Thr Asp Tyr Tyr Met Ser Trp Val Arg Gln Pro Pro
                            20                 25                 30
            Gly Lys Ala Leu Glu Trp Leu Gly Phe Ile Arg Asn Lys Ala Asn Gly
                            35                 40                 45
            Tyr Thr Thr Glu Tyr Ser Ala Ser Val Lys Gly Arg Phe Thr Ile Ser
                            50                 55                 60
            Arg Asp Asn Ser Gln Ser Ile Leu Tyr Leu Gln Met Asn Thr Leu Arg
             65                 70                 75                 80
            Ala Glu Asp Ser Ala Thr Tyr Tyr Cys Ala Arg Ala Pro Leu Leu Tyr
                            85                 90                 95
            Tyr Ala Met Asp Tyr Trp Gly Gln Gly Thr Thr Val Thr Val Ser
                           100                105                110

<210> SEQ ID NO 45
<211> LENGTH: 102
<212> TYPE: PRT
<213> ORGANISM: Mus musculus

<400> SEQUENCE: 45

Arg Leu Pro Phe Tyr Ser Leu Glu Gln Arg Ala Thr Ile Ser Tyr Arg
 1               5                  10                 15
Ala Ser Lys Asn Val Ser Thr Ser Gly Tyr Ser Tyr Met His Trp Asn
                20                 25                 30
Gln Gln Lys Pro Gly Gln Pro Pro Lys Leu Leu Ile Tyr Leu Val Ser
                35                 40                 45
Asn Leu Glu Ser Gly Val Pro Ala Arg Phe Ser Gly Ser Gly Ser Gly
                50                 55                 60
Thr Asp Phe Thr Leu Asn Ile His Pro Val Glu Glu Glu Asp Ala Ala
 65                 70                 75                 80
Thr Tyr Tyr Cys Gln His Ile Arg Glu Leu Thr Arg Ser Glu Leu Val
                85                 90                 95
Pro Ser Trp Lys Ser Asn
               100

<210> SEQ ID NO 46
<211> LENGTH: 101
<212> TYPE: PRT
<213> ORGANISM: Mus musculus

<400> SEQUENCE: 46

Val Ser Cys Lys Ala Ser Gly Tyr Thr Phe Thr Ser Tyr Trp Met His
 1               5                  10                 15
Trp Val Lys Gln Arg Pro Gly Gln Gly Leu Glu Trp Ile Gly Met Ile
                20                 25                 30
Asp Pro Ser Asn Ser Glu Thr Arg Leu Asn Gln Lys Phe Lys Asp Lys
                35                 40                 45
Ala Thr Leu Asn Val Asp Lys Ser Ser Asn Thr Ala Tyr Met Gln Leu
                50                 55                 60
Ser Ser Leu Thr Ser Glu Asp Ser Ala Val Tyr Tyr Cys Ala Arg Gly
 65                 70                 75                 80
Leu Arg His Tyr Trp Tyr Phe Asp Val Trp Gly Gln Gly Thr Thr Val
                85                 90                 95
Thr Val Ser Ser Lys
               100
```

-continued

```
<210> SEQ ID NO 47
<211> LENGTH: 99
<212> TYPE: PRT
<213> ORGANISM: Mus musculus

<400> SEQUENCE: 47

Thr Ile Leu Trp Arg Glu Gly Pro Phe Ser Tyr Arg Ala Ser Lys Ser
1               5                   10                  15

Val Ser Thr Ser Gly Tyr Ser Tyr Met His Trp Asn Gln Gln Lys Pro
            20                  25                  30

Gly Gln Pro Pro Arg Leu Leu Ile Tyr Leu Val Ser Asn Leu Glu Ser
        35                  40                  45

Gly Val Pro Ala Arg Phe Ser Gly Ser Gly Ser Gly Thr Asp Phe Thr
    50                  55                  60

Leu Asn Ile His Pro Val Glu Glu Asp Ala Ala Thr Tyr Tyr Cys
65                  70                  75                  80

Gln His Ile Arg Glu Leu Thr Arg Ser Glu Glu Val Pro Ser Trp Arg
                85                  90                  95

Ser Asn Lys

<210> SEQ ID NO 48
<211> LENGTH: 330
<212> TYPE: PRT
<213> ORGANISM: Homo sapiens

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 49
<211> LENGTH: 106
<212> TYPE: PRT
<213> ORGANISM: Homo sapiens

<400> SEQUENCE: 49

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 50
<211> LENGTH: 11
<212> TYPE: PRT
<213> ORGANISM: Mus musculus

<400> SEQUENCE: 50

Lys Ser Ser Gln Ser Leu Leu Tyr Ser Ser Asn
1               5                   10

<210> SEQ ID NO 51
<211> LENGTH: 7
<212> TYPE: PRT
<213> ORGANISM: Mus musculus

<400> SEQUENCE: 51

Trp Ala Ser Thr Arg Glu Ser
1               5

<210> SEQ ID NO 52
<211> LENGTH: 9
<212> TYPE: PRT
<213> ORGANISM: Mus musculus

<400> SEQUENCE: 52

Gln Gln Tyr Tyr Ser Tyr Pro Phe Thr
```

<210> SEQ ID NO 53
<211> LENGTH: 115
<212> TYPE: PRT
<213> ORGANISM: Mus musculus

<400> SEQUENCE: 53

```
Gly Val Ile Val Met Ser Gln Ser Pro Ser Ser Leu Ala Val Ser Leu
1               5                   10                  15

Gly Glu Lys Val Thr Met Ser Cys Lys Ser Ser Gln Ser Leu Leu Tyr
                20                  25                  30

Ser Ser Asn Gln Lys Asn Tyr Leu Ala Trp Tyr Gln Gln Lys Pro Gly
            35                  40                  45

Gln Ser Pro Lys Leu Leu Ile Tyr Trp Ala Ser Thr Arg Glu Ser Gly
        50                  55                  60

Val Pro Asp Arg Phe Thr Gly Ser Gly Ser Gly Thr Asp Phe Thr Leu
65                  70                  75                  80

Thr Ile Ser Ser Val Lys Ala Glu Asp Leu Ala Val Tyr Tyr Cys Gln
                85                  90                  95

Gln Tyr Tyr Ser Tyr Pro Phe Thr Phe Gly Ser Gly Thr Lys Leu Glu
                100                 105                 110

Ile Lys Arg
        115
```

<210> SEQ ID NO 54
<211> LENGTH: 345
<212> TYPE: DNA
<213> ORGANISM: Mus musculus

<400> SEQUENCE: 54

```
ggggtcattg tgatgtcaca gtctccatcc tccctagctg tgtcacttgg agagaaggtt      60
actatgagct gcaagtccag tcagagcctt ttatatagta gcaatcaaaa gaactacttg     120
gcctggtacc agcagaaacc agggcagtct cctaaactgc tgatttactg ggcatccact     180
agggaatctg ggtccctga tcgcttcaca ggcagtggat ctgggacaga tttcactctc     240
accatcagca gtgtgaaggc tgaagacctg gcagtttatt actgtcagca atattatagc    300
tatccattca cgttcggctc ggggacaaag ttggaaataa aacgt                    345
```

<210> SEQ ID NO 55
<211> LENGTH: 4
<212> TYPE: PRT
<213> ORGANISM: Gallus gallus

<400> SEQUENCE: 55

```
His Ser Met Phe
1
```

<210> SEQ ID NO 56
<211> LENGTH: 17
<212> TYPE: PRT
<213> ORGANISM: Gallus gallus

<400> SEQUENCE: 56

```
Gly Ile Tyr Gly Val Gly Arg Ser Ile Arg Tyr Gly Ser Ala Val Lys
1               5                   10                  15

Gly
```

<210> SEQ ID NO 57
<211> LENGTH: 20
<212> TYPE: PRT
<213> ORGANISM: Gallus gallus

<400> SEQUENCE: 57

Ser Gly Tyr Phe Ser Asn Ser Arg Tyr Trp Asp Ser Gly Ala Tyr Phe
1               5                   10                  15

Ile Asp Ala Trp
            20

<210> SEQ ID NO 58
<211> LENGTH: 127
<212> TYPE: PRT
<213> ORGANISM: Gallus gallus

<400> SEQUENCE: 58

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Arg Ser His
            20                  25                  30

Ser Met Phe Trp Val Arg Gln Ala Pro Gly Lys Gly Leu Glu Tyr Val
        35                  40                  45

Ala Gly Ile Tyr Gly Val Gly Arg Ser Ile Arg Tyr Gly Ser Ala Val
    50                  55                  60

Lys Gly Arg Ala Thr Met Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Ser Gly Tyr Phe Ser Asn Ser Arg Tyr Trp Asp Ser Gly Ala
            100                 105                 110

Tyr Phe Ile Asp Ala Trp Gly His Gly Thr Glu Val Ile Val Ser
        115                 120                 125

<210> SEQ ID NO 59
<211> LENGTH: 8
<212> TYPE: PRT
<213> ORGANISM: Gallus gallus

<400> SEQUENCE: 59

Ser Gly Gly Tyr Ser Asn Tyr Gly
1               5

<210> SEQ ID NO 60
<211> LENGTH: 7
<212> TYPE: PRT
<213> ORGANISM: Gallus gallus

<400> SEQUENCE: 60

Tyr Asn Asp Lys Arg Pro Ser
1               5

<210> SEQ ID NO 61
<211> LENGTH: 12
<212> TYPE: PRT
<213> ORGANISM: Gallus gallus

<400> SEQUENCE: 61

Gly Gly Tyr Asp Ser Ser Thr Asp Ala Gly Ile Phe
1               5                   10

<210> SEQ ID NO 62
<211> LENGTH: 103
<212> TYPE: PRT
<213> ORGANISM: Gallus gallus

<400> SEQUENCE: 62

Ala Leu Thr Gln Pro Ala Ser Val Ser Ala Asn Pro Gly Glu Thr Val
1               5                   10                  15

Glu Ile Thr Cys Ser Gly Gly Tyr Ser Asn Tyr Gly Trp Tyr Gln Gln
            20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Ala Thr Leu Thr Ile Thr Gly Val Gln Ala Glu Asp Glu Ala Val
65                  70                  75                  80

Tyr Phe Cys Gly Gly Tyr Asp Ser Ser Thr Asp Ala Gly Ile Phe Gly
                85                  90                  95

Ala Gly Thr Thr Leu Thr Val
            100

<210> SEQ ID NO 63
<211> LENGTH: 127
<212> TYPE: PRT
<213> ORGANISM: Gallus gallus

<400> SEQUENCE: 63

Ala Val Thr Leu Asp Glu Ser Gly Gly Leu Gln Thr Pro Gly Gly Gly
1               5                   10                  15

Ala Leu Ser Leu Val Cys Lys Ala Ser Gly Phe Thr Phe Arg Ser His
            20                  25                  30

Ser Met Phe Trp Val Arg Gln Ala Pro Gly Lys Gly Leu Glu Tyr Val
        35                  40                  45

Ala Gly Ile Tyr Gly Val Gly Arg Ser Ile Arg Tyr Gly Ser Ala Val
    50                  55                  60

Lys Gly Arg Ala Thr Met Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ser Gly Tyr Phe Ser Asn Arg Arg Tyr Trp Asp Ser Gly Ala
            100                 105                 110

Tyr Phe Ile Asp Ala Trp Gly His Gly Thr Glu Val Ile Val Ser
        115                 120                 125

<210> SEQ ID NO 64
<211> LENGTH: 7
<212> TYPE: PRT
<213> ORGANISM: Gallus gallus

<400> SEQUENCE: 64

Glu Asn Asp Lys Arg Pro Ser
1               5

<210> SEQ ID NO 65
<211> LENGTH: 103
<212> TYPE: PRT
<213> ORGANISM: Gallus gallus

<400> SEQUENCE: 65

```
Ala Leu Thr Gln Pro Ala Ser Val Ser Ala Asn Leu Gly Gly Thr Val
1               5                   10                  15

Glu Ile Thr Cys Ser Gly Gly Tyr Ser Asn Tyr Gly Trp Tyr Gln Gln
            20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Arg Ala Glu Asp Glu Ala Val
65                  70                  75                  80

Tyr Tyr Cys Gly Gly Tyr Asp Ser Ser Thr Asp Ala Gly Ile Phe Gly
                85                  90                  95

Ala Gly Thr Thr Leu Thr Val
                100
```

```
<210> SEQ ID NO 66
<211> LENGTH: 4
<212> TYPE: PRT
<213> ORGANISM: Gallus gallus

<400> SEQUENCE: 66

Phe Gly Met Phe
1
```

```
<210> SEQ ID NO 67
<211> LENGTH: 17
<212> TYPE: PRT
<213> ORGANISM: Gallus gallus

<400> SEQUENCE: 67

Ser Ile Ser Asp Asn Gly Arg Ser Thr Tyr Tyr Gly Ser Ala Val Lys
1               5                   10                  15

Gly
```

```
<210> SEQ ID NO 68
<211> LENGTH: 17
<212> TYPE: PRT
<213> ORGANISM: Gallus gallus

<400> SEQUENCE: 68

Asn Ala Tyr Val Gly Arg Gly Cys Cys Phe Ser Tyr Ser Ile Asp Ala
1               5                   10                  15

Trp
```

```
<210> SEQ ID NO 69
<211> LENGTH: 124
<212> TYPE: PRT
<213> ORGANISM: Gallus gallus

<400> SEQUENCE: 69

Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Thr Phe Ser Ser Phe
            20                  25                  30

Gly Met Phe Trp Val Arg Gln Ala Pro Gly Lys Gly Leu Glu Phe Val
            35                  40                  45

Ala Ser Ile Ser Asp Asn Gly Arg Ser Thr Tyr Tyr Gly Ser Ala Val
        50                  55                  60

Lys Gly Arg Ala Thr Ile Ser Arg Asp Asp Gly Gln Ser Thr Val Arg
```

```
                65                  70                  75                  80
Leu Gln Leu Asn Asn Leu Arg Ala Glu Asp Thr Gly Thr Tyr Tyr Cys
                    85                  90                  95
Ala Lys Asn Ala Tyr Val Gly Arg Gly Cys Cys Phe Ser Tyr Ser Ile
                    100                 105                 110
Asp Ala Trp Gly His Gly Thr Glu Val Ile Val Ser
                    115                 120
```

<210> SEQ ID NO 70
<211> LENGTH: 11
<212> TYPE: PRT
<213> ORGANISM: Gallus gallus

<400> SEQUENCE: 70

```
Ser Gly Gly Gly Ser Ser Ser Asp Ala Tyr Gly
1               5                   10
```

<210> SEQ ID NO 71
<211> LENGTH: 7
<212> TYPE: PRT
<213> ORGANISM: Gallus gallus

<400> SEQUENCE: 71

```
Asn Gly Ser Asn Arg Pro Ser
1               5
```

<210> SEQ ID NO 72
<211> LENGTH: 12
<212> TYPE: PRT
<213> ORGANISM: Gallus gallus

<400> SEQUENCE: 72

```
Gly Ser Thr Asp Thr Ser Thr Ser Val Gly Ile Phe
1               5                   10
```

<210> SEQ ID NO 73
<211> LENGTH: 106
<212> TYPE: PRT
<213> ORGANISM: Gallus gallus

<400> SEQUENCE: 73

```
Ala Leu Thr Gln Pro Ala Ser Val Ser Val Asn Pro Gly Glu Thr Val
1               5                   10                  15
Lys Ile Thr Cys Ser Gly Gly Gly Ser Ser Ser Asp Ala Tyr Gly Trp
                20                  25                  30
Tyr Gln Gln Lys Ser Pro Gly Ser Ala Pro Val Thr Leu Ile Tyr Asn
                35                  40                  45
Gly Ser Asn Arg Pro Ser His Ile Pro Ser Arg Phe Ser Gly Ser Thr
            50                  55                  60
Ser Gly Ser Thr Asn Thr Leu Thr Ile Thr Gly Val Gln Val Glu Asp
65                  70                  75                  80
Glu Ala Ile Tyr Phe Cys Gly Ser Thr Asp Thr Ser Thr Ser Val Gly
                    85                  90                  95
Ile Phe Gly Ala Gly Thr Thr Leu Thr Val
                100                 105
```

<210> SEQ ID NO 74
<211> LENGTH: 4
<212> TYPE: PRT
<213> ORGANISM: Gallus gallus

```
<400> SEQUENCE: 74

Tyr Gly Met Gly
1

<210> SEQ ID NO 75
<211> LENGTH: 16
<212> TYPE: PRT
<213> ORGANISM: Gallus gallus

<400> SEQUENCE: 75

Ala Ile Arg Lys Asp Gly Ser Thr Asn Tyr Gly Pro Ala Val Lys Gly
1               5                   10                  15

<210> SEQ ID NO 76
<211> LENGTH: 14
<212> TYPE: PRT
<213> ORGANISM: Gallus gallus

<400> SEQUENCE: 76

Arg Ser His Thr Gly Val Asn Ala Ala Lys Ile Asp Ala Trp
1               5                   10

<210> SEQ ID NO 77
<211> LENGTH: 120
<212> TYPE: PRT
<213> ORGANISM: Gallus gallus

<400> SEQUENCE: 77

Ala Val Thr Leu Asp Glu Ser Gly Gly Leu Gln Thr Pro Gly Gly
1               5                   10                  15

Ala Val Ser Leu Val Cys Lys Gly Ser Gly Phe Thr Phe Ser Ser Tyr
                20                  25                  30

Gly Met Gly Trp Val Arg Gln Ala Pro Gly Lys Gly Leu Glu Tyr Val
            35                  40                  45

Ala Ala Ile Arg Lys Asp Gly Ser Thr Asn Tyr Gly Pro Ala Val Lys
        50                  55                  60

Gly Arg Ala Thr Ile Ser Arg Asp Asn Gly Gln Ser Thr Val Arg Leu
65                  70                  75                  80

Gln Leu Ser Asn Leu Arg Ala Glu Asp Thr Ala Thr Tyr Tyr Cys Ala
                85                  90                  95

Lys Arg Ser His Thr Gly Val Asn Ala Ala Lys Ile Asp Ala Trp Gly
                100                 105                 110

Arg Gly Thr Glu Val Ile Val Ser
            115                 120

<210> SEQ ID NO 78
<211> LENGTH: 8
<212> TYPE: PRT
<213> ORGANISM: Gallus gallus

<400> SEQUENCE: 78

Ser Gly Ala Ser His Asn Tyr Gly
1               5

<210> SEQ ID NO 79
<211> LENGTH: 7
<212> TYPE: PRT
<213> ORGANISM: Gallus gallus

<400> SEQUENCE: 79

Ser Asn Asp Lys Arg Pro Ser
```

```
<210> SEQ ID NO 80
<211> LENGTH: 10
<212> TYPE: PRT
<213> ORGANISM: Gallus gallus

<400> SEQUENCE: 80

Gly Gly Tyr Asn Ile Tyr Gly Pro Thr Phe
1               5                   10

<210> SEQ ID NO 81
<211> LENGTH: 101
<212> TYPE: PRT
<213> ORGANISM: Gallus gallus

<400> SEQUENCE: 81

Ala Leu Thr Gln Pro Ala Ser Val Ser Ala Asn Pro Gly Glu Thr Val
1               5                   10                  15

Lys Ile Thr Cys Ser Gly Ala Ser His Asn Tyr Gly Trp Phe Gln Gln
            20                  25                  30

Lys Ser Pro Gly Ser Ala Pro Val Thr Val Ile Tyr Ser Asn Asp Lys
        35                  40                  45

Arg Pro Ser Asp Ile Pro Ser Arg Phe Ser Gly Ser Lys Ser Gly Ser
    50                  55                  60

Thr Ala Thr Leu Thr Ile Thr Gly Val Gln Ala Asp Asp Glu Ala Val
65                  70                  75                  80

Tyr Phe Cys Gly Gly Tyr Asn Ile Tyr Gly Pro Thr Phe Gly Ala Gly
                85                  90                  95

Thr Thr Leu Thr Val
            100
```